US010220103B2

(12) United States Patent
Zabow et al.

(10) Patent No.: US 10,220,103 B2
(45) Date of Patent: *Mar. 5, 2019

(54) MAGNETIC MICROSTRUCTURES FOR MAGNETIC RESONANCE IMAGING

(71) Applicants: The United States of America, as represented by the Secretary, Depart. of Health and Human Services, Washington, DC (US); THE UNITED STATES OF AMERICA, REPRESENTED BY THE SECRETARY OF COMMERCE, Washington, DC (US)

(72) Inventors: Gary Zabow, Boulder, CO (US); Stephen Dodd, Rockville, MD (US); Alan Koretsky, Bethesda, MD (US); John Moreland, Louisville, CO (US)

(73) Assignees: The United States of America, as Represented by the Secretary, Department of Health and Human Services, Washington, DC (US); The United States of America, as represented by the Secretary of Commerce, Washington, DC (US)

( * ) Notice: Subject to any disclaimer, the term of this patent is extended or adjusted under 35 U.S.C. 154(b) by 503 days.

This patent is subject to a terminal disclaimer.

(21) Appl. No.: 14/739,813

(22) Filed: Jun. 15, 2015

(65) Prior Publication Data
US 2015/0367001 A1    Dec. 24, 2015

Related U.S. Application Data

(60) Division of application No. 12/753,689, filed on Apr. 2, 2010, now Pat. No. 9,084,819, which is a continuation-in-part of application No. PCT/US2009/041142, filed on Apr. 20, 2009.

(60) Provisional application No. 61/166,610, filed on Apr. 3, 2009.

(51) Int. Cl.
*A61K 49/18* (2006.01)
*G01R 33/56* (2006.01)
*A61B 5/055* (2006.01)
*A61B 5/05* (2006.01)
*B82Y 5/00* (2011.01)
*B82Y 30/00* (2011.01)
*G01R 33/563* (2006.01)
*G01R 33/28* (2006.01)

(52) U.S. Cl.
CPC .......... *A61K 49/1818* (2013.01); *A61B 5/055* (2013.01); *A61K 49/18* (2013.01); *B82Y 5/00* (2013.01); *B82Y 30/00* (2013.01); *G01R 33/281* (2013.01); *G01R 33/5601* (2013.01); *G01R 33/563* (2013.01); *G01R 33/5635* (2013.01); *G01R 33/56325* (2013.01); *A61B 5/0515* (2013.01); *Y10T 428/2982* (2015.01)

(58) Field of Classification Search
None
See application file for complete search history.

(56) References Cited

U.S. PATENT DOCUMENTS

| 5,572,132 A | 11/1996 | Pulyer et al. | |
|---|---|---|---|
| 6,107,102 A * | 8/2000 | Ferrari | A61K 9/127 424/417 |
| 6,377,048 B1 | 4/2002 | Golan et al. | |
| 2005/0200438 A1 | 9/2005 | Renaud et al. | |
| 2007/0166730 A1 | 7/2007 | Menon et al. | |

OTHER PUBLICATIONS

Yang et al., Preparation of poly epsilon-caprolactone nanoparticles containing magnetite for magnetic drug carrier. 2006 Int. J. Pharm. 324: 185-190.
Raabe, J., et al., Magnetization pattern of ferromagnetic nanodisks, Journal of Applied Physics, 2000; 88 (7):4437-4439.
Korneva et al., Carbon nanotubes loaded with magnetic particles. 2005 Nano Lett. 5: 879-884.
Park, et al., Synthesis and magnetic studies of uniform iron nanorods and nanospheres. 2000 J. Am. Chem. Soc. 122: 8581-8582.
Corr et al., From nanocrystals to nanorods: new iron oxide-silica nanocomposites from metallorganic precursors. 2008 J. Phys. Chem. C 112: 1008-1018. Published online Jan. 9, 2008.
Bai et al, "Synthesis of Superparamagnetic Nanotubes as MRI Contrast Agents and for Cell Labeling", Nanomedicine, 2008, pp. 163-174, vol. 3, No. 2.
Lanza et al, "(1)H/(19)F Magnetic Resonance Molecular Imaging with Perfluorocarbon Nanoparticles", Current Topics in Developmental Biology, 2005, pp. 57-76; vol. 70, No. 1.
Seevinck et al, "Factors Affecting the Sensitivity and Detection Limits of MRI, CT, and SPECT for Multimodal Diagnostic and Therapeutic Agents", Anti-Cancer Agents in Medicinal Chemistry, 2007, pp. 317-334, vol. 7, No. 3.
Sitharaman et al, "Superparamagnetic Gadonanotubes are High-Performance MRI Contrast Agents", Chem. Commu., 2005, pp. 3915-3917, No. 31.
Sukstanskii et al, "Theory of FID NMR Signal Dephasing Induced by Mesocopic Magnetic Field Inhomogeneities in Biological Systems", Journal of Magnetic Resonance, 2001, pp. 107-117, vol. 151, No. 1.

(Continued)

*Primary Examiner* — Michael G. Hartley
*Assistant Examiner* — Jennifer Lamberski
(74) *Attorney, Agent, or Firm* — Polsinelli PC; Ron Galant

(57) ABSTRACT

The present invention relates to a magnetic resonance structure with a cavity or a reserved space that provides contrast and the additional ability to frequency-shift the spectral signature of the NMR-susceptible nuclei such as water protons by a discrete and controllable characteristic frequency shift that is unique to each MRS design. The invention also relates to nearly uniform solid magnetic resonance $T_2^*$ contrast agents that have a significantly higher magnetic moment compared to similarly-sized existing MRI contrast agents.

12 Claims, 47 Drawing Sheets

(56) References Cited

OTHER PUBLICATIONS

Woods et al, "Paramagnetic Lanthanide Complexes as PARACEST Agents for Medical Imaging", Chemical Society Reviews, 2006, pp. 500-511, vol. 35, No. 6.

Zabow et al, "Design and Fabrication of a Micromachined Multispectral Magnetic Resonance Imaging Agent", J. Micromech. Microeng., 2009, pp. 1-10, vol. 19, No. 2.

Zabow et al., "Micro-Engineered Local Field Control for High-Sensitivity Multispectral MRI", Nature, 2008, pp. 1058-1063, vol. 453, No. 7198.

* cited by examiner

FIG. 41A
FIG. 41B
FIG. 41C
FIG. 41D
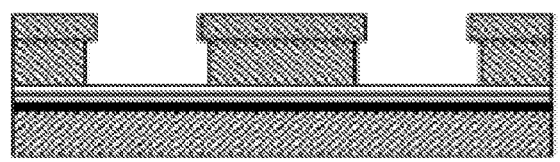
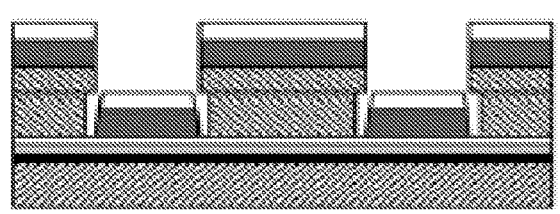
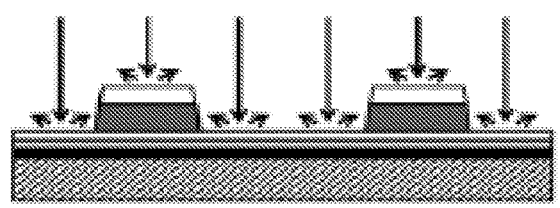

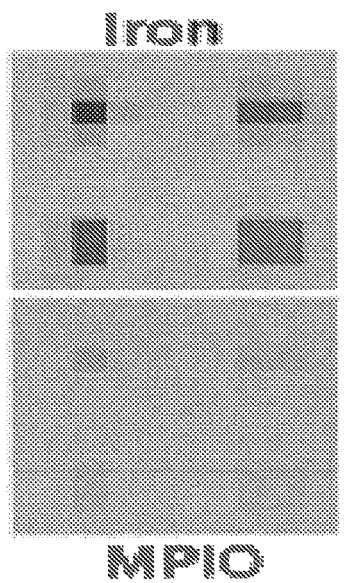
FIG. 47A
FIG. 47C
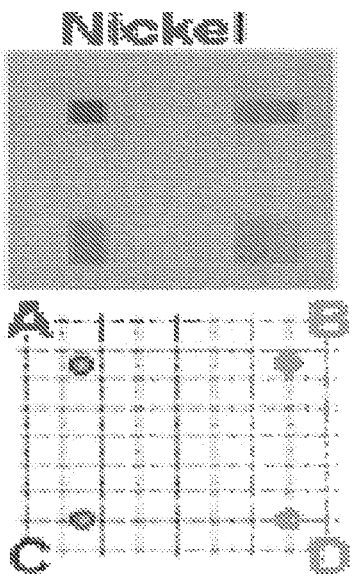
FIG. 47B
FIG. 47D

FIG. 48A  FIG. 48B  FIG. 48C
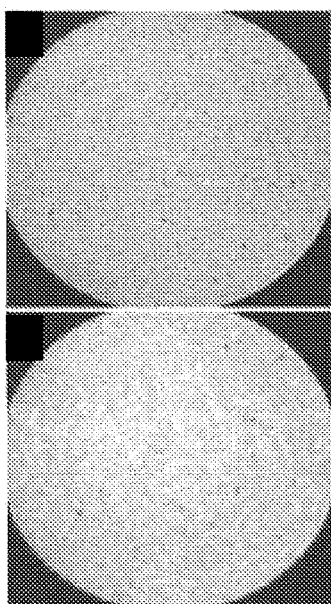 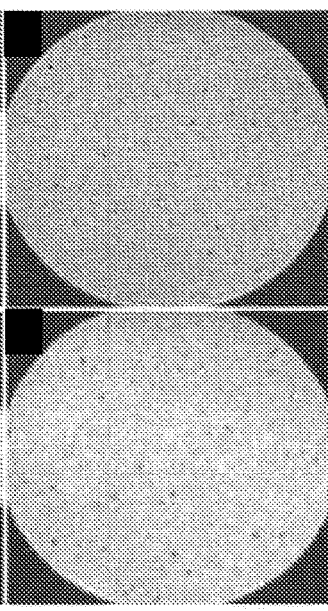 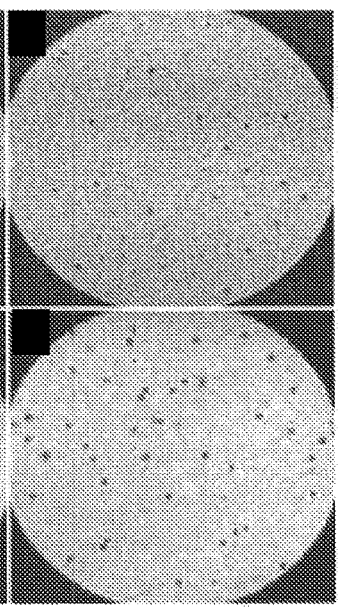
FIG. 48D  FIG. 48E  FIG. 48F

MAGNETIC MICROSTRUCTURES FOR MAGNETIC RESONANCE IMAGING

CROSS-REFERENCE TO RELATED APPLICATION

This is a continuation-in-part of International Application No. PCT/US2009/041142, filed on Apr. 20, 2009, which claims the benefit of U.S. Provisional Patent Application No. 61/071,263, filed Apr. 18, 2008, the contents of which are incorporated herein by reference. This also claims the benefit of U.S. Provisional Patent Application No. 61/166,610, filed Apr. 3, 2009, the contents of which are hereby incorporated by reference.

FIELD OF INVENTION

The present invention relates to magnetic resonance imaging contrast agents and methods of magnetic resonance imaging. In particular, the present invention relates to magnetic resonance structures used as magnetic resonance imaging contrast agents and multiplexed magnetic resonance imaging methods.

BACKGROUND

Biotechnology and biomedical research have benefited from the introduction of a variety of specialized nanoparticles whose well-defined, optically distinguishable signatures enable simultaneous tracking of numerous biological indicators. Optically based labels such as colored fluorophores, multi-spectral semiconductor quantum dots, and metallic nanoparticles can be used for multifunctional encoding, and biomolecular sensing and tracking. However, these optically based labels can probe only so far beneath most surfaces.

Contrast agents used in magnetic resonance may probe far below most tissue surfaces. Equivalent multiplexing capabilities are largely absent in the field of magnetic resonance imaging (MRI). MRI cell tracking is based on the magnetically dephased signal from the fluid surrounding cells labeled with many superparamagnetic iron oxide (SPIO) nanoparticles, or dendrimers, or individual micrometer-sized particles of iron oxide (MPIO). The continuous spatial decay of the external fields surrounding these magnetizable particles, or any other magnetizable particles, imposes a continuous range of Larmor frequencies that broadens the water hydrogen proton line, obscuring any distinction between different types of magnetic particles that might specifically label different types of cells and as a consequence provide only a monochrome contrast. Accordingly, there is a need in the art to distinguish with magnetic resonance (MR) between different cell types, at the single-cell level, for application in cellular biology, and early disease detection and diagnosis.

Alternatively, cellular tracking and labeling by strong magnetic resonance $T_2^*$ agents can also be used for labeling to provide a strong monochrome contrast to cellular components. $T_2^*$ contrast agents such as nanoscale superparamagnetic particles of iron oxide (SPIOs) and their micrometer-sized equivalents (MPIOs) can only be used in limited amounts in a cell without compromising its viability and therefore prevented in vivo tracking of single cells from becoming routine. Accordingly, there is a need in the art for an improved contrast agent.

SUMMARY OF THE INVENTION

The present invention is directed to a magnetic resonance contrast agent consisting essentially of a plurality of disks of uniform size and magnetic moment, wherein the disks consist essentially of a single magnetic material. Each disk may have magnetic moment from about $10^{-14}$ A·m² to about $10^{-11}$ A·m² and vary in size by less than about 5% of the average size of the plurality of disks. Each disk may also vary in magnetic moment by less than about 5% of the average magnetic moment of the plurality of disks. The magnetic material of the magnetic resonance contrast agent may comprise a ferromagnetic, paramagnetic, superparamagnetic, magnetic alloy, or a magnetic compound. The magnetic resonance contrast agent may further comprises a coating selected from an oxidation barrier, a corrosion barrier, a mechanical strengthening layer, a non-toxic coating, a biologically inert coating, a coating to facilitate common bioconjugation protocols, a cell-specific antibody or ligand coating, and combinations thereof. The magnetic resonance contrast agent may be a disk shape having a disk diameter ranging from about 0.5 µm to about 10 µm and a disk thickness ranging from about 0.5 µm to about 10 µm.

The present invention is also directed to a method of super-resolution tracking of a magnetic resonance visualization contrast agent consisting essentially of a plurality of disks, wherein the disks consist essentially of a single magnetic or paramagnetic material. The method may comprise (a) distributing the magnetic resonance visualization contrast agent within a sample such that each individual disk is spatially separated from all other disks; (b) performing magnetic resonance visualization of the sample to obtain an magnetic resonance visualization image comprising a plurality of voxels, wherein each voxel comprises a pixel, each pixel having a pixel intensity; (c) analyzing the magnetic resonance image to locate each pixel that is darker than a background pixel intensity resulting from a disk somewhere within a corresponding voxel, determining if any of the darkest voxels are situated in a contiguous group (d) determining the pixel intensity of the darkest voxel; assigning the location of the contrast agent to the darkest voxels in each contiguous group and (e) determining the location of each disk within its corresponding voxel by comparing the intensity of the voxel in each contiguous group to the intensity of the darkest voxel in the contiguous group.

The present invention is also directed to a method of non-invasively monitoring at least one characteristic of blood flow through a stent device situated within a blood vessel of a living subject. The method may comprise (a) providing a stent device comprising an MRS, wherein the MRS induces a known NMR shift in a NMR-susceptible nucleus when exposed to an excitatory electromagnetic pulse delivered at a corresponding resonance frequency; (b) situating the stent device within the blood vessel of the living subject; (b) exposing the stent device to at least one or more excitatory electromagnetic pulses delivered at the corresponding resonance frequency to create a volume of spin-labeled blood molecules; (c) obtaining nuclear magnetic resonance data of a volume of blood flowing downstream of the stent device; and, (d) analyzing the magnetic resonance image data to locate the volume of spin-labeled blood molecules using the known NMR shift. At least one characteristic of blood flow of the method may comprise mass flow rate, volume flow rate, and flow speed. In addition, the characteristic of blood flow may be compared to a baseline characteristic of blood flow to determine the presence or absence of occlusions within the stent device. The NMR shift of the spin-labeled blood molecules may be compared to a baseline NMR shift to determine if any deformation in the shape of the stent device has occurred and each different NMR shift is assigned a different color on a color scale.

The present invention may also be directed to an magnetic resonance contrast agent comprising a magnetic material forming a reserved space that is connected to a near-field volume, wherein the magnetic material produces a substantially uniform magnetic field within the reserved space, and wherein the uniform magnetic field has a magnitude that is substantially different than a background magnetic field within the near-field volume.

The present invention may also be directed to a method of using two or more MRS, wherein each MRS induces a known NMR shift in a NMR-susceptible nucleus when exposed to an excitatory electromagnetic pulse delivered at a corresponding resonance frequency, wherein each of the known NMR shifts, and each of the corresponding resonance frequencies are different for each of the two or more MRS. The method may comprise (a) distributing the two or more MRS within a sample; (b) exposing the two or more MRS within the sample to excitatory electromagnetic pulses delivered at each of the two or more corresponding resonance frequencies; (c) obtaining nuclear magnetic resonance data after each excitatory electromagnetic pulse; and, (d) using the known NMR shifts to determine the identity of each of the two or more MRS. Each particular MRS of the method may be targeted toward a particular tissue or cell. The MRS targeted to a particular cell may be bound to the cell at a cell wall or cell membrane.

BRIEF DESCRIPTION OF THE DRAWINGS

Additional features of this invention are provided in the following detailed description of various embodiments of the invention with reference to the drawings. Furthermore, the above-discussed and other attendant advantages of the present invention will become better understood by reference to the detailed description when taken in conjunction with the accompanying drawings, in which:

FIG. 17A is a magnified view of the array shown in FIG. 17C.

FIG. 21A is a drawing showing cylindrical photoresist posts atop a gold-titanium coated substrate.

FIG. 21B is a drawing of angled copper evaporation onto the cylindrical photoresist.

FIG. 21C is a drawing showing magnetic material evaporation.

FIG. 21D is a drawing showing ion-milling removal of magnetic material and local resputtered coating of the photoresist posts.

FIG. 21E is a drawing showing copper and photoresist removal.

FIG. 21F is a drawing showing the release of hollow cylinders magnetic resonance structures by gold-etch or ultrasound techniques.

FIG. 23E is an MRI image of an array of hollow cylinder magnetic resonance structure in which a subset of the hollow cylinders is filled in.

FIGS. 41A-41D are a drawings illustrating an embodiment of a fabrication method for a solid high magnetic moment $T_2^*$ contrast agent.

FIG. 46A is a simulated gradient echo MRI images taken using 50-μm isotropic resolution and a magnetic field $B_0$ oriented parallel to the MRI image slices.

FIG. 46B is a simulated gradient echo MRI images taken using 100-μm diameter contrast agent particles using a magnetic field $B_0$ oriented parallel to the MRI image slices.

FIG. 46C is a simulated gradient echo MRI images taken using 50-μm isotropic resolution and a magnetic field $B_0$ oriented perpendicular to the MRI image slices.

FIG. 46D is a simulated gradient echo MRI images taken using 100-μm isotropic resolution and a magnetic field $B_0$ oriented perpendicular to the MRI image slices.

FIGS. 47A-47C are theoretical magnetic resonance images of single contrast agent particles comparing the signal intensities of the particles at different positions within the cubic voxels.

FIG. 47A shows the effect of position within the voxel on the signal intensity predicted for iron contrast agent particles.

FIG. 47B shows the effect of position within the voxel on the signal intensity predicted for nickel contrast agent particles.

FIG. 47C shows the effect of position within the voxel on the signal intensity predicted for iron oxide contrast agent particles.

FIG. 47D shows the positions of the contrast agent particles within the voxel boundaries simulated in FIGS. 47A-47C.

FIGS. 48A-48F are gradient-echo MRI images of chemically synthesized and mirofabricated magnetic resonance contrast agents.

FIG. 48A is a gradient-echo MRI image using 50-μm isotropic resolution of a prior art MPIO contrast particle.

FIG. 48B is a gradient-echo MRI image using 50-μm isotropic resolution of a microfabricated solid nickel contrast particle.

FIG. 48C is a gradient-echo MRI image using 50-μm isotropic resolution of a microfabricated solid iron contrast particle.

FIG. 48D is a gradient-echo MRI image using 100-μm isotropic resolution of a prior art MPIO contrast particle.

FIG. 48E is a gradient-echo MRI image using 100-μm isotropic resolution of a microfabricated solid nickel contrast particle.

FIG. 48F is a gradient-echo MRI image using 100-μm isotropic resolution of a microfabricated solid iron particle.

FIG. 49A is a histogram of theoretical single voxel signal intensity for a microfabricated iron contrast agent normalized to the background signal intensity.

FIG. 49B is a histogram of the experimentally-measured single voxel signal intensity for a microfabricated iron contrast agent normalized to the background signal intensity.

FIG. 49C is a histogram of theoretical single voxel signal intensity for a microfabricated nickel contrast agent normalized to the background signal intensity.

FIG. 49D is a histogram of the experimentally-measured single voxel signal intensity for a microfabricated nickel contrast agent normalized to the background signal intensity.

FIG. 49E is a histogram of theoretical single voxel signal intensity for a MPIO contrast agent normalized to the background signal intensity.

FIG. 49F is a histogram of the experimentally-measured single voxel signal intensity for a MPIO contrast agent normalized to the background signal intensity.

FIG. 50A is a graph showing the fractional hypointensity $(1-S/S_0)$ as a function of dipole moment for a 50-μm isotropic resolution and an echo time of 5-ms.

FIG. 50B is a graph showing the fractional hypointensity $(1-S/S_0)$ as a function of dipole moment for a 100-μm isotropic resolution and an echo time of 5-ms.

FIG. 50C is a graph showing the fractional hypointensity $(1-S/S_0)$ as a function of dipole moment for a 50-μm isotropic resolution and an echo time of 10-ms.

FIG. 50D is a graph showing the fractional hypointensity $(1-S/S_0)$ as a function of dipole moment for a 100-μm isotropic resolution and an echo time of 10-ms.

FIG. 50E is a graph showing the fractional hypointensity $(1-S/S_0)$ as a function of dipole moment for a 50-μm isotropic resolution and an echo time of 20-ms.

FIG. 50F is a graph showing the fractional hypointensity $(1-S/S_0)$ as a function of dipole moment for a 100-μm isotropic resolution and an echo time of 20-ms.

DETAILED DESCRIPTION

Figure 1:
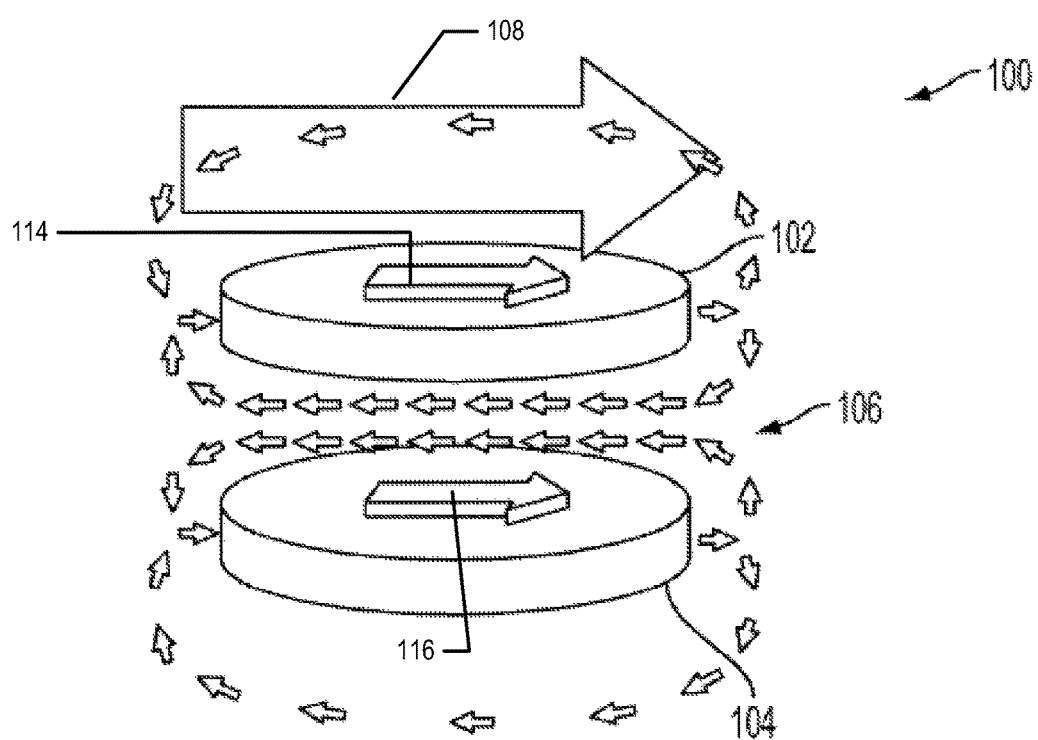
FIG. 1 is an illustration of an embodiment of a dual-disk magnetic resonance structure.

The inventors have designed a magnetic resonance structure (MRS) with a cavity or reserved space that provides contrast and the additional ability to frequency-shift the spectral signature of the NMR-susceptible nuclei such as water protons by a discrete and controllable characteristic frequency shift that is unique to each MRS design. The frequency-shifted spectral signature, which may be engineered by controlling the precise geometry of the MRS, may be used in addition to contrast to provide for identifying individual MRS's in magnetic resonance (MR) image data or in any other nuclear magnetic resonance system data, and for distinguishing different MRS types/geometries from one another within these data. The individual magnitudes of frequency-shifting resulting from individual MRS may be associated with an individual color on a color map of the spectral signatures acquired from each location or from each MRS within an MR image, greatly enhancing the informational content of MR images. Using the MRS as contrast agents in MR imaging, the resulting MR imaging data may provide a color map of the spectral signature shifts, which provides additional information regarding the identities of individual MRS, in addition to the contrast signals produced by the MRS.

In the reserved space or cavity of the MRS a substantially, spatially uniform magnetic field is generated whose strength is significantly different from that of the background field outside the particle. The reserved space or cavity allows NMR-susceptible nuclei such as water protons to diffuse or flow in and out of the reserved space thereby increasing the volume of fluid frequency-shifted during the repeated application of resonant electromagnetic pulses. This diffusion modulates the signal from a volume of fluid many times greater than the volume contained in the MRS, and this enhancement allows a lower-density of particles to be used in order to produce the contrast, in addition to the color information.

This frequency-shifting signal is produced by the MRS only if the MRS is exposed to a electromagnetic pulse at a specific resonant frequency that is precisely specified by the particular design of the MRS. If the same MRS is exposed to a RF pulse with a frequency that is significantly different from the resonance frequency of the MRS, no signal will be produced. Individual MRS within an ensemble of MRS in a sample, each having a different resonance frequency, may produce a frequency-shifting signal when exposed to an RF pulse at its characteristic resonance frequency with no signal production by the other MRS having different resonant frequencies in the ensemble.

A group of essentially identical MRS particles having a reserved space and being essentially uniform in size and composition may thus shift the frequency spectra of NMR-susceptible nuclei by the same discrete and controllable amount during exposure to resonant electromagnetic pulse. Different groups of MRS particles constructed to shift the frequency spectra of NMR-susceptible nuclei by different discrete and controllable amounts may be used to perform multiplexed magnetic resonance scanning in which the different frequency spectrum shifts of the different MRS particles may be encoded as different colors in the resulting magnetic resonance image. The MRS may be produced using a technique that results in an essentially uniform size and composition of a plurality of MRS. The combination of creating a reserved space with an essentially uniform magnetic field and a substantially pure composition both in material, shape, and size, allow use of a relatively low detectable concentration of a magnetic resonance contrast agent in a magnetic resonance scan as compared to the amount of the MRI contrast agent required in the prior art.

In addition to MRS structures that provide data that may be used for color mapping, the inventors have also created nearly uniform solid magnetic resonance $T_2^*$ contrast agents that have a significantly higher magnetic moment compared to similarly-sized existing MRI contrast agents. Top-down fabrication method may be used to produce these solid MRS contrast agents from virtually any material, including materials with a high saturation magnetic density such as nickel or soft iron. As a result, the external magnetic fields produced by the solid MRS particles are significantly stronger than the corresponding fields produced by existing MRI contrast agents such as superparamagnetic iron oxide nanoparticles (SPIO). In fact, these solid magnetic resonance contrast agents increase visibility several-fold extending its applications to areas such as in vivo single-cell tracking studies. In addition, both MRS with a cavity/reserved space and the solid particulate MRS, are dimensionally consistent from particle to particle facilitating more quantitative image analysis and making possible super-resolution tracking or locating of the position of an individual MRS within a voxel using both the absolute value of the contrast signal and the relative contrast intensities from surrounding voxels. Thus, all MRS designs may be used as conventional $T_2^*$ magnetic resonance contrast agents with significantly improved efficacy relative to other $T_2^*$ contrast agents. The substantial uniform dimensions of these compositions also allow use of minimal detectable concentrations in comparison to the solid magnetic resonance contrast agents required in the prior art.

The ability to microfabricate both an MRS with a reserved space and a solid MRS from a variety of different, and highly magnetic materials provides great advantages because many of the paramagnetic materials currently used for MRI contrast agents (for example, Gadolinium complexes) are considered potentially toxic at some threshold amount. The MRS may be used in a number of applications including magnetic resonance frequency shifts of water protons and other NMR-susceptible nuclei for magnetic resonance calibration/testing/fabrication, magnetic resonance spatial calibration markers, specific detection/labeling/tracking of biological cells, distance/pressure/vibration/torque sensors, torque/orientational measurements, magnetic separation, fluid pumps or mixers, localized RF magnetic heating elements, localized magnetic field gradients, microfluidic applications, flow cytometry, flow sensors for stents, and single cell characterization.

A detailed description of embodiments of the MRS, methods of producing an MRS, and methods of using the MRS is provided below.

1. Definitions

The terminology used herein is for the purpose of describing particular embodiments only and is not intended to be limiting. As used in the specification and the appended claims, the singular forms "a," "an" and "the" include plural referents unless the context clearly dictates otherwise.

For recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the numbers 6.0, 6.1, 6.2, 6.3, 6.4, 6.5, 6.6, 6.7, 6.8, 6.9, and 7.0 are explicitly contemplated.

a. $B_0$ Magnetic Field

As used herein, a $B_0$ magnetic field may be a uniform external applied magnetic field that possesses a uniform magnitude and uniform direction in the absence of any MRS or other magnetic particles. The $B_0$ magnetic field may also be referred to as a background magnetic field. In certain applications, the $B_0$ magnetic field may be produced by a magnetic resonance visualization device such as an MRI scanner.

b. Far-Field Volume

As used herein, the far-field volume may be the region outside the near-field volume of a MRS that encompasses the far-field magnetic field induced by the MRS structure.

c. Near-Field Volume

As used herein, the near-field volume may be a volume that is essentially centered on a MRS and extends out from the structure to a distance of no more than a few times the maximum spatial dimension of the MRS itself. The extent of this near-field volume may scale with the size of the MRS.

d. Non-Magnetic Material

As used herein, a nonmagnetic material may be a material that does not exhibit a substantial magnetic field either intrinsically or when placed in a magnetizing field. Although nonmagnetic materials are distinguished from ferromagnetic materials and superparamagnetic materials, nonmagnetic materials may not necessarily be completely nonmagnetic in nature, but may include materials that are weakly magnetic, very weakly paramagnetic or diamagnetic in nature. For example, the water that is commonly detected and imaged in magnetic resonance systems is detected because of the nuclear magnetic resonance of the water. Because the magnetism of the water is extremely weak relative to the magnetic materials described herein, however, water and the other weakly magnetic materials described herein may be regarded as nonmagnetic materials.

2. Magnetic Resonance Structures

Provided herein is a magnetic resonance structure (MRS).

a. Solid High Magnetic Moment $T_2^*$ Contrast Agents (Solid Particulate MRS)

The MRS may be a solid particle. The solid particulate MRS may be high magnetic moment particles for high-resolution imaging in which individual particles may be located and tracked with greater precision for quantitative analysis. The solid particular MRS may share uniformity from one particle to the next. The solid particular MRS may have a high magnetic moment because each particle uses substantially pure, strongly magnetic material. The solid particular MRS has these characteristics because it is generated through top-down fabrication as discussed below.

The solid particulate MRS also may share uniformity in shape from one particle to the next. The minimum detectable concentration of the solid particulate MRS when used as a magnetic resonance agent may be as low as an individual solid particulate MRS. The solid particulate MRS may be in the form of a disk, a cylinder, a pyramid, a cube, a sphere, a rectangular block, a rod, a square, a crescent or any shape permutation thereof. The solid particulate MRS may have a uniform shape and surface or may have an uneven surface with protractions from the layer.

The solid particulate MRS may be a $T_2^*$ contrast agent. The high magnetic moment of the solid particulate MRS may result in a stronger transverse dephasing of the water protons around the particle, thus inducing a significantly higher $T_2^*$ contrast relative to existing magnetic particle $T_2^*$ contrast agents such as MPIOs of similar size.

Further, the solid particulate MRS may have a very low variability in the size of the particles or the composition of the material making up the particle. The size of each individual particles may vary by less than 10%, less than 9%, less than 8%, less than 7%, less than 6%, less than 5%, less than 4%, less than 3%, less than 2%, and less than 1% of the mean size of the particles. As a result, the solid particulate MRS may be used in an advanced magnetic resonance visualization technique such as super-resolution tracking to a much greater precision for quantitative analysis.

The overall volume of a solid particulate MRS may range from about $5 \times 10^{-22}$ m$^3$ to about $5 \times 10^{-15}$ m$^3$, or $5 \times 10^{-22}$ m$^3$, $5 \times 10^{-21}$ m$^3$, $5 \times 10^{-20}$ m$^3$, $5 \times 10^{-19}$ m$^3$, $5 \times 10^{-18}$ m$^3$, $5 \times 10^{-17}$ m$^3$, $5 \times 10^{-16}$ m$^3$, or $5 \times 10^{-15}$ m$^3$. The overall volume of each solid particulate MRS of a group having a particular specified size may be consistently the same within about 0.1%, about 0.5%, 1.0%, 2.0%, 3.0%, 4.0%, 5.0%, 6.0%, 7.0%, 8.0%, 9.0%, or 10% of the mean volume In addition, the magnetic moment of the solid particular MRS may be about $10^{-15}$ Am$^2$, $10^{-14}$ Am$^2$, $10^{-13}$ Am$^2$, $10^{-12}$ Am$^2$, $10^{-11}$ Am$^2$, or $10^{-10}$ Am$^2$. Further, the variation in magnetic moment within a group having a particular specified magnetic moment may be within about 0.1%, about 0.5%, 1.0%, 2.0%, 3.0%, 4.0%, 5.0%, 6.0%, 7.0%, 8.0%, 9.0%, or 10% of the mean magnetic moment. The $J_s$ values of the solid particulate MRS may be 0.0 T, 0.1 T, 0.2 T, 0.3 T, 0.4 T, 0.5 T, 0.6 T, 0.7 T, 0.8 T, 0.9 T, 1.0 T, 1.1 T, 1.2 T, 1.3 T, 1.4 T, 1.5 T, 1.6 T, 1.7 T, 1.8 T, 1.9 T, 2.0 T, 2.1 T, 2.2 T, 2.3 T, 2.4 T, or 2.5 T.

If the solid particulate MRS is a solid disk, the overall diameter of the solid disk MRS may range from about 0.5 μm to about 20 μm, or about 0.5 μm, 1.0 μm, 2.0 μm, 3.0 μm, 4.0 μm, 5.0 μm, 6.0 μm, 7.0 μm, 8.0 μm, 9.0 μm, 10.0 μm, 11.0 μm, 12.0 μm, 13.0 μm, 14.0 μm, 15.0 μm, 16.0 μm, 17.0 μm, 18.0 μm, 19.0 μm, or 20.0 μm. The overall thickness of the solid disk MRS may range from about 0.5 μm to about 20 μm, or about 0.5 μm, 1.0 μm, 2.0 μm, 3.0 μm, 4.0 μm, 5.0 μm, 6.0 μm, 7.0 μm, 8.0 μm, 9.0 μm, 10.0 μm, 11.0 μm, 12.0 μm, 13.0 μm, 14.0 μm, 15.0 μm, 16.0 μm, 17.0 μm, 18.0 μm, 19.0 μm, or 20.0 μm.

The solid particulate MRS may be composed of a non-magnetic layer and/or a magnetic layer or combinations thereof. The thickness of each layer may vary between 1-nm to 1000-nm in thickness or 1-nm, 10-nm, 20-nm, 30-nm, 40-nm, 50-nm, 60-nm, 70-nm, 80-nm, 90-nm, 100-nm, 150-nm, 200-nm, 250-nm, 300-nm, 350-nm, 400-nm, 450-nm, 500-nm, 550-nm, 600-nm, 650-nm, 700-nm, 750-nm, 800-nm, 850-nm, 900-nm, 950-nm, 1000-nm, 1 μm, 2 μm, 3 μm, 4 μm, 5 μm, 6 μm, 7 μm, 8 μm, 9 μm, 10 μm, 11 μm, 12 μm, 13 μm, 14 μm, 15 μm, 16 μm, 17 μm, 18 μm, 19 μm, or 20 μm. The magnetic material of the solid particulate MRS may be iron, nickel, chromium, manganese, cobalt, or any magnetic alloy such as permalloy, neodymium alloy, alnico, bismanol, cunife, fernico, heusler alloy, mkm steel, metglas, samarium-cobalt, sendust, or supermalloy. The non-magnetic materials that may be used as coatings or to provide cohesion between layers of the magnetic materials may be gold, titanium, zinc, silver, tin, aluminum, or any other material that does not generate a magnetic field. The substrate layer used to generate the solid particulate MRS may be silicon, glass, quartz, sapphire, amorphous silicon dioxide, borosilicate or any other inert substance. The photoresistant material used to generate the solid particulate MRS may be positive/negative photoresistant material such as a polymethylmethacrylate, polymethylglutarimide, polymers, epoxy-based compounds such as SU-8, and phenol formaldehyde resins such as a mixture of diazonaphthoquinone (DNQ) and novolac resin.

Figure 40:
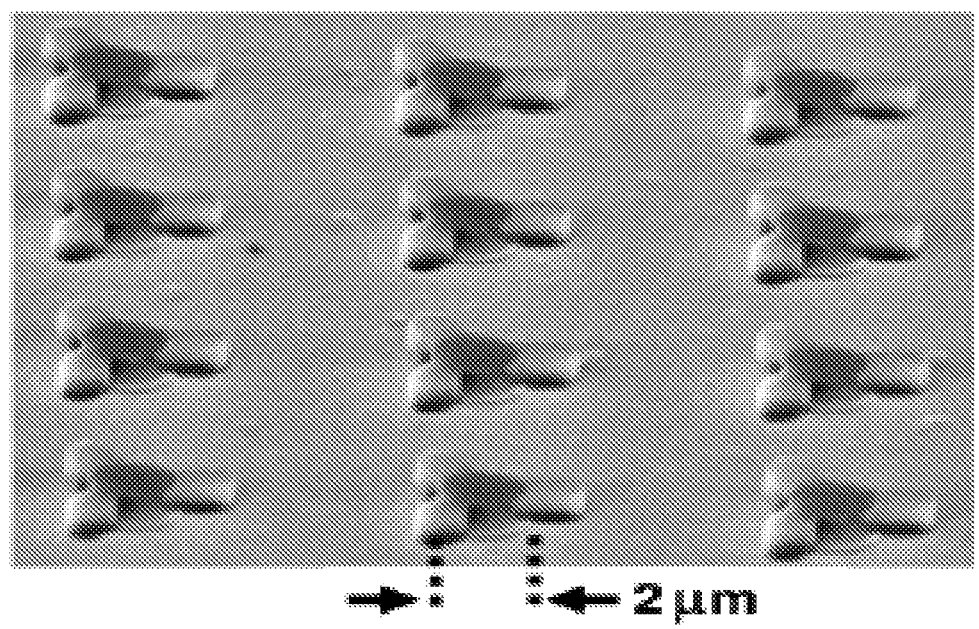
FIG. 40 is a scanning electron micrograph comparing the sizes of each disk in a dual-disk pair resulting from an embodiment of a fabrication process for a dual-disk magnetic resonance structure.
Figure 42A:
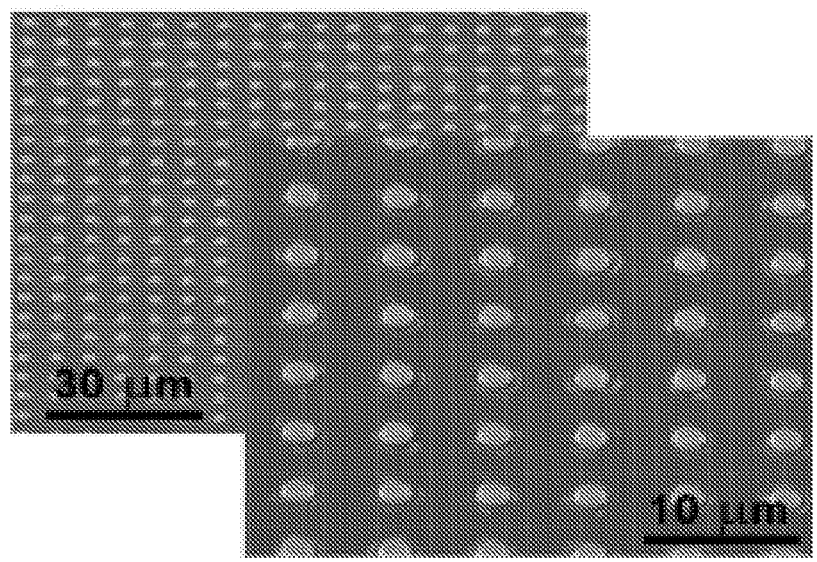
FIGS. 42A-42B are scanning electron micrographs showing an embodiment of a solid high magnetic moment $T_2^*$ contrast agent.
Figure 42B:
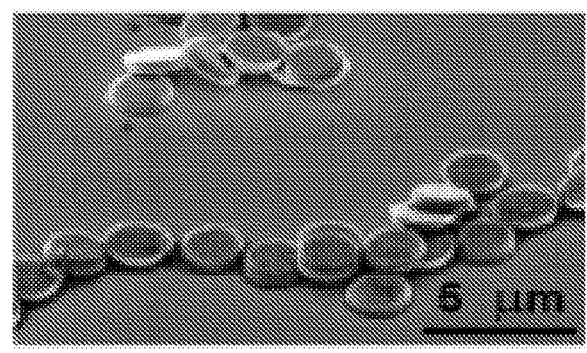

The solid particulate MRS may be in any form and any consistency of the various substrates, photoresistant materials, and magnetic materials due to the photolithographic patterning microfabrication techniques discussed below that allow arrays of many millions of solid particulate MRS that can be simultaneously fabricated. An exemplary solid particulate MRS is shown in FIG. 40. The solid particulate MRS has a 10-nm thick titanium adhesion layer that was evaporated onto a supporting substrate made be silicon, glass, quartz, sapphire, amorphous silicon dioxide, borosilicate or any other inert substance. A 100-nm layer of copper is laid over the titanium layer. Blocks of 300-nm thick layer of iron or nickel surrounded by a 100-nm gold layer are laid across the copper layer through a bi-layer lift off process described below. Back-sputtered gold ion-milled from the substrate redeposits on the iron/nickel sidewalls encase the entire solid particulate MRS of FIG. 41 leaving 100-nm thick top and bottom gold coatings and 50-nm thick gold coatings along the circumferential sidewall of the MRS particle of FIG. 41. FIG. 42 is a series of SEM images showing the resulting solid particulate MRS.

b. MRS Contrast Agent with a Reserved Space

The MRS may comprise a reserved space. The reserved space may be situated within the interior of the magnetic material or magnetic portions of the MRS so as to be at least partially surrounded by the magnetic material or magnetic portions. The near-field volume may comprise the reserved space. The size of the reserved space may be dependent on the overall size and arrangement of the magnetic materials in the MRS. The reserved space may be in the form of a disk shape, a tubular shape, a spherical shape, or any other geometrical volume so long as the magnetic field formed within the reserved space is an essentially uniform magnetic field.

The MRS may form at least one opening that permits fluid in the near-field volume to enter and exit the reserved space by diffusion, convection, or directional flow. The reserved space may be the main region in which the frequency-shifting of water protons and other NMR susceptible nuclei occurs. The reserved space may be filled by a non-magnetic fluid.

The magnitude of the frequency shift may be precisely controlled through variations in the magnetic strength of magnetic materials used to construct the MRS as well as the relative proportions of the dimensions of the MRS. In general, the magnitude of the frequency shift $\Delta\omega$ may be expressed as:

$$\Delta\omega = (\gamma J_s/2) \cdot G \qquad (0)$$

where $\gamma$ is the gyromagnetic ratio, $J_s$ is the saturation magnetic polarization, and G is a dimensionless ratio of at least two linear dimensions that define the geometry of the MRS. The gyromagnetic ratio and saturation magnetic polarization depend on the NMR-susceptible nuclei to be frequency-shifted and the choice of magnetic material in the MRS, respectively. The linear dimensions that define the geometry of the MRS are specified by the particular MRS structure and may include dimensions such as length, diameter, wall thickness, and others. The particular combination of dimensions that make up G vary between MRS with different geometries. For example, for a dual-disc MRS, described in detail below:

$$G=[(S-h/2)((S-h/2)^2+R^2)^{1/2}-(S+h/2)((S+h/2)^2+R^2)^{1/2}] \quad (0.1)$$

where h is the disk thickness, R is the disk radius, and 2S is the center-to-center disk separation.

If the MRS structure is a hollow cylinder, also described in detail below:

$$G=L\cdot[(L^2+(2\rho+t)^2)^{-1/2}-(L^2+(2\rho-t)^2)^{-1/2}] \quad (0.2)$$

where t is the cylinder wall thickness, $2\rho$ is the cylinder diameter, and L is the length of the cylinder.

For MRS with other structural geometries, similar dimensionless ratios G may be derived using magnetostatic theory. However, because G is a dimensionless ratio of at least two or more dimensions, the value of G is independent of the overall size of the MRS structure. Depending on the particular dimensions and structure of the MRS, G may vary between about 0.1 and about 2. In various embodiments, G may be about 0.0001, 0.0005, 0.0006, 0.0007, 0.0008, 0.0009, 0.001, 0.005, 0.01, 0.02, 0.03. 0.04, 0.05, 0.06, 0.07, 0.08, 0.09, 0.10, 0.11, 0.12, 0.13, 0.14, 0.15, 0.16, 0.17, 0.18, 0.19, 0.2, 0.3, 0.4, 0.5, 0.6, 0.7, 0.8, 0.9, 1.0, or 2.0.

(1) Essentially Uniform Magnetic Field

The magnetic material of the MRS with a reserved space may produce a magnetic field throughout the near-field volume and far-field region. An essentially uniform magnetic field may be produced in the reserved space inside the near-field volume, and a spatially decaying magnetic field may be produced in the volume external to the MRS.

The sharpness and signal strength of the frequency-shifting signal produced by the MRS depends most directly on the characteristics of the essentially uniform magnetic field within the reserved space of the MRS. In order to induce a detectably distinct characteristic Larmor frequency in any NMR-susceptible material, such as water protons passing through the essentially uniform magnetic field, the magnitude of the essentially uniform magnetic field must be sufficiently different from the surrounding magnetizing field. The magnitude of the essentially uniform magnetic field may be specified by the selection of magnetic materials and arrangement of the magnetic materials in the MRS.

The magnetic material of the MRS may be selected to have a particular saturated magnetic polarization ($J_s$), resulting in an essentially uniform magnetic field within the reserved space (MRS field+background field) that is different in magnitude from the background field magnitude, particularly when the magnetic material is magnetically fully saturated. However, even when the magnetic material is only partially magnetized, the essentially uniform magnetic field may be sufficiently different from the background field if the magnetic material has a sufficiently high $J_s$. Typically, the magnetic materials of the MRS will reach fully saturated magnetization within typical background MR fields. The detectable Larmor frequencies induced by the MRS may be relatively insensitive to the magnitude of the applied magnetic field of different magnetic resonance devices if the magnetic moment or moments of the MRS are fully saturated by background MR fields.

Alternatively, if the magnetic material selected for the MRS is a permanent magnetic material such as magnetite, the essentially uniform magnetic field within the reserved space may be significantly different from the background magnetic field even at relatively low (or zero) background magnetic field magnitudes because the MRS generates a magnetic field independently of the background magnetic field.

The magnetic field may be a local region of interest within the near-field region of the MRS. This region may be where the total magnetic field is substantially uniform and substantially different in magnitude from any background magnetic field. The region of interest in which the essentially uniform magnetic field is induced by the MRS may not be confined to be within the reserved space extending in a region outside of the reserved space, but within the near-field region. Alternatively, the essentially uniform magnetic field may not extend through the entire reserved space.

The material to which the essentially uniform magnetic field induces a characteristic Larmor frequency may be any material containing nuclei known in the art to be susceptible to nuclear magnetic resonance due to the nuclei containing an odd number of protons or neutrons. Non-limiting examples of nuclei susceptible to NMR include $^1H$, $^2H$, $^3H$, $^{13}C$, $^{10}B$, $^{11}B$, $^{14}N$, $^{15}N$, $^{17}O$, $^{19}F$, $^{23}Na$, $^{29}Si$, $^{31}P$, $^{35}Cl$, $^{113}Cd$, $^{129}Xe$, and $^{195}Pt$. The material to which the essentially uniform magnetic field induces a characteristic Larmor frequency may be water containing $^1H$ protons.

(2) Principle of Operation

The MRS includes a near-field region in which an essentially uniform magnetic field significantly alters the resonant Larmor frequency of the water protons or other NMR-susceptible nuceli within the near-field region during exposure of the MRS to a resonant electromagnetic pulse. Magnetic resonance contrast is achieved by measuring the frequency shift of the near-field water protons and other NMR-susceptible nuclei affected by the MRS magnetic field during the resonant pulse.

In general, magnetic resonance visualization techniques are based on processing an electromagnetic signal originating from water protons or other NMR-susceptible nuclei exposed to an applied magnetic field. In general, the Larmor precession frequency w of a proton is induced to a value that is directly proportional to a local magnetic field magnitude $B_0$ according, as given in Eqn. (1):

$$\omega = -\gamma B_0 \quad (1)$$

where $\gamma$ is the gyromagnetic ratio. The local magnetic field is typically dominated by the magnetic field applied by the magnetic resonance scanning device. Many existing MRI contrast agents, however, make use of magnetic particles such as MPIOs to locally distort the applied magnetic field of the magnetic resonance device to enhance the contrast of the resulting image in a local region surrounding the contrast agent.

A magnetic object induces a magnetic field that continuously decays in magnitude as a function of the distance from the magnetic object within a relatively extended far-field volume surrounding the magnetic object. In the vicinity of any magnetic structure, proton precession frequencies vary proportionally to the spatially varying magnetic fields produced by that structure. Accordingly, NMR spectra integrating over NMR-susceptible proton signals from around that structure would typically integrate over broad frequency ranges, leading to broadened NMR spectral peaks.

Existing MRI contrast agents that include magnetic particles such as microparticles of iron oxide (MPIOs) generate magnetic resonance contrast by locally altering the longitudinal ($T_1$) or transverse ($T_2$ or $T_2^*$) relaxation rates using these far-field effects. Because the far-field effects of these existing MRI contrast agents involve non-homogeneous magnetic fields, however, no consistent and well-defined, quantized, and discrete color shift in the Larmor frequency of the water protons and other NMR-susceptible nuclei within the far-field region may be obtained using these existing MRI contrast agents in the prior art.

To yield instead a distinct frequency-shifted color NMR peak, the magnetic structure geometry of the MRS may be such that it produces a fluid-accessible, extended spatial volume over which the combined magnetic field from the field of the MRS, together with the applied magnetizing background magnetic resonance field $B_0$, is homogeneous and distinct in magnitude from the surrounding magnetic fields. By contrast, the various embodiments of the MRS function as multispectral contrast agents by shifting the resonant Larmor precession frequencies of the water protons and other NMR-susceptible nuclei in a discrete and controllable manner when the MRS is exposed to a resonant electromagnetic pulse.

The MRS described herein may shift the NMR spectra of NMR-susceptible nuclei such as water protons contained within a reserved space within the near-field region of the MRS during exposure to a resonant electromagnetic pulse. For example, the reserved space may be within a magnetizable shell or between neighboring magnetizable elements. Within the reserved space, the MRS may function as a specialized local magnetic field shifter.

The MRS may consist of specially shaped magnetizable elements, which are exemplified by 102 and 194 in FIG. 1. Once magnetized to saturation by the background magnetic field $B_0$ (typically at least a few Tesla in magnitude), the specially shaped magnetizable elements may generate localized regions of spatially homogeneous magnetic fields within a reserved space, which are exemplified by 110 in FIG. 1. The spatially homogeneous magnetic fields may have a magnitude substantially different from that of any surrounding magnetic fields. Hydrogen protons in the water molecules or other NMR-susceptible nuclei present in these localized homogeneous magnetic field regions may experience a shift in Larmor precession frequency when the MRS is exposed to a resonant electromagnetic pulse, and the presence of the magnetic resonance structure may be inferred via detection of these frequency-shifted NMR spectra. Signals originating from one particular type of the MRS may be differentiated from other types of MRS by using a type of MRS that induces discrete and controllable Larmor precession frequencies during resonant electromagnetic pulse that are detectably different from the Larmor precession frequencies induced by the background magnetic resonance magnetic field and the local magnetic field of the other types of MRS during electromagnetic pulses at their respective resonant frequencies.

The spatial profile and homogeneity of the local magnetic field within the reserved space may be accurately specified and controlled by the selection of magnetic materials and the size, shape and arrangement of the magnetic materials of the MRS. The degree of homogeneity of the local magnetic field of the MRS directly influences the sharp definition of the resulting shifted nuclear magnetic resonance (NMR) peaks. The spatial extent of the homogeneous magnetic field directly influences the magnitude of the resulting shifted color nuclear magnetic resonance (NMR) peaks. Although the spatial extent of the homogeneous magnetic field is proportional to the physical sizes of the magnetizable elements of the MRS, the same is not true for the amount of water protons and other NMR-susceptible nuclei that may contribute to the frequency-shifted signal, due to the additional effect of diffusion.

(3) Effect of Diffusion

The diffusion of fluid into and out of the reserved space within the near-field region effectively increases the volume of frequency-shifted water protons or other NMR-susceptible nuclei by increasing the overall number of water protons or other NMR-susceptible nuclei influenced by the magnetic field within the reserved space. The diffusion effect significantly increases the contrast signal strength produced by MRS relative to a similarly-sized volume of fluid.

In the MRS, the number of water protons or other NMR nuclei that are exposed to the homogeneous field regions within each reserved space is enhanced by the continual random self-diffusion of fluid containing NMR-susceptible nuclei in and out of each reserved space. The enhanced magnitude of the shifted nuclear magnetic resonance (NMR) peaks due to these diffusion effects may benefit the MRS regardless of size, and may especially benefit from a micrometer or smaller sized MRS.

In the absence of diffusion effects, the effective time for the replacement of frequency-shifted water protons and other NMR-susceptible nuclei within the near-field region of a magnetic contrast particle is limited to a length of time on the order of the longitudinal relaxation time, $T_1$ (2-3 sec.). The refresh time ($\tau_d$) for self-diffusion to refresh the fluid within a reserved space of a magnetic resonance structure scales with the square of the structure's external dimension ($R^2$). As the size of the MRS is reduced, the saturated magnetization of NMR-susceptible nuclei falls only linearly with R, rather than in proportion to the structure's volume ($R^3$). Using the diffusivity of water ($2.3 \times 10^{-9}$ ms$^{-2}$), the distance diffused during the time $T_1$ ($(6D \cdot T_1)^{1/2}$) is about 0.2 mm. Therefore, if the MRS is smaller than about 0.2 mm, the diffusivity effect enhances the magnitude of the saturated magnetization of NMR-susceptible nuclei.

Although diffusion is one mechanism by which water or other NMR-susceptible nuclei may move in and out of the reserved space resulting in enhancement of the frequency-shift signal, NMR-susceptible nuclei may move in and out of the reserved space due to other mechanisms including convection due to the flow of fluid in and out of the reserved space. The specific mechanism by which NMR-susceptible nuclei are transported in and out of the reserved space may depend on the specific structure of the MRS, the specific environment in which the MRS is to be used, and the specific use of the MRS.

(4) Colormetric Frequency-Shifting

The MRS may be designed to frequency-shift water protons or other NMR-susceptible nuclei by a wide range of discrete and controllable amounts relative to the background frequency-shift of surrounding NMR-susceptible nuclei. This frequency-shift signal of each MRS design may be used to identify each MRS individually within magnetic resonance imaging data. At least two MRS may be designed to frequency-shift the NMR-susceptible nuclei by discrete and controlled amounts such that the frequency-shift of each MRS is distinguishable from the background frequency-shift as well as the frequency-shift of any of the other MRS. The individual magnitudes of NMR frequency-shifting resulting from individual MRS may be associated with an individual color on a color map of the spectral signatures of the individual voxels within an MR image, greatly enhancing the informational content of MR image data. This effective color signal provides additional information regarding the particular configuration of the MRS in the nuclear resonance image.

As described in detail elsewhere in this application, the frequency-shift induced by a particular MRS may be controllably and consistently specified by a combination of the magnetic material included in the MRS and the shape, dimensions, and separation distances of the magnetic structures included in the MRS. Using a top-down fabrication process, described in detail below, to produce the MRS, magnetic materials having a wide range of magnetic properties may be formed into highly reproducible MRS configurations with precisely defined reserved spaces. As a result, the MRS particles may be designed and produced to reliably frequency-shift NMR-susceptible nuclei by an amount that is up to several orders of magnitude higher than any existing chemical-shift MRI contrast agent.

The MRS may be designed and produced to frequency-shift a NMR-susceptible nucleus by any amount ranging from about −10 Hz up to about −10 MHz. Other designs of the MRS may frequency-shift a NMR-susceptible nucleus by about −10 Hz, about −50 Hz, about −100 Hz, about −150 Hz, about −200 Hz, about −400 Hz, about −600 Hz, about −800 Hz, about −1 kHz, about −10 kHz, about −20 kHz, about −50 kHz, about −100 kHz, about −200 kHz, about −400 kHz, about −600 kHz, about −800 kHz, about −1 MHz, about −2 MHz, about −5 MHz, and about −10 MHz.

Magnetic resonance imaging devices and methods may be used to obtain multispectral colormetric NMR frequency-shift mapping using either direct imaging methods or indirect imaging methods. Using a direct imaging method, a single excitatory electromagnetic pulse at the resonance frequency of each MRS is used to frequency-shift the NMR-susceptible nuclei within the reserved volume, followed by NMR visualization. In this method, diffusion effects do not enhance the strength of the NMR signal contrast because the MRS frequency-shift the NMR susceptible nuclei only during the brief time of the excitatory electromagnetic pulse. Although the spatial resolution obtained using direct imaging is higher due to the concentration of frequency-shifted nuclei to the reserved space, the signal-to-noise ratio is relatively low.

Indirect imaging methods use a series of temporally separated excitatory electromagnetic pulses at the resonance frequency of each MRS followed by NMR visualization of the frequency-shifted nuclei. A significantly larger volume of NMR-susceptible nuclei such as water protons are frequency-shifted using this methods since fluid has sufficient tiem to diffuse in and out of the reserved space between excitatory pulses, effectively replenishing the reserved space with non-frequency shifted nuclei. As a result, the magnitude of the contrast dignal is significantly increased, although the resolution of the signal location is somewhat degraded due to the diffusion of the frequency-shifted nuclei throughout the near-field region of the MRS and beyond during the series of excitatory pulses.

(5) Minimum Detectable Concentration

In order for an MRS to be detected, the contrast signal must exceed the background noise. In the case of $T_2^*$ contrast signaling, the contrast signal may result from interactions of NMR susceptible nuclei with the rapidly decaying magnetic field external to the MRS. In this case, the strength of the contrast signal may be governed by the magnitude of the magnetic moment produced by the MRS within the background magnetic field. In order to be detected using typical researched level high-resolution magnetic resonance visualization methods, the minimum magnetic moment may be about $10^{-15}$ A·m$^2$, $10^{-14}$ A·m$^2$, $10^{-13}$ A·m$^2$, $10^{-12}$ A·m2, $10^{-11}$ A·m$^2$, or $10^{-10}$ A·m$^2$. This exact required minimum will depend on imaging resolution and background noise levels particular to imaging protocols and imaging equipment. For low resolution imaging that may include routine clinical low-resolution imaging the minimum magnetic moment may be higher than all these numbers.

The magnetic moment typically depends on the volume of magnetic material in the MRS as well as the saturated magnetic polarization $J_s$ of the magnetic material, a measure of the magnetic strength of the material. As a result, an MRS constructed from a material with a high $J_s$, such as iron, may produce a detectable magnetic moment using a much smaller volume of magnetic material compared to existing magnetic particle contrast agents, such as MPIOs. For example, if the MRS is a solid disk made of iron ($J_s$=2.2), a single particle having a diameter of about 0.5-μm may produce a suitably high magnetic moment for detection using typical high resolution NMR visualization methods.

For MRS having a reserved space, and being used not in the $T_2^*$ contrast mode, but in their multispectral frequency shifting mode (described above), the contrast signal strength may result from the interactions of NMR-susceptible nuclei such as water protons within the reserved space during the time that the MRS is exposed to an excitatory electromagnetic pulse at the resonance frequency of the MRS. If the MRS is exposed to multiple excitatory pulses, diffusion effects enhance the volume of frequency-shifted nuclei as described above, resulting in a stronger contrast signal compared to a similarly-sized MRS lacking the diffusion effects. Consequently, the strength of the signal, which is proportional to the volume of frequency-shifted nuclei, may be many times greater than the volume of the reserved space, thanks to the contribution of the natural diffusion effects. The contrast signal must exceed the background signal levels in order to be detected.

Because the contrast signal strength of a MRS with a reserved space depends in part on diffusive effects, the overall size of the MRS is a significant factor. Ultimately, the minimum useable size of the MRS may not be limited by fabrication techniques, but by the refresh time ($\tau_d$) for self-diffusion. Ideally, fast diffusion helps increase the volume of water contributing to contrast signal, but the diffusional exchange of fluid in and out of the reserved space of a magnetic resonance structure should not be so fast as to broaden the peak of the NMR signal by more than the shift of the NMR peak relative to the NMR peak shift. Because the MRS is capable of generating sizeable NMR peak frequency shifts, the diffusional broadening of the NMR peak becomes significantly limiting for structures below about 100 nm in size, where the magnetic material concentrations required are in the nanomolar regime. The magnitude of the NMR signal, the shift of the NMR signal peak relative to water protons and other NMR-susceptible nuclei in the far-field region, and the width of the shift NMR signal peak are all dependent on the materials and geometry of the MRS.

If continual longitudinal relaxation is assumed, the magnetic moment saturated out of each magnetic resonance structure pulsed over a time t=2 $T_1$ is $(m_{pulse}/2)*(T_1/\tau_d)*(1-e^{-2})$. Because the signal-to-noise ratio (SNR) varies with the voxel volume of the magnetic resonance imaging device, at least about 1%, 2%, 3%, 4%, 5%, 6%, 7%, 8%, 9%, or 10% fractional saturation of the water protons or other NMR-susceptible nuclei may be needed for reliable detection of an MRS. The minimum detectable concentration of the MRS with a reserved space may be about $10^{-16}$ M, $10^{-15}$ M, $10^{-14}$ M, $10^{-13}$ M, $10^{-12}$ M, or $10^{-11}$ M, depending on the overall size and magnetic material of the NMR, and the resolution and background noise of the NMR imaging device. For example, if the MRS with reserved space is a about 1 micrometer in overall size, the minimum detectable concentration may be about $10^{-14}$ M. In general, smaller sized MRS will have lower detectable concentrations than larger MRS, due to the relatively higher contribution of diffusion effects in the smaller structures. That is, although the required molar concentration (representing a measure of number of individual MRS's) must increase as MRS sizes decrease, the total amount of material required (which is of course less for each smaller MRS) will go down overall, leading to a highly favorable scaling of required material concentrations and MRS size decreases. Thanks to diffusion, the required concentration reduces quadratically with the MRS size.

The minimum detectable concentration of the MRS may be well below that of existing contrast agents such as chemical exchange contrast agents, gadolinium relaxivity-based contrast agents and may be comparable to the minimum detectible concentration of existing SPIO contrast agents. Further, since existing gadolinium and SPIO agents are not spread evenly throughout the body after administration, the minimum detectable concentration of the MRS may be far below that of the actual detected concentrations of other exiting agents including SPIO contrast agents.

The minimum detectible concentration may also be quantified as the minimum number of contrast particles per unit volume that may be detected by typical magnetic resonance visualization devices. For all MRS, including solid particulate MRS and MRS including a reserved space, single particles may be detected using typical existing magnetic resonance visualization devices such as MRI scanners. As a result, the minimum number of particles that may be detected per unit volume may often be as low as one particle per unit volume. The ability to detect single particles depends in part on the overall size of the particle, as discussed above for both the solid particulate MRS and the MRS with a reserved space, in addition to the image resolution of the magnetic resonance visualization device. Further, in order to discriminate between two or more individual particles the particles may need to have a minimum separation distance. For the case of solid MRS, this minimum would be at least one imaging voxel. For the case of cavity/reserve space MRS, this minimum can be far smaller that even a single voxel because the frequency discrimination can be used to separate the two. In order to minimize, however, the signal distortion due to interference of the magnetic field of one MRS with a second MRS, the MRS may be separated by a distance of at least 2-3 times the overall size of the MRS, which will generally still be many times smaller than an individual voxel size.

c. Geometric Arrangements of Magnetic Material for Reserved Space MRS

The magnetic resonance contrast provided by the reserved space MRS is highly sensitive to its size and arrangement of the magnetic materials. The magnetic material may form the reserved space within a continuous structure, or within an arrangement of two or more magnetic portions. The two or more magnetic portions may be separate structures, or different portions of an integral structure. The two or more magnetic portions may be formed in any shape and held in any arrangement such that an essentially uniform magnetic field is formed within the reserved space when the MRS is placed in a magnetizing field. The reserved space MRS may be any variance or defamation in shape or thickness of the MRS. The reserved space MRS may be a dual disk MRS. The reserved space MRS may also have a tubular or hollow shape, such as a hollow cylinder, a spherical shell, a rod, an elliptical shell, a shell with multiple small holes, or any other hollow shell shape. For example, the reserved space MRS may be a slightly curved cylinder or may be a disc that has varying thickness over the contours of the disk.

The magnetic material may form at least one or more openings to allow fluid to freely diffuse and/or flow in and out of the reserved space inside the near-field volume. The total surface area occupied by the one or more openings formed by the magnetic material may range from about 0.1% to about 90% of the total outer surface area of the MRS. The one or more openings may also occupy a total surface area ranging from about 0.1%, 0.2%, 0.3%, 0.4%, 0.5%, 0.6%, 0.7%, 0.8%, 0.9%, 1.0%, 1.5%, 2.0%, 2.5%, 3.0%, 3.5%, 4.0%, 4.5%, 5.0%, 5.5%, 6.0%, 6.5%, 7.0%, 7.5%, 8.0%, 8.5%, 9.0%, 9.5%, 10% to about 20%, from about 15% to about 25%, from about 20% to about 30%, from about 25% to about 35%, from about 30% to about 40%, from about 35% to about 45%, from about 40% to about 50%, from about 45% to about 55%, from about 50% to about 60%, from about 55% to about 65%, from about 60% to about 70%, from about 65% to about 75%, from about 70% to about 80%, from about 75% to about 85%, or from about 80% to about 90% of the total outer surface area of the reserved space MRS. The total outer surface area of the reserved space MRS is dependent on its' overall size and shape.

The MRS may comprise a reserved space enclosed by a semipermeable material to allow fluid to move in and out of the reserved space via diffusion or convection. The semipermeable material may be any biological or synthetic semipermeable material known in the art. The semipermeable material may allow certain molecules or ions to pass through by diffusion or facilitate diffusion. The semipermeable membrane may be a phospholipid bilayer, a nanoporous polymer, a microporous polymer, a cell membrane, a thin film composite membrane, polyimide, cellulose ester membrane, charge mosaic membrane, bipolar membrane, anion exchange membrane, alkali anion exchange membrane, and proton exchange membrane. The MRS may comprise a reserved space that is enclosed by a non-permeable material such as gold or titanium coatings thereby trapping the fluid inside. For example, the MRS may a completely package reserved space for use in microfluidic applications as discussed below.

(1) Dual-Disk Magnetic Resonance Structure

The reserved space MRS may be in the form of a dual-disk magnetic resonance structure (MRS). The dual-disk MRS may include two disk-shaped magnetic portions held apart at a fixed distance by one or more non-magnetic support elements. The open geometry of the dual-disk design may enhance the accessibility of the reserved space to the diffusive and/or convective exchange of fluid. The one or more non-magnetic support elements may be in the form of one or more spacers arranged between the two or more magnetic portions of the MRS, or one or more spacers arranged to be located external to the reserved space between the two or more magnetic portions.

The spacer arranged between two or more magnetic portions may maintain the reserved space such that the reserved space is open to permit a fluid to flow in and out of the reserved space or enclosed area of fluid. The spacer may be arranged to partially or completely fill the reserved space between the magnetic portions to prevent the movement of fluid in or out of the reserved space. The nonmagnetic material of the spacer may have different properties in different environments, including surrounding pH, temperature, and solution salinity. These environmentally-dependent properties of the nonmagnetic spacer material may be utilized to produce a change in the essentially uniform magnetic field or within the reserved space. These changes produce detectable changes in the signals produced by the dual-disk MRS during observation with a magnetic resonance system, or change to block or unblock the reserved space thereby making the reserved space inaccessible or accessible to fluid.

Each spacer may be formed from a non-magnetic material. The non-magnetic material of the spacer may be an internal metal post, a photo-epoxy post, a biocompatible material, hydrogel, or various polymer materials. For example, the nonmagnetic material of the spacers may expand or contract as a function of temperature. As temperature varies, the spacing between the two or more magnetic portions may increase or decrease, thereby changing the magnitude of the essentially uniform magnetic field within the reserved space, resulting in a different spectral shift of water protons and other NMR-susceptible nuclei during magnetic resonance probing. The materials of the spacers may decompose, or disconnect from the magnetic portions, thereby disrupting the arrangement of the magnetic portions and eliminating the internal uniform magnetic field inside the reserved space entirely. The spacing of the disks may be altered in response to various physiological and chemical factors by changing the geometry of the spacer. In addition, the dual-disk MRS may be simply inactivated by disintegration of the spacer element.

The magnetic material of the dual-disk MRS may be iron, nickel, a hybrid material, or mixtures thereof. The magnetic disk may be layered with different magnetizable materials such as iron, nickel, chromium, manganese, cobalt, or any magnetic alloy such as permalloy, neodymium alloy, alnico, bismanol, cunife, fernico, heusler alloy, mkm steel, metglass, samarium-cobalt, sendust, or supermalloy. The magnetic disk may be coated with non-magnetic materials such as gold, titanium, zinc, silver, tin, aluminum, or any other material that does not generate a magnetic field. These non-magnetic materials may also be used to provide a cohesive layer between two other magnetic material layers of the disk. Each of these layers may have a thickness of 1-10 nm, 1-nm, 2-nm, 3-nm, 4-nm, 5-nm, 6-nm, 7-nm, 8-nm, 9-nm, 10-nm, 20-nm, 30-nm, 40-nm, 50-nm, 60-nm, 70-nm, 80-nm, 90-nm, 100-nm, 150-nm, 200-nm, 250-nm, 300-nm, 350-nm, 400-nm, 450-nm, 500-nm, 600-nm, 700-nm, 800-nm, 900-nm, 1000-nm, 1-μm, 2-μm, 3-μm, 4-μm, 5-μm, 6-μm, 7-μm, 8-μm, 9-μm, 10-μm, 20-μm, 30-μm, 40-μm, 50-μm, 60-μm, 70-μm, 80-μm, 90-μm, 100-μm, 150-μm, 200-μm, 250-μm, 300-μm, 350-μm, 400-μm, 450-μm, 500-μm, 550-μm, 600-μm, 650-μm, 700-μm, 750-μm, 800-μm, 850-μm, 900-μm, 950-μm, 1000-μm, 1-mm, 2-mm, 3-mm, 4-mm, 5-mm, 6-mm, 7-mm, 8-mm, 9-mm, 1-cm, 2-cm, 3-cm, 4-cm, 5-cm, 6-cm, 7-cm, 8-cm, 9-cm, or 10-cm.

The magnetic disks may be constructed from materials that are magnetized by a background magnetic resonance field that is much larger in magnitude than the essentially uniform magnetic field generated by the dual-disk MRS. Because of the quadrature vector addition of magnetic fields, only those components of the essentially uniform magnetic field that are parallel or antiparallel to the background magnetic resonance field need be substantially uniform and homogeneous. The dual-disk MRS may also be constructed from a permanent magnetic material and may be used with our without background magnetic field. The entire essentially uniform magnetic field of the reserved space may be substantially uniform and homogeneous.

The disks of the double disk MRS may have a thickness (h) of 1-nm, 2-nm, 3-nm, 4-nm, 5-nm, 6-nm, 7-nm, 8-nm, 9-nm, 10-nm, 20-nm, 30-nm, 40-nm, 50-nm, 60-nm, 70-nm, 80-nm, 90-nm, 100-nm, 150-nm, 200-nm, 250-nm, 300-nm, 350-nm, 400-nm, 450-nm, 500-nm, 550-nm, 600-nm, 650-nm, 700-nm, 750-nm, 800-nm, 850-nm, 900-nm, 950-nm, 1000-nm, 1-μm, 3-μm, 4-μm, 5-μm, 6-μm, 7-μm, 8-μm, 9-μm, 10 μm. The radius (R) of the disc may be 2-nm, 5-nm, 6-nm, 7-nm, 8-nm, 9-nm, 10-nm, 15-nm, 20-nm, 25-nm, 30-nm, 35-nm, 40-nm, 45-nm, 50-nm, 60-nm, 70-nm, 80-nm, 90-nm, 100-nm, 150-nm, 200-nm, 250-nm, 300-nm, 350-nm, 400-nm, 450-nm, 500-nm, 550-nm, 600-nm, 650-nm, 700-nm, 750-nm, 800-nm, 850-nm, 900-nm, 950-nm, 1000-nm, 1-μm, 2-μm, 3-μm, 4-μm, 5-μm, 6-μm, 7-μm, 8-μm, 9-μm, 10-μm, 20-μm, 30-μm, 40-μm, 50-μm, 60-μm, 70-μm, 80-μm, 90-μm, 100-μm, 150-μm, 200-μm, 250-μm, 300-μm, 350-μm, 400-μm, 450-μm, 500-μm, 550-μm, 600-μm, 650-μm, 700-μm, 750-μm, 800-μm, 850-μm, 900-μm, 950-μm, 1000-μm, 1-mm, 2-mm, 3-mm, 4-mm, 5-mm, 6-mm, 7-mm, 8-mm, 9-mm, 7-mm, 8-mm, 9-mm, 1-cm, 2-cm, 3-cm, 4-cm, 5-cm, 6-cm, 7-cm, 8-cm, 9-cm, 10-cm, 20-cm or 30-cm. The center to center separation (2S) between the dual disks may be 50-nm, 60-nm, 70-nm, 80-nm, 90-nm, 100-nm, 150-nm, 200-nm, 250-nm, 300-nm, 350-nm, 400-nm, 450-nm, 500-nm, 550-nm, 600-nm, 650-nm, 700-nm, 750-nm, 800-nm, 850-nm, 900-nm, 950-nm, 1000-nm, 1-μm, 2-μm, 3-μm, 4-μm, 5-μm, 6-μm, 7-μm, 8-μm, 9-μm, 10-μm, 20-μm, 30-μm, 40-μm, 50-μm, 60-μm, 70-μm, 80-μm, 90-μm, 100-μm, 150-μm, 200-μm, 250-μm, 300-μm, 350-μm, 400-μm, 450-μm, 500-μm, 550-μm, 600-μm, 650-μm, 700-μm, 750-μm, 800-μm, 850-μm, 900-μm, 950-μm, 1000-μm, 1-mm, 2-mm, 3-mm, 4-mm, 5-mm, 6-mm, 7-mm, 8-mm, 9-mm, 10-mm, 20-mm, 30-mm, 40-mm, 50-mm, or 100-mm. The saturation magnetic polarization (Js) may be 0, 0.1, 0.2, 0.3 T, 0.4 T. 0.5 T, 0.6 T, 0.7 T, 0.8 T, 0.9 T, 1.0 T, 1.5 T, 2.0 T, or 2.5 T.

The double disk MRS may be as shown in FIG. 1. In this embodiment, the MRS 100 includes two magnetic disks 102 and 104—an upper magnetic portion 102 and a lower magnetic portion 104 that are arranged at a constant distance from each other, forming a reserved space 106 between the magnetic portions. The reserved space 106 may be filled with a non-magnetic material, such as a fluid, which may be water, a paste, a gel or a gas. The non-magnetic material may flow and/or diffuse through at least a portion of the reserved space 106. When the magnetic portions 102 and 104 are placed within a magnetizing field 108, magnetic moments 114 and 116 and associated magnetic fields 110 and 112 are induced. In the reserved space 106, the induced magnetic fields 110 and 112 interact to form an essentially uniform magnetic field. This essentially uniform magnetic field induces the nuclear magnetic moments of any material passing through the reserved space 106, such as water molecules or other NMR-susceptible nuclei, to precess at a characteristic Larmor frequency if the NMR is exposed to a resonant electromagnetic pulse and if the combined magnetic field is uniform (background+reserved space). The magnitude of the essentially uniform field in the reserved space is sufficiently different from all surrounding fields such that the characteristic Larmor frequency of the NMR-susceptible material passing through the reserved space 106 during exposure of the MRS to a resonant electromagnetic pulse and is detectably different from the Larmor frequency induced by the background field 108 in the absence of the MRS 100. The characteristic Larmor frequency is identifiable with the particular arrangement and choice of materials making up the MRS 100.

The total magnetic field in the reserved space may be equal to the local magnetic field (reserved field space and background field) created by the MRS. The total magnetic field in the reserved space 106 may be equal to the combined local magnetic fields 110 and 112 created by the MRS 100, in a case in which the MRS 100 is not embedded in a magnetizing field 108 while in use. A local region of interest may include the central portion of the region between the two spaced magnetic disks, such as the disks shown in FIG. 1. The total magnetic field in the reserved space 106 may be a combination of the local magnetic field created by the MRS 100 and a portion of a background magnetic field when the magnetic resonance structure 100 is embedded in the background field during use. Alternatively, the local region of interest may include the control portion of the region between the two spaced magnetic disks such as the disks shown in FIG. 1.

Figure 2:
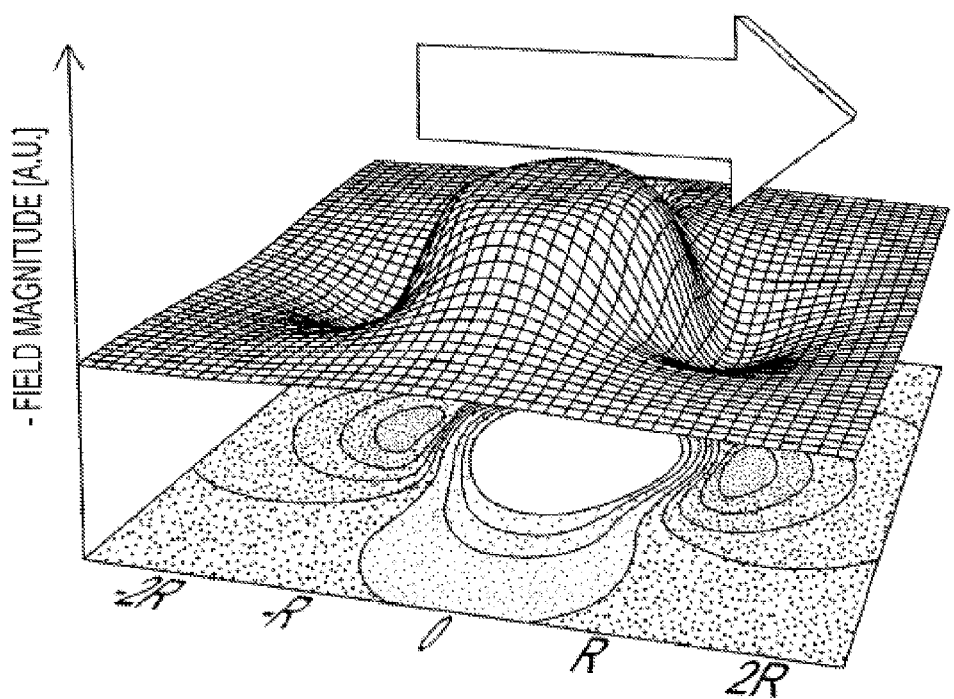
FIG. 2 is a contour graph showing the calculated magnitude of a magnetic field throughout a plane oriented between the disks of an embodiment of a dual-disk magnetic resonance structure.
Figure 8:
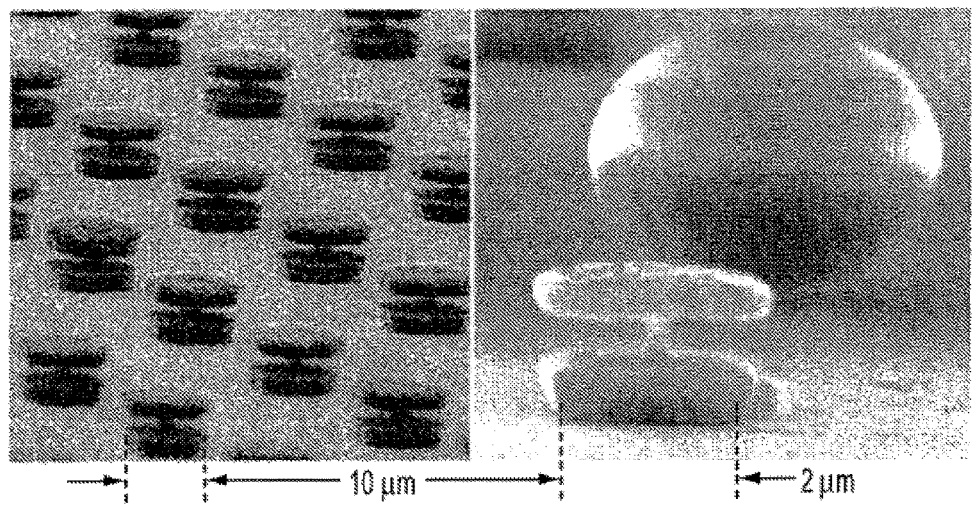
FIG. 8 is a scanning electron micrographs (SEM) image of an embodiment of a dual-disk magnetic resonance structure.
Figure 9:
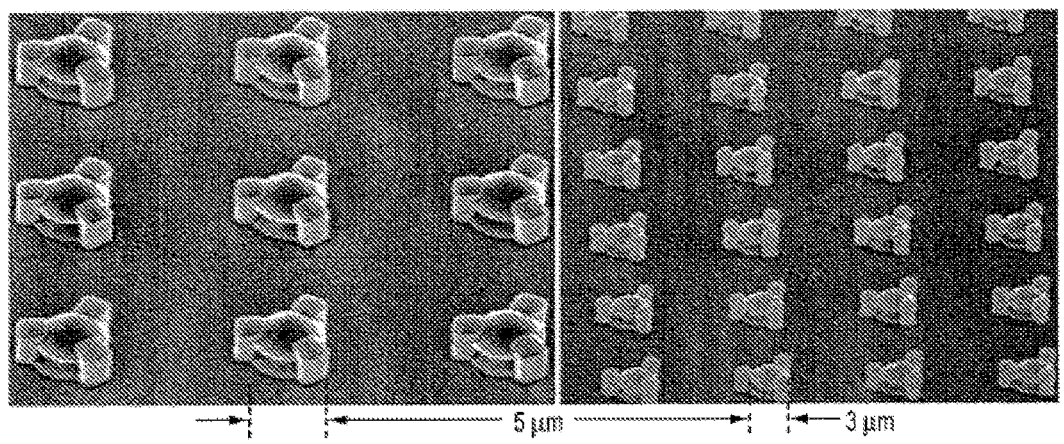
FIG. 9 is a SEM image of another embodiment of a dual-disk magnetic resonance structure.

FIG. 2 shows the calculated distribution of the magnitude of the magnetic field corresponding to the MRS of FIG. 1. The dual-disk MRS generates a highly homogeneous magnetic field over a large volume fraction, as shown in FIG. 2, and the open design helps maximize fluid self-diffusion and/or convection that dramatically increases its signal-to-noise ratio (SNR) over that of existing closed structure MRI contrast agents, as discussed above. In addition, the dual-disk MRS is inherently scalable and well-suited to massively parallel wafer-level microfabrication techniques explained in detail below. The discs 102 and 104 may be held in position by non-magnetic spacers that may include an internal metal post (see FIG. 8) or one or more external biocompatible photo-epoxy posts (see FIG. 9).

The Larmor frequency shift $\Delta\omega$ relative to the Larmor frequency of the water protons and other NMR-susceptible nuclei located in the far-field region of the MRS may be approximated analytically using the estimated magnetic field strength at the center of the dual-disk MRS. Using elementary magnetostatics analysis, the Larmor frequency shift $\Delta\omega$ near the center of the reserved area for the MRS including a pair of magnetically saturated disks may be determined using the relationship given in Eqn. (2):

$$\Delta\omega = (\gamma J_s/2) \cdot [(S-h/2)((S-h/2)^2+R^2)^{1/2} - (S+h/2)((S+h/2)^2+R^2)^{1/2}] \quad (2)$$

where $\gamma$ is the gyromagnetic ratio, h is the disk thickness, R is the disk radius, 2S is the center-to-center disk separation, and $J_s$ is the saturation magnetic polarization. For thin discs with $h \ll 2S \approx R$, this reduces to Eqn. (3):

$$\Delta\omega \approx -\gamma J_s \frac{hR^2}{2(R^2+S^2)^{3/2}} \quad (3)$$

The Larmor frequency shift may be specified by modifying any of the quantities specified in Eqn. (3), including $J_s$, h, R, S and combinations thereof. For example, if the disks are constructed of soft iron, which has a $J_s$ of about 2.2 Tesla, a Larmor frequency shift of about −10 MHz may be achieved.

Figure 10:
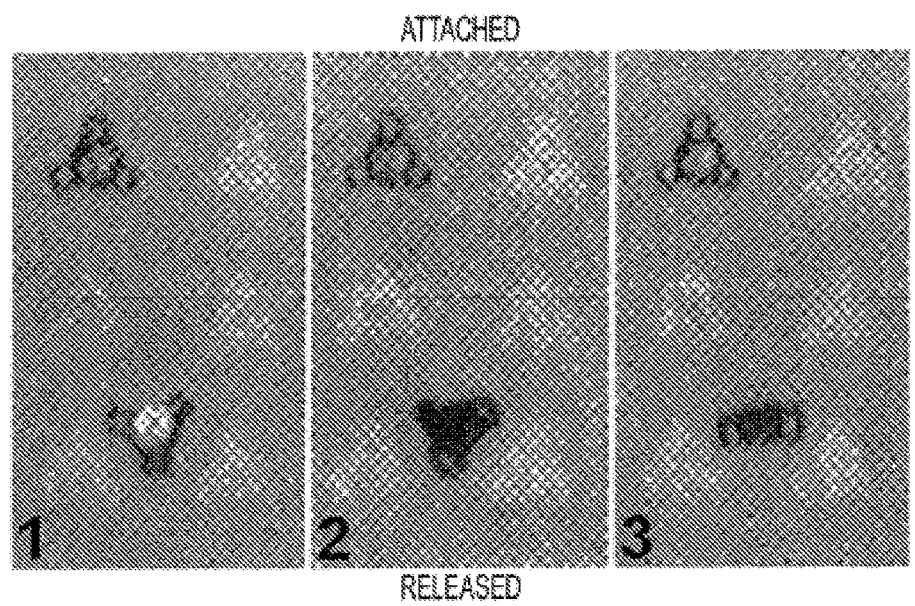
FIG. 10 is another SEM image of yet another embodiment of a dual-disk magnetic resonance structure.
Figure 11:
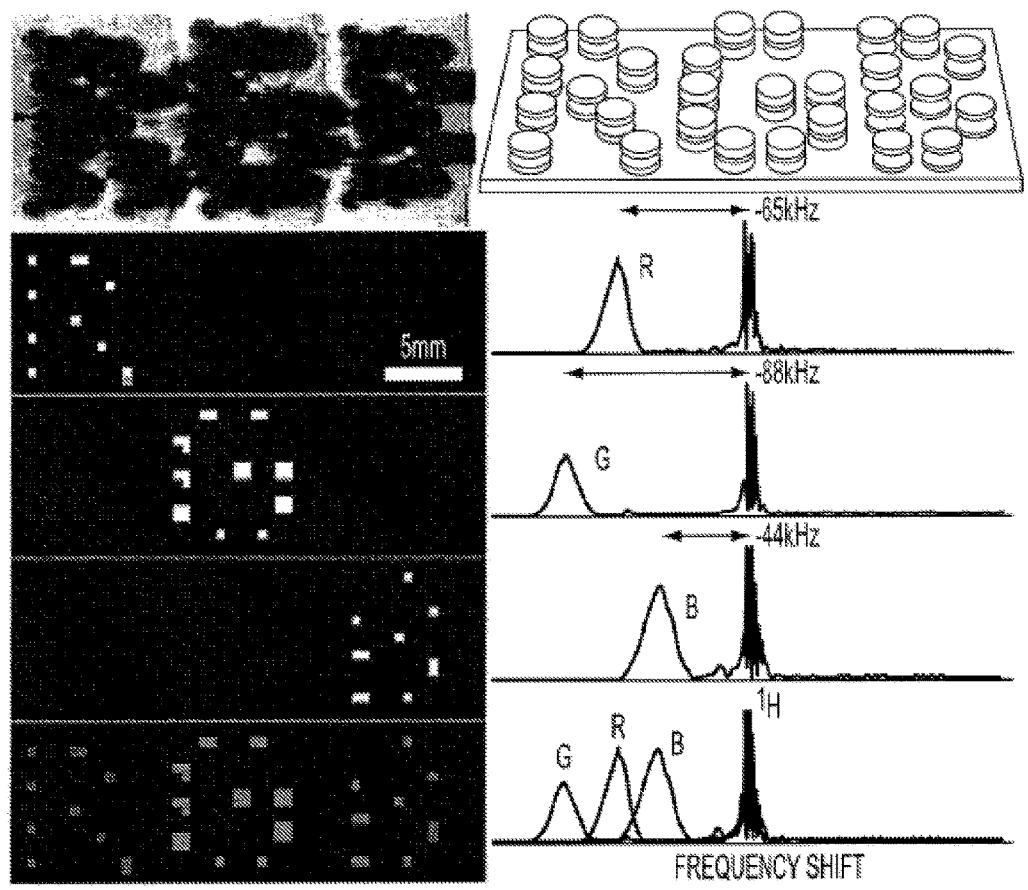
FIG. 11 is a graph of the z-spectra produced using three embodiments of the dual-disk magnetic microstructures.
Figure 12:
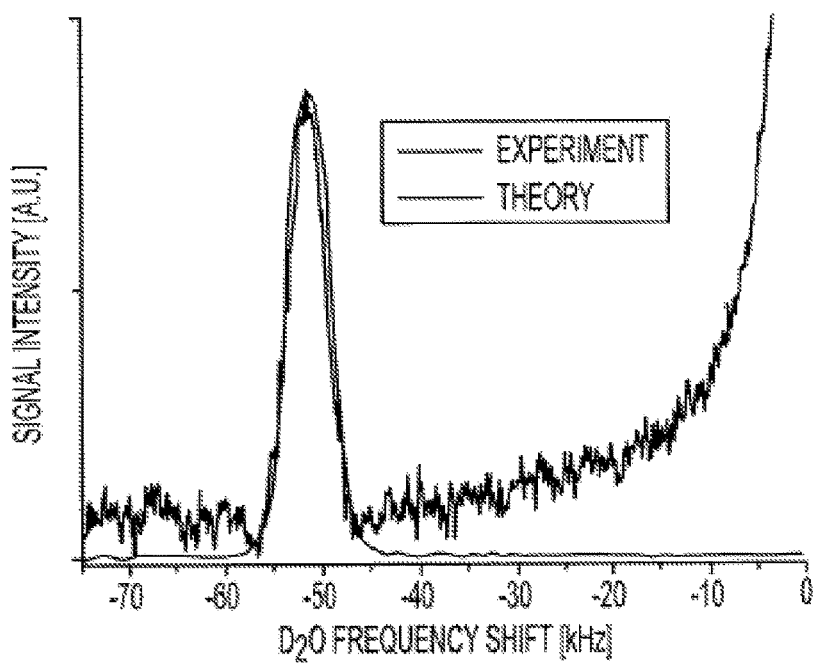
FIG. 12 is a graph of the Fourier transformed spin-echo signal generated from direct MRI imaging from an embodiment of the dual-disk magnetic resonance structures.

The estimates of Larmor frequency shifting described above implicitly assume alignment between the disc planes and the applied magnetizing magnetic resonance field, $B_0$. Such alignment may be passively maintained by the inherent magnetic shape anisotropy of the MRS, as shown in FIG. 10. For any misalignment angle ($\theta$) between $B_0$ and the disk planes, the resulting magnetic torques on the discs produce an automatic self-aligning pressure of approximately (h/$(R^2+S^2)^{1/2})(J_s^2/\mu_0) \cdot \sin(2\theta)$, equating to a pressure of about $10^{-8}$ to about $10^{-6}$ N/μm². By comparison, within cellular cytoplasm, the yield stresses range from about $10^{-13}$ to about $10^{-9}$ N/μm².

Figure 6:
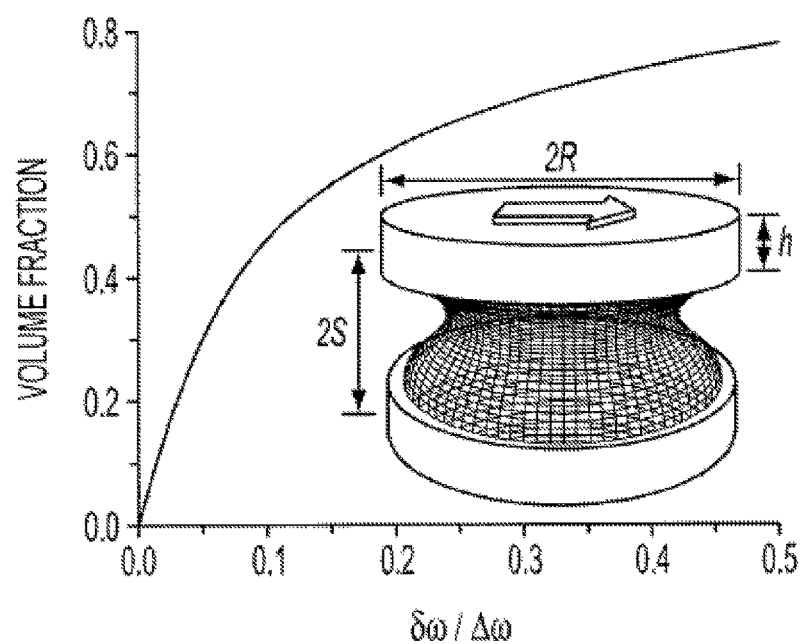
FIG. 6 is a graph of the calculated particle volume fraction that falls within a bandwidth, $\delta\omega$, about the particle's frequency shift, $\Delta\omega$ for an embodiment of a magnetic resonance microstructure.

The relatively high homogeneity of the essentially uniform magnetic field (MRS field+background field) within the reserved space of the dual-disk MRS may suppress the background magnetic resonance signal while still saturating out about ⅓ of the volume between the discs via off-resonant magnetic resonance excitation pulses with bandwidths of just a few percent of the shift of the MRS, as shown in FIG. 6. For an equilibrium $B_0$-aligned magnetization, $M_0$, and $h \ll 2S \approx R$, the magnetic moment of the NMR-susceptible nuclei saturated in a single excitation pulse is $m_{pulse} \approx M_0 \pi R^3/3$. Since not all of the fluid within the near-field region exchanges between consecutive excitation pulses, however, this pre-pulse magnetic saturation volume falls with subsequent pulses. For an inter-pulse delay ($\tau_d$) of $R^2/6D$, simulations indicate that a resulting per-pulse average saturation may be about $m_{pulse}/2$. The spatial distribution of any single excitatory pulse of saturated magnetization at some later time, $t \gg \tau_d$, may be approximated by analogy to an instantaneous point-source diffusion problem, giving Eqn. (4):

$$M_s(r,t) \approx (m_{pulse}/2)(4\pi Dt)^{-3/2} \exp(-r^2/4Dt)\exp(-t/T_1) \quad (4)$$

where the final factor accounts for relaxation back into alignment with $B_0$, and r measures the distance from the MRS. Within a characteristic diffusion distance, $d \equiv (D \cdot T_1)^{1/2}$, a $\tau_d$-spaced train of such excitatory pulses rapidly (over a time of approximately $T_1$) asymptotes to a steady-state distribution given by Eqn. (5):

$$M_s(r) \approx (M_0/4)(R/r) \cdot e^{-r/d} \quad (5)$$

By integrating Eqn. (5) over a spherical voxel of radius $R_v \gg R$ with $R_v \ll d$, the approximate reduction in magnetization surrounding the particle may be given by Eqn. (6):

$$M_s/M_0 \approx 0.3 R/R_v \quad (6)$$

Eqn. (6) highlights the diffusion-enabled linear scaling that boosts SNR relative to the cubic scaling that would result if there was no diffusion.

For example, although the reserved space of a dual-disk MRS having a dimension R=2.5 μm (see FIG. 9) constitutes just 0.003% of the volume of a 50 μm radius voxel, the structure may actually saturate the Larmor frequency of the water protons or other NMR-susceptible nuclei of a volume of that is about 2% of the voxel. This thousand-fold larger volume of saturated water protons or other NMR-susceptible nuclei surrounding the dual-disk MRS potentially enables the simultaneous single particle imaging and spectral identification (see FIG. 17) without need for specialized sensitive micro-coils. For example, the MRI images shown in FIG. 17 were obtained using a magnetic resonance scanner with macroscopic surface and solenoidal RF coils up to several centimeters in diameter.

(2) Hollow Cylinder MRS

The MRS may also be in the form of a hollow cylinder MRS. Although the hollow cylinder MRS differs from the dual-disk MRS, the physical basis behind the NMR spectral shifting properties of the hollow cylinder MRS may be conceptualized in a similar manner to the dual-disk MRS. The essentially uniform magnetic field in the reserved space between the two suitably spaced magnetized disks possesses the necessary homogeneity to induce such shifted NMR peaks when exposed to a resonant electromagnetic pulse. In such a double-disk structure, the disks are assumed aligned such that the $B_0$ magnetic field vector is parallel to the plane of the disks. However, this alignment requirement restricts orientation only about a single axis; the dual-disk structure is free to rotate about a central axis parallel to $B_0$. Because the resulting NMR color frequency shifts are invariant with respect to this rotation, a variety of alternative structures, each composed of what may be regarded as superpositions of rotated dual-disk structures, may also possess the appropriate homogeneous field profiles. Although a hollow cylinder represents a surface of revolution of a radially-offset thin rectangle, rather than a disk shape, the similarity of the hollow cylinder structure MRS to a rotated dual-disk MRS means that the magnetic fields in the reserved space may likewise generate distinct spectrally shifted color NMR peaks.

The hollow cylinder MRS may be scalable down to the nano-regime with an optimal length-to-diameter ratio just above unity. The hollow cylinder MRS is defined by the overall saturation magnetic polarization (Js), wall thickness (t), diameter ($2\rho$), and length (L). The wall thickness (t) of the hollow cylinder MRS may be 1-nm, 2-nm, 3-nm, 4-nm, 5-nm, 6-nm, 7-nm, 8-nm, 9-nm, 10-nm, 15-nm, 20-nm, 25-nm, 30-nm, 35-nm, 40-nm, 45-nm, 50-nm, 55-nm, 60-nm, 65-nm, 70-nm, 75-nm, 80-nm, 85-nm, 90-nm, 95-nm, 100-nm, 110-nm, 120-nm, 130-nm, 140-nm, 150-nm, 160-nm, 170-nm, 180-nm, 190-nm, 200-nm, 250-nm, 300-nm, 350-nm, 400-nm, 450 nm, and 500-nm, 550-nm, 600-nm, 650-nm, 700-nm, 750-nm, 800-nm, 850-nm, 900-nm, 950-nm, 1000-nn, 2-µm, 3-µm, 4-µm, 5-µm, 10-µm, 100-µm, 200-µm, 300-µm, 400-µm, 500-µm, 600-µm, 700-µm, 800-µm, 900-µm, or 1 mm. The diameter ($2\rho$) may be 50-nm, 100-nm, 150-nm, 200-nm, 250-nm, 300-nm, 350-nm, 400-nm, 450-nm, 500-nm, 550-nm, 600-nm, 650-nm, 700-nm, 750-nm, 800-nm, 850-nm, 900-nm, 950-nm, 1000-nn, and 5-µm, 10-µm, 100-µm, 200-µm, 300-µm, 400-µm, 500-µm, 600-µm, 700-µm, 800-µm, 900-µm, 1 mm, 2 mm, 3 mm, 4 mm, 5 mm, 10 mm, 20 mm, 30 mm, 40 mm, 50 mm, 60 mm, 70 mm, 80 mm, 90 mm, 1 cm, 2 cm, 3 cm, 4 cm, 5 cm, and 10 cm. The length of the hollow cylinder MRS may be 50-nm, 100-nm, 150-nm, 200-nm, 250-nm, 300-nm, 350-nm, 400-nm, 450-nm, 500-nm, 550-nm, 600-nm, 650-nm, 700-nm, 750-nm, 800-nm, 850-nm, 900-nm, 950-nm, 1000-nn, 4-µm, 5-µm, 10-µm, 100-µm, 200-µm, 300-µm, 400-µm, 500-µm, 600-µm, 700-µm, 800-µm, 900-µm, 1 mm, 2 mm, 3 mm, 4 mm, 5 mm, 10 mm, 20 mm, 30 mm, 40 mm, 50 mm, 60 mm, 70 mm, 80 mm, 90 mm, 1 cm, 2 cm, 3 cm, 4 cm, 5 cm, and 10 cm. The overall magnetic polarization (Js) may be 0, 0.1, 0.2, 0.3 T, 0.4 T. 0.5 T, 0.6 T, 0.7 T, 0.8 T, 0.9 T, 1.0 T, 1.5 T, 2.0 T, or 2.5 T.

Apart from the smaller nanostructures affording increased biological compatibility, relative to their size, smaller shells may amplify signals to a larger degree than can larger shells. This signal gain with structure miniaturization is due to fluid self-diffusion and/or convection. The effect of diffusion, over typical proton relaxation periods, becomes appreciable on the micro- and nano-scales. The signal amplification of the hollow cylinder structures are enabled through magnetization transfer techniques that exploit the continual exchange of fluid between inside and outside the cylindrical shells. The smaller the cylinder structure, the more rapid the fluid exchange. As such, for comparable total quantities of magnetic material used to construct an ensemble of cylindrical shells, an ensemble containing a greater number of smaller shells can interact with a larger volume of fluid than can an ensemble comprising a smaller number of larger shells. Provided the diffusional exchange is not so fast as to frequency-broaden the spectral peak by more than its shift, the frequency-shifting signals may increase quadratically as the size of the cylindrical structures shrink.

The hollow cylinder MRS shares many of the advantages of the dual-disk MRS, including large, continuously tunable spectral ranges that do not depend on $B_0$ for typical magnetic resonance scanners, as well as relatively low concentration requirements. Additionally, like the double-disk MRS, the hollow cylinder may function as a local physiological probe. For example, if the hollow cylinder MRS was blocked by some substance designed to break down under certain physiological conditions, then the hollow cylinder could act as a sensor, with the spectral signal of the MRS turned on or off depending on whether internal regions of the MRS were opened or closed to the surrounding fluid as suggested in FIG. 23E. While the hollow cylinder MRS may not be potentially dynamically adjustable like the double-disk MRS, since the double-disk MRS has disk spacing that is determined by separate posts, the single-element construction of the hollow cylinder MRS is simpler, and fabricating the hollow cylinder MRS is more scalable to the nano-regime.

Figure 18A:
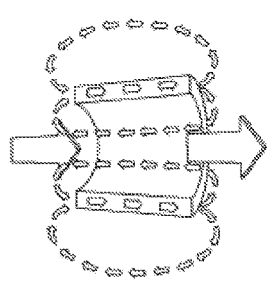
FIG. 18A is an illustration of an embodiment of a hollow cylinder structure.

The MRS may be a hollow cylinder MRS 1800, shown in FIG. 18A. The hollow cylinder MRS may function as both a conventional $T_2^*$ contrast agent and as a Larmor frequency-shifting contrast agent. The hollow cylinder MRS 1800 in this embodiment are formed from shells 1802 of magnetizable material of as little as a few nanometers in thickness. In addition to modulating local magnetic resonance relaxivities like any other magnetic particle, the hollow cylinder MRS 1800 may also induce controlled, tunable nuclear magnetic resonance (NMR) shifts in the surrounding water protons and other NMR-susceptible nuclei when the MRS is exposed to a resonant resonant electromagnetic pulse through precise control of the shell heights, radii and wall thicknesses.

Figure 18B:
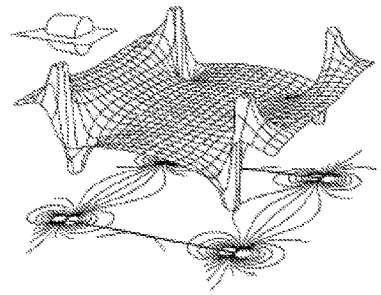
FIG. 18B is a graph showing the calculate magnetic field magnitude profile in a mid-plane through an embodiment of a hollow cylinder magnetic resonance structure.
Figure 18C:
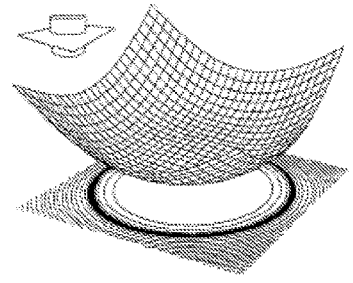
FIG. 18C is a graph showing the calculated magnetic field profile in a perpendicularly oriented mid-plane through an embodiment of a hollow cylinder magnetic resonance structure.
Figure 18D:
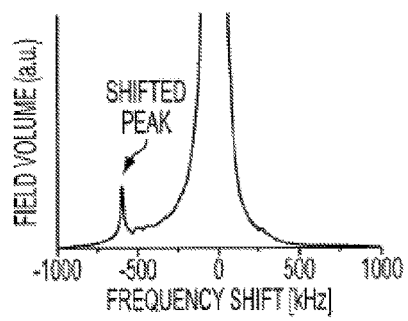
FIG. 18D is a graph showing a histogram recording of the estimated frequency shifts in the volume surrounding an embodiment of a hollow cylinder magnetic resonance structure.
Figure 18E:
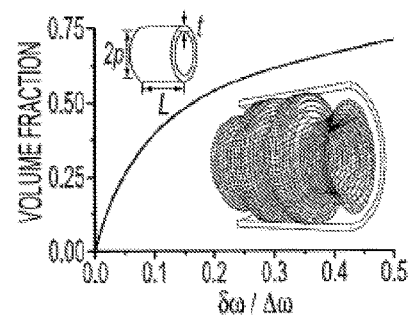
FIG. 18E is a graph showing the calculated internal volume fraction of an embodiment of a hollow cylinder magnetic resonance structure falling within a bandwidth $\delta\omega$ of a central frequency shift $\Delta\omega$.

FIGS. 18B and 18C illustrate the a schematic illustration of the numerically calculated magnetic field magnitude profiles of a cylindrical shell magnetized to saturation by an applied magnetization field $B_0$ in a longitudinal and cross-sectional plane respectively, demonstrating the hollow cylinder's homogeneous internal magnetic field. FIG. 18E illustrates the distinct, detectable, and controllable frequency shift of water protons and other NMR-susceptible nuclei induced by the essentially uniform magnetic field in the reserved space of the hollow cylinder structures when the MRS is exposed to a resonant electromagnetic pulse. The histogram shown in FIG. 18E summarizes the calculated magnetic field magnitudes (or equivalently, Larmor precession frequencies) throughout the space around the hollow cylindrical MRS. By showing the relative volumes of space corresponding to each precession frequency, or field magnitude, the histogram approximates the resulting NMR spectrum from NMR-susceptible nuclei in the shell's vicinity. The shifted spectral peak evident in the histogram is due to the shell's internal homogeneous field region whose spatial extent is delineated by the surface contour plot of FIG. 18E.

Figure 19A:
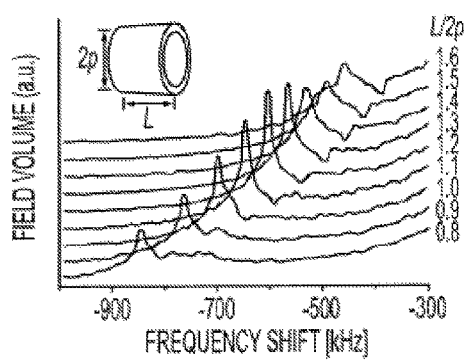
FIG. 19A is a graph showing the spectron of numerous embodiments of hollow cylinder magnetic resonance structures having different length to diameter rating (L/2$\rho$).
Figure 19B:
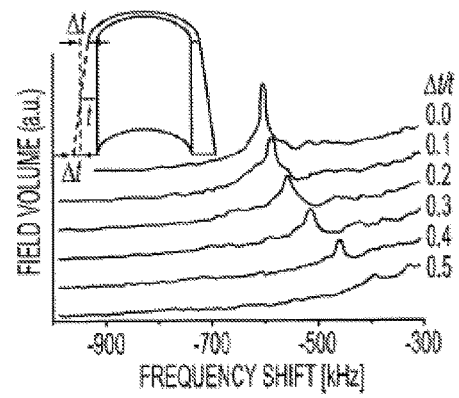
FIG. 19B is a graph showing the spectra of numerous embodiments of hollow cylinder magnetic resonance structures having different degrees of wall thickness variation ($\Delta t/t$).

The shifted resonance line width is influenced largely by the essentially uniform magnetic field homogeneity, which depends on the cylindrical shell geometry as shown in FIGS. 19A and 19B. Although the cylindrical shell walls may have high aspect ratios, the overall cylindrical shell is fairly short, with an optimal length-to-diameter ratio just above unity, as shown in FIG. 19B.

For such a hollow cylindrical structure, the NMR frequency shift ($\Delta\omega$) of the water protons and other NMR-susceptible nuclei within the reserved space may be analytically approximated from the magnetic field at the cylinder's center. Assuming a magnetically saturated cylindrical shell of material, the NMR frequency shift near the center of the reserved space may be expressed as:

$$\Delta\omega = \gamma J_s L [(L^2+(2\rho+t)^2)^{-1/2} - (L^2+(2\rho-t)^2)^{-1/2}] \quad (7)$$

where $J_s$ is the saturation magnetic polarization, t is the cylinder wall thickness, $2\rho$ is the cylinder diameter, L is the length of the cylinder. Simplifying Eqn. (7) to a thin-walled structure in which $t \ll L \approx 2\rho$ results in Eqn. (8):

$$\Delta\omega \approx -4\gamma J_s \frac{L\rho t}{(L^2+4\rho^2)^{3/2}} \quad (8)$$

The relationship specified by Eqn. (8) indicates that the frequency shifts of the hollow cylinder MRS may be engineered by varying the cylindrical shell lengths, radii, wall thicknesses, and material compositions. In this way, the different spectral signatures of different cylindrical shells may be regarded as magnetic resonance frequency analogs to the different optical colors of different quantum dots. However, the geometry of the cylindrical structure, rather than dot size, determines the spectral response of the cylindrical shell. Because the geometrical parameters of the cylindrical structure are combined into a dimensionless ratio in Eqn. (8), the color magnetic resonance frequency shifts are controlled specifically by structure geometry, but are independent of the overall size of the cylindrical structure. Provided that all dimensions of the cylindrical structures are scaled proportionally, nanoscale shells are capable of shifting the color NMR frequencies of the surrounding water protons and other NMR-susceptible nuclei by a similar amount to comparably-proportioned, but far larger cylindrical structures. Because the amount of frequency-shifting $\Delta\omega$ is proportional to a dimensionless ratio of lengths used to specify the MRS geometry, the magnitude of $\Delta\omega$ is independent of the overall size of the MRS. For example, a larger MRS may have a lower $\Delta\omega$ than a smaller MRS having a different dimensionless ratio of lengths used to specify the MRS geometry.

d. Permanent Magnetic Materials/Magnetizable Materials

The magnetic material used to construct the MRS may be any magnetic or magnetizable material known in the art. The magnetic material may be a permanent magnetic material or magnetizable material.

The magnetizable material may be a ferromagnetic, paramagnetic or superparamagnetic material, an alloy or compound, or a combination thereof, optionally in combination with a nonmagnetic or weakly magnetic filler material. The magnetic material may be nickel, iron, chromium, cobalt, manganese, various forms of iron oxide, iron nitride various forms of permalloy, various forms of mu-metal, magnetic alloy such as permalloy, neodymium alloy, alnico, bismanol, cunife, fernico, heusler alloy, mkm steel, metglas, samarium-cobalt, sendust, or supermalloy or a combination thereof. The magnetic material may be of essentially 100% purity, or may be combined with another material to form a hybrid element. For example, the MRS may be constructed from 100% nickel.

The magnetic material may be selected to produce a substantial magnetic moment either intrinsically or when placed into a magnetizing field. The magnetic material may have a saturated magnetic polarization ($J_{ss}$) ranging from 0 T to about 2 T, and may have a $J_s$ of 0, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0 T, 2.1 T, 2.2 T, 2.3 T, 2.4 T, or 2.5 T. For example, the magnetic material included in the MRS may be soft iron with a $J_s$=2.2 T The magnetic material may also be nickel with a $J_s$ ranging from about 0.5 T to about 0.6 T. The magnetic material may be iron oxide with a $J_s$=0.5 T. The magnetic material may also have a magnetic moment that is saturated when the magnetic material is placed in magnetizing fields having strength within the operating capacity of a magnetic resonance visualization system.

The magnetic material may be a single magnetic material, or a combination of two or more magnetic materials. The combination of two or more magnetic materials may be in the form of an alloy in which the magnetic materials are combined in a homogenous mixture, or in the form of a layered magnetic structure in which two or more magnetic materials are formed into two or more discrete layers. Each layer may be made up of a different magnetic material than an adjoining layer.

e. Hybrid Materials and Nonmagnetic Materials

The non-magnetic materials, or hybrid materials containing a mixture of one or more magnetic and non-magnetic materials may be used to construct the MRS in addition to the magnetic materials. These non-magnetic or hybrid materials may be used to position the magnetic materials in a spatial arrangement suitable for forming a reserved space, to modify the diffusion and or flow of fluids in and out of the reserved space, to reinforce the strength of the magnetic materials, and to impart desirable surface properties to the MRS such as biocompatibility, cell-specific affinity, or hydrophobicity. Further, magnetic materials may be deliberately mixed with non-magnetic materials in order to modify the magnetic properties of the resulting mixture. The non-magnetic materials may include non-magnetic metals such as copper, titanium, and gold. In addition, the non-magnetic materials may include non-metals such as a ceramic, a plastic, or a photoresist material. The non-magnetic materials may be physically separate from the magnetic materials, or the non-magnetic materials may be mixed or interspersed among the magnetic materials in the form of particles or layers to form the hybrid material.

The hybrid material may include two or more alternating magnetic and non-magnetic layers, and/or a conglomeration containing smaller particles of magnetic material embedded within a host non-magnetic material. The hybrid element may be a magnetic material and/or layered magnetic structure with an outer coating made of a non-magnetic material. The non-magnetic coating may be an oxidation or corrosion barrier, a mechanical strengthening layer, a non-toxic coating, a biologically inert coating such as titanium, or a coating to facilitate common bioconjugation protocols such as gold. The gold coating may be further functionalized using a technique such as thiol-based chemistry. In addition, the non-magnetic coating may include a coating applied to act as a non-magnetic buffer zone to inhibit magnetic clumping of multiple MRS particles, to improve field uniformity by physically excluding access to select surrounding spatial volumes over which fields might be less uniform than desired, to vary the hydrophobicity of the MRS to enhance or diminish fluid flow through the MRS, or to target the MRS to a specific site or cell by coating the MRS with a particular antibody or other ligand.

f. Overall Size of MRS

The size of the MRS may depend on the intended use of the MRS. The overall size of the magnetic resonance structure (MRS) may range from about 10 nm to about 5 cm, and may be 1, 2, 3, 4, 5, 6, 7, 8, 9, 10, 20, 30, 40, 50, 60, 70, 80, 90, 100, 100, 200, 300, 400, 500, 600, 700, 800, 900 or 1000 nm, or 2, 3, 4, 5, 6, 7, 8, 9, 10, 20, 30, 40, 50, 60, 70, 80, 90, 100, 200, 300, 400, 500, 600, 700, 800, 900, or 1000 µm, or 2, 3, 4, 5, 6, 7, 8, 9, or 10 mm, or 2, 3, 4, or 5 cm. The size of the MRS may be selected according to its particular application or use. In applications such as blood flow visualization or perfusion imaging, the MRS may range in size from about 1 mm to about 5 cm. The size of the MRS may be matched with the size scale of a particular blood vessel. For example, the upper size limit of the MRS may match the size of a human aorta. The MRS may also be larger for use in applications such as industrial flow visualization.

The MRS may also have a maximum dimension between about 10 nm and about 100 µm. The MRS may be smaller than about 10 nm to approach molecular size, and may be particularly useful in micro-tagging applications. The MRS may also have a maximum dimension ranging from about 50 nm to about 10 µm, which may facilitate cellular uptake in a biological, diagnostic and/or medical application.

g. Activatable MRS

The MRS may be used as a "smart" indicator by disrupting the diffusion or flow of fluid into and out of the reserved space using an additional external coating or by filling in the reserved space with a material. By preventing the access of fluid into the reserved space, the frequency-shifting function of the MRS is effectively inactivated. The external coatings or filler materials may be selected to disintegrate under selected conditions in order to activate the frequency-shifting function of the MRS. Once the external coatings or filler have disintegrated, the frequency-shifting function of the MRS is irreversibly activated.

The specific structure of the dual-disk MRS may be used as a "smart" indicator by selecting a material for the spacer between the disks that either disintegrates, swells, and/or shrinks in response to changes in environmental factors such as temperature, pressure, pH, salinity, presence of an enzyme, and others. If the spacer material disintegrates, the dual disks are separated and the frequency-shifting function is irreversibly disabled. If the spacer material, which may be a hydrogel, swells or shrinks in response to an environmental factor, the spacing between the disks is altered, resulting in an altered magnitude of frequency shift, due to the dependence of the magnitude of the frequency shift on the relative positioning and dimensions of the magnetic elements of the dual-disk MRS, including the disk spacing. Thus, a dual-disk MRS having a swellable spacer material produces a frequency shift that reversibly changes to reflect changes in an environmental factor.

Figures 17A, 17B, 17C:
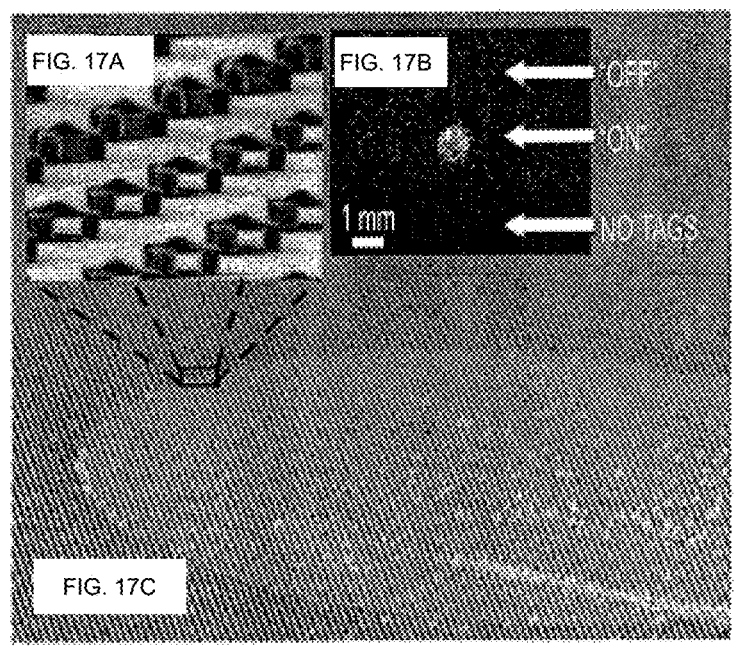
FIG. 17A is an image of a high tilt angle SEM showing a square array of an embodiment of the dual-disk magnetic resonance particle; in which part of the particles have filled interior regions.
FIG. 17B is an MRI image of the dual-disk magnetic resonance particles shown in FIG. 17A.
Figure 23A:
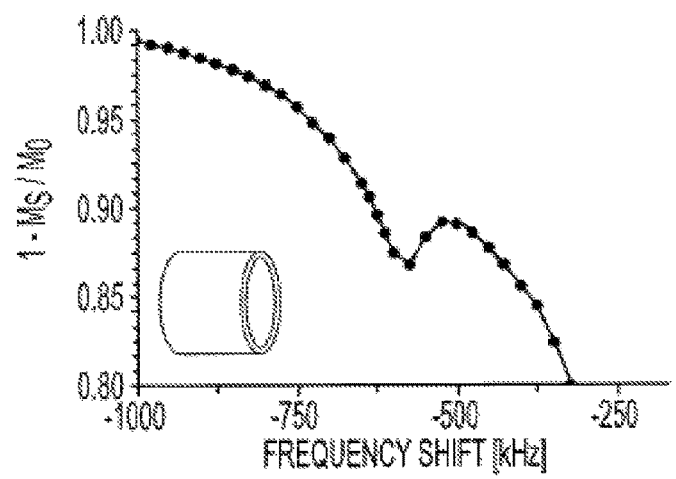
FIG. 23A is a graph showing the z-spectra of an embodiment of a hollow cylinder magnetic resonance structure having a radius of 1 μm, a wall thickness of 75 nm.
Figure 23B:
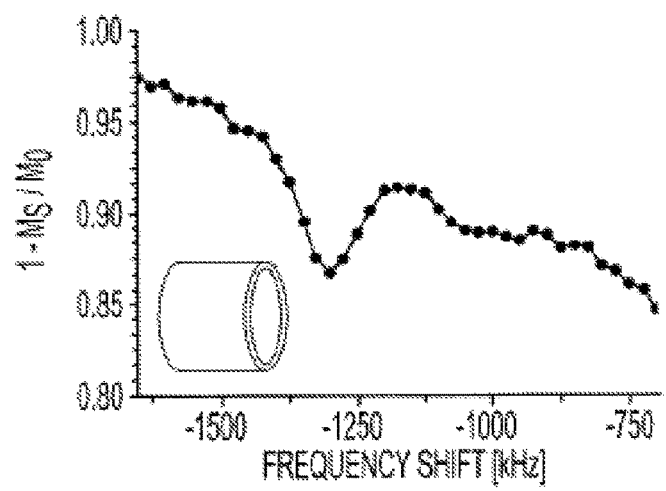
FIG. 23B is a graph showing the z-spectra of an embodiment of a hollow cylinder magnetic resonance structure having a radius of 1 μm, a wall thickness of 150 nm.
Figure 23C:
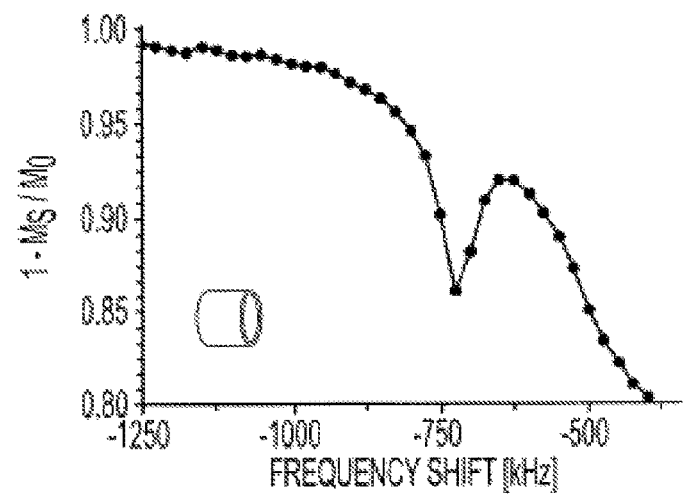
FIG. 23C is a graph showing the z-spectra of an embodiment of a hollow cylinder magnetic resonance structure having a radius of 425 nm, a wall thickness of 40 nm.
Figure 23D:
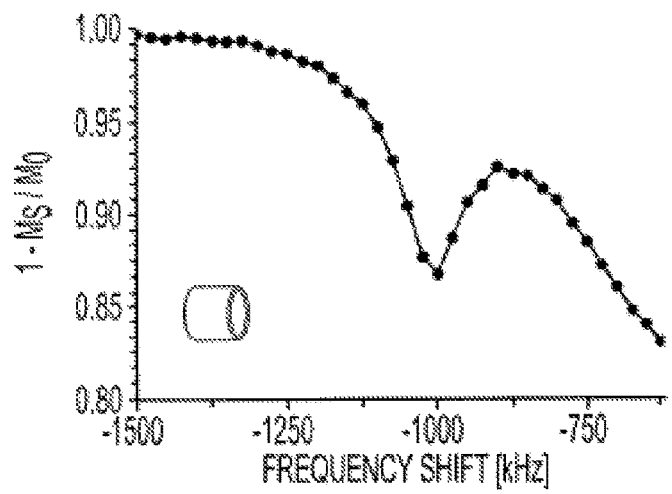
FIG. 23D is a graph showing the z-spectra of an embodiment of a hollow cylinder magnetic resonance structure having a radius of 450 nm, a wall thickness of 50 nm.
Figure 23E:
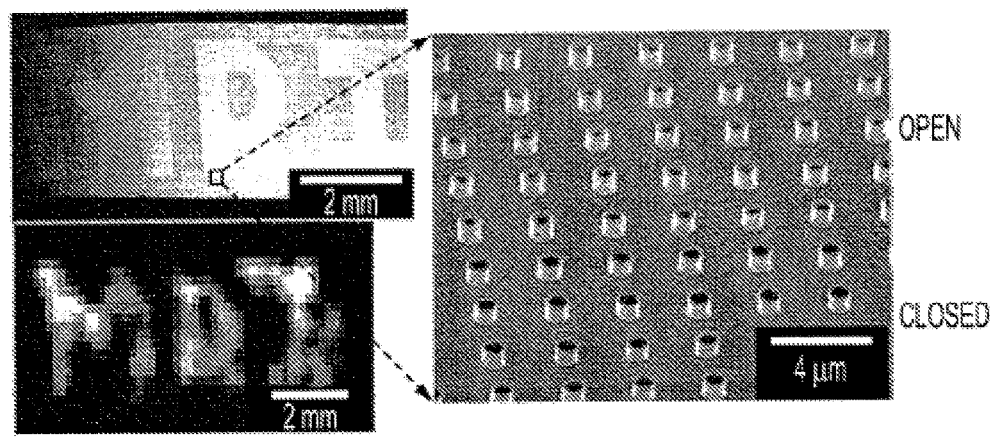

A spectrally distinct physiological "smart" indicator may also be formed by either encapsulating the MRS, or filling its reserved spaces, to inhibit internal diffusion or flow (as shown in FIGS. 17 and 23E), while leaving the far-field spatially trackable image-dephasing capabilities unaffected. In the encapsulated MRS, the frequency-shifted signal would be limited to the signal produced by any NMR susceptible nuclei encapsulated within the reserved space of the MRS. If the diffusion-inhibiting or convection-inhibiting material is chosen to be vulnerable to specific enzymatic attack, or to dissolution beyond a certain temperature or pH, subsequent fluid diffusion or convection could effectively and irreversibly "turn on" their spectral signals.

h. Far-Field Contrast Characteristics ($T_2^*$ Contrast Agents)

The MRS simultaneously provides frequency-shifted magnetic resonance contrast, as well as a more conventional $T_2^*$ contrast function, by virtue of the magnetic field generated by the magnetic materials of the MRS at relatively far distances from the MRS in the far-field region. The $T_2^*$ contrast may be superior to comparably-sized existing MRI contrast agents since the MRS may be constructed by using a top-down microfabrication method that is compatible with using high magnetic moment materials.

Although the magnetic fields induced by the MRS in the near-field region may be essentially uniform, the external magnetic fields in the far-field region exhibit rapid spatial decays in magnitude that manifest themselves as frequency-broadened, but unshifted, background signals seen in measured experimental spectra (for example, see FIGS. 11G-11J, 12-15, 18D). This broadening is due to the transverse magnetization dephasing caused by the spatially varying external magnetic fields, resulting in a shortened $T_2^*$. Therefore, the MRS, like any other magnetic particle, may function as a $T_2^*$ contrast agent.

Figure 24A:
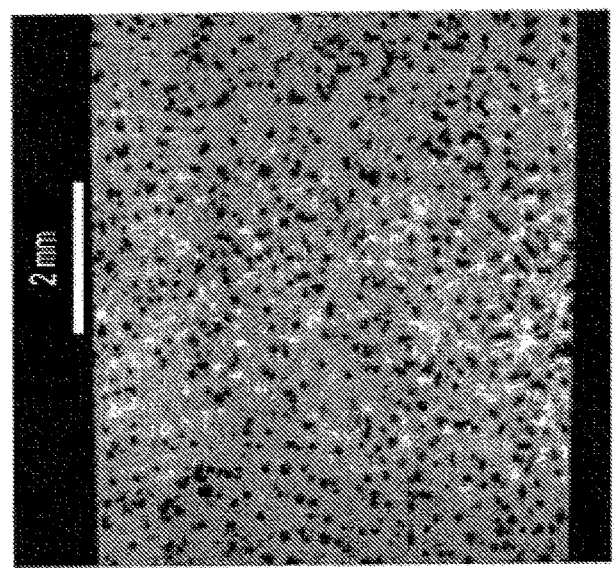
FIG. 24A is an image of a gradient-echo MRI showing hypointense $T_2^*$ contrast (dark spots) surrounding locations of embodiments of the hollow cylinder magnetic resonance structures.

An MRI image of an agarose imaging phantom marked with the hollow cylindrical MRS, shown in FIG. 24, identifies the spatial locations of the structures as darkened spots that are similar in appearance to the $T_2^*$ contrast spots of existing superparamagnetic iron oxide (SPIO) nanoparticle contrast agents. This SPIO-like contrast is not surprising given that when imaged at typical magnetic resonance spatial resolutions, which exceed nanostructure sizes by orders of magnitude, a hollow shell and a solid particle present similar dipolar external field profiles, and $T_2^*$ contrast depends only on magnetic moment. A comparison of the MRI image of FIG. 24 with MRI images of similarly-sized solid magnetic particle contrast agents suggests that the contrast from individual MRS may be resolved within the typical resolution of magnetic resonance images, and that many of the dark spots shown in FIG. 24 are the contrast from individual MRS. The MRS may therefore function as both a spatial and spectral magnetic resonance contrast agent with magnetic dipolar magnetic fields providing spatial contrast in the far-field region and essentially uniform magnetic fields within the reserved space providing spectral contrast within the near-field region.

i. MRS Medium

The MRS generates contrast by frequency shifting the water protons and other NMR-susceptible nuclei within a fluid medium. The fluid medium may be explicitly included as a part of the MRS. The MRS may additionally include a medium in which one or more of the MRS is dispersed. Non-limiting examples of a medium include a nonmagnetic fluid or a non-magnetic gel. The MRS may be dispersed in a fluid medium such as water.

3. Method of Making MRS

The MRS may be fabricated using any known method. Because of the strong dependence of the frequency-shifting behavior of the MRS on its geometry, the fabrication methods used to produce the MRS by necessity must inherently produce a MRS with very low variation in MRS geometry or composition. Further, in order to produce a consistent frequency shift between individual MRS, the fabrication methods should consistently produce MRS with little variation from individual MRS to MRS.

The MRS may be produced using top-down methods and bottom-up methods. Although the top-down methods produce the MRS, with typically accurate structural definition and low inter-structural variability, top-down methods may be more expensive and equipment intensive to implement. Bottom-up methods may be less expensive and equipment-intensive than top-down methods, but produce the MRS with a relatively higher inter-structural variability. Further, the bottom-up fabrication methods may be compatible with a more limited range of materials compared to top-down methods.

Particle complexes can be surface micromachined in various different ways that may, for example, include various combinations of metal evaporation, sputtering, electroplating depositions, and various lithographic processes together with various wet and dry etching processes.

In order to generate the essentially uniform magnetic fields used to induce the detectable and consistent frequency shifts of the MRS, the geometry of the MRS is defined as a relatively exact shape. As a result, the fabrication methods used to produce the MRS must satisfy relatively stringent conditions on the structure geometry in order to produce magnetic structures with highly consistent size and composition. Moreover, for any embodiment in which an ensemble of the MRS is used, the level of inter-particle variability may be reduced to avoid any substantial broadening of the overall spectral signal from the ensemble.

a. Top-Down Fabrication

The MRS may be produced using a top-down fabrication method. The top-down fabrication method may include at least one spatial patterning step in the process. The advantages of using top-down fabrication methods to produce the MRS may include more directly engineered properties and increased functionality. Top-down fabrication, such as lithographic techniques, may be used to produce MRS with high material purity and low variation in MRS geometry, resulting in highly consistent frequency-shifting behavior from among individual MRS.

The top-down fabrication method may be a micromachining or microfabrication method, which may fabricate a structure having a size scale on the order of micrometers or less on a substrate. The top-down fabrication method may also be a nanofabrication technique. The MRS may be produced by the spatial patterning of a layer or layers of material on the substrate using a technique such as a lithographic technique. The lithographic technique may be photolithography, electron beam lithography, other charged particle beam lithography, deep-UV lithography, extreme-UV lithography, and x-ray lithography. Other non-limiting examples of microfabrication techniques include metal evaporation, ion-milling, sputtering, micro-imprinting and nano-imprinting, electroplating, and wet and dry etching. The microfabrication method may be used to fabricate structures ranging in overall size as defined above.

The top-down method may be a resputtering technique used on photolithographically prepatterned substrates. Often regarded as an undesirable by-product of ion milling, the controlled local redeposition of back-sputtered material may be exploited to yield scalable, large-area, parallel fabrication of accurately defined free-standing nanostructures.

As a result of being made by the top-down fabrication method, the MRS may possess low cross-structural variation in size or composition. Any geometrical or compositional variation from structure to structure may induce unintended frequency shifts from one structure to the next. These unintended frequency shifts may further cause a broadening and degrading of the NMR spectral peaks from signals integrated over ensembles of MRS.

(1) Top-Down Fabrication of Dual-Disk MRS

Figure 3:
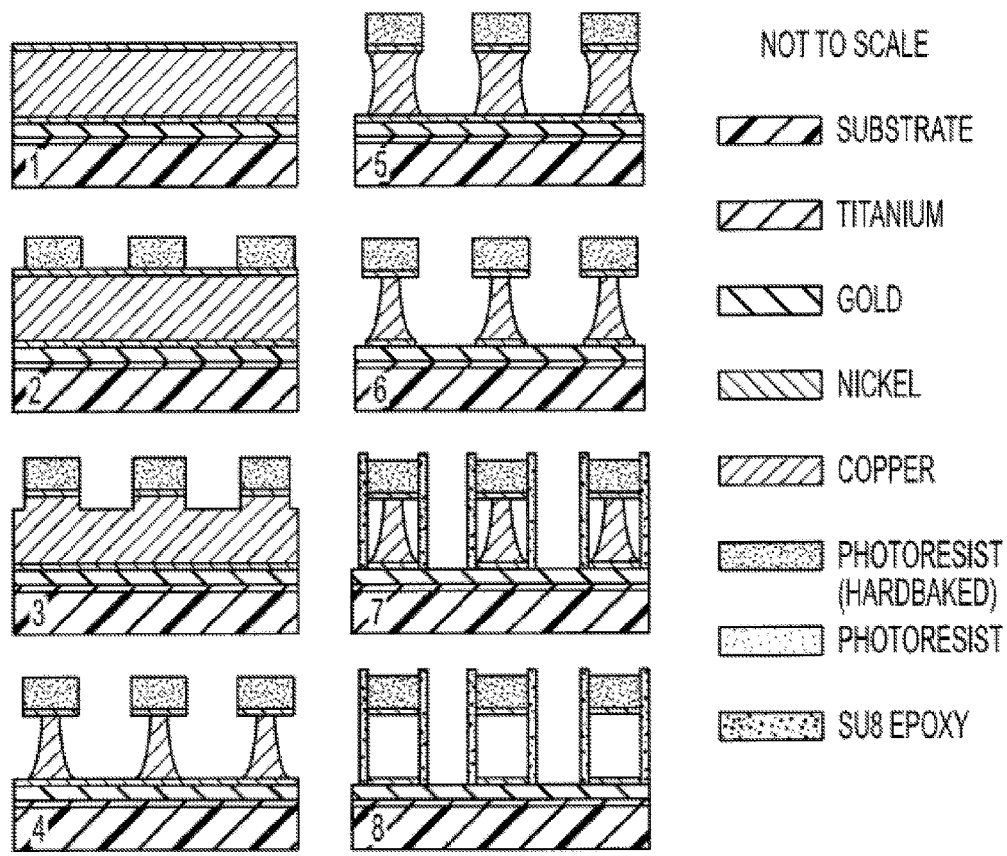
FIG. 3 is an illustration of a method of manufacturing magnetic series of intermediate structures produced during an embodiment of a method of manufacturing magnetic resonance microstructures.

The dual-disk MRS may be fabricated using any one of at least several top-down fabrication techniques. FIG. 3 is a schematic illustration of an exemplary embodiment of a top-down fabrication method for the production of the dual-disk MRS. In this embodiment, titanium and gold layers are evaporated onto a wafer substrate and a nickel/copper/nickel sandwich layer may be either electroplated or evaporated on top of the gold layer at step 1. A permanent mask layer is formed on top of the outer nickel layer by spincoating, patterning, exposing, developing, and hardbaking a photoresist material at step 2. The top nickel layer and an upper fraction of the copper layer are ion milled through at step 3. The copper layer is then wet-etched down to the bottom nickel layer, but stopped before etching through the central copper support at steps 4. Photoresist is spincoated around the sides of the structures at step 5. The top nickel layer is used as a photomask so that subsequent photoresist flood exposure and development leaves photoresist remaining only between the nickel layers. The spincoating at step 5 protects the top nickel layer and patterns the bottom nickel layer for etching. The base nickel layer is wet etched and the internal photoresist is removed at step 6. The external support posts, made of SU8 epoxy, are photopatterned at step 7, and the remaining copper between the nickel layers is wet etched away at step 8.

Figure 4A:
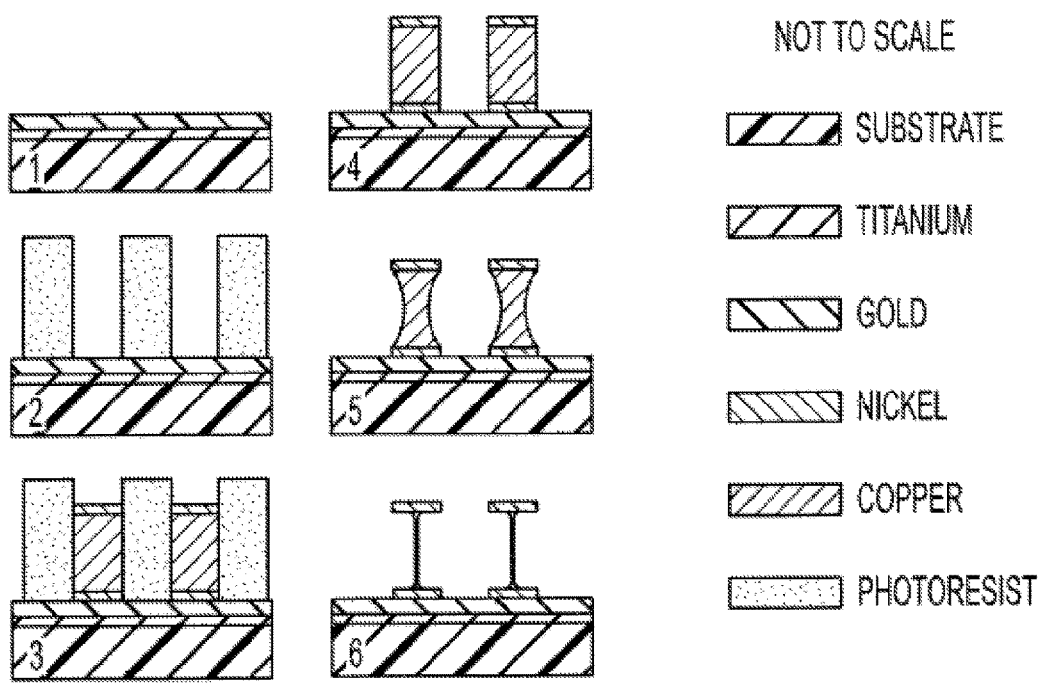
FIG. 4A is an illustration of a method of manufacturing magnetic series of intermediate structures produced during another embodiment of a method of manufacturing magnetic resonance microstructures.

FIG. 4A is a schematic illustration of another embodiment of a top-down fabrication method used to produce an array of dual-disk MRS. In this embodiment, titanium and gold are evaporated onto a wafer substrate at step 1. A thick layer of photoresist is spincoated and patterned at step 2. Successive layers of nickel, copper, and nickel are electroplated into the photoresist mold at step 3. The photoresist mold is dissolved at step 4. A copper wet etch is initiated at step 5, and stopped in time to leave a central copper post at step 6.

Figure 4B:
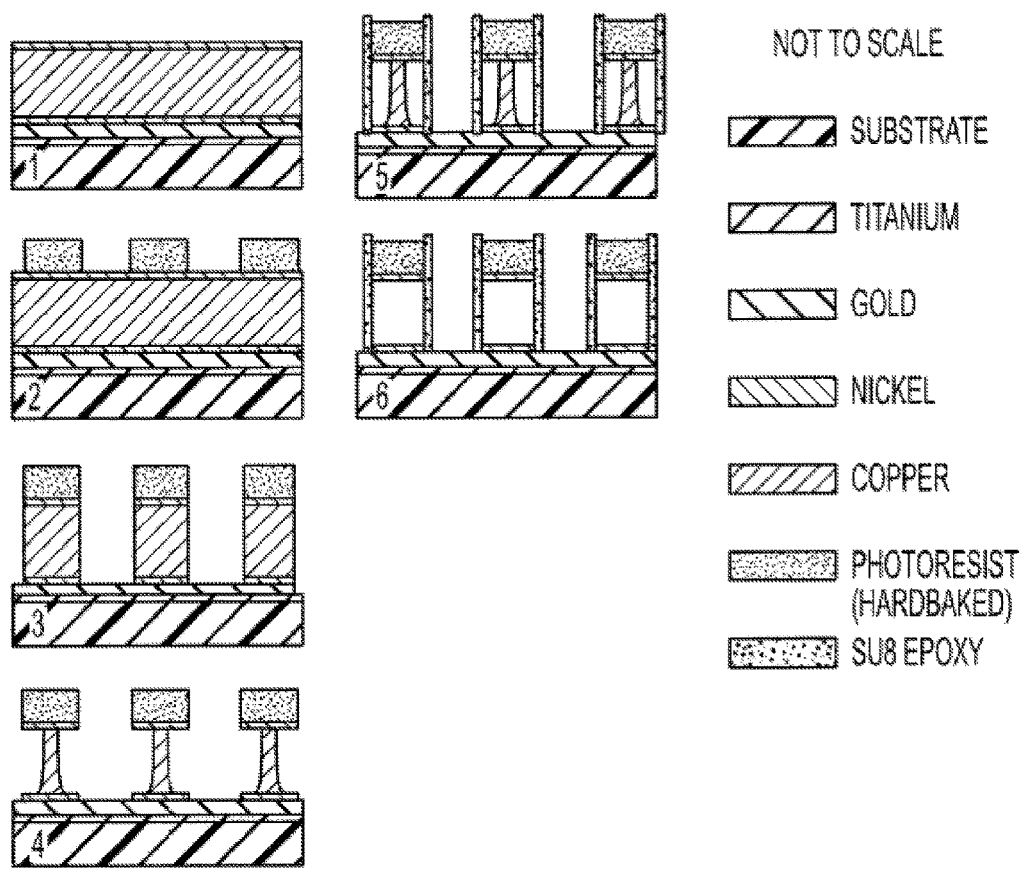
FIG. 4B is an illustration of a method of manufacturing magnetic series of intermediate structures produced during yet another embodiment of a method of manufacturing magnetic resonance microstructures.

FIG. 4B is a schematic illustration of yet another embodiment of a top-down fabrication method used to produce an array of dual-disk MRS. In this embodiment, titanium and gold are evaporated onto a wafer substrate and successive layers of nickel, copper, and nickel are elactoplated or evaporated onto the substrate at step 1. A permanent mask layer is formed by spincoating, patterning, exposing, developing, and hardbaking photoresist at step 2. The top nickel layer, copper layer, and base nickel layer are ion-milled through followed by an angled ion-milling to remove redeposited or resputtered material on the structure side walls at step 3. The copper layer is wet etched partially, leaving a central post support at step 4. If external supports are desired, SU8 epoxy support posts may be photopatterned at step 5 and the remaining copper may be wet-etched away at step 6.

Figure 4C:
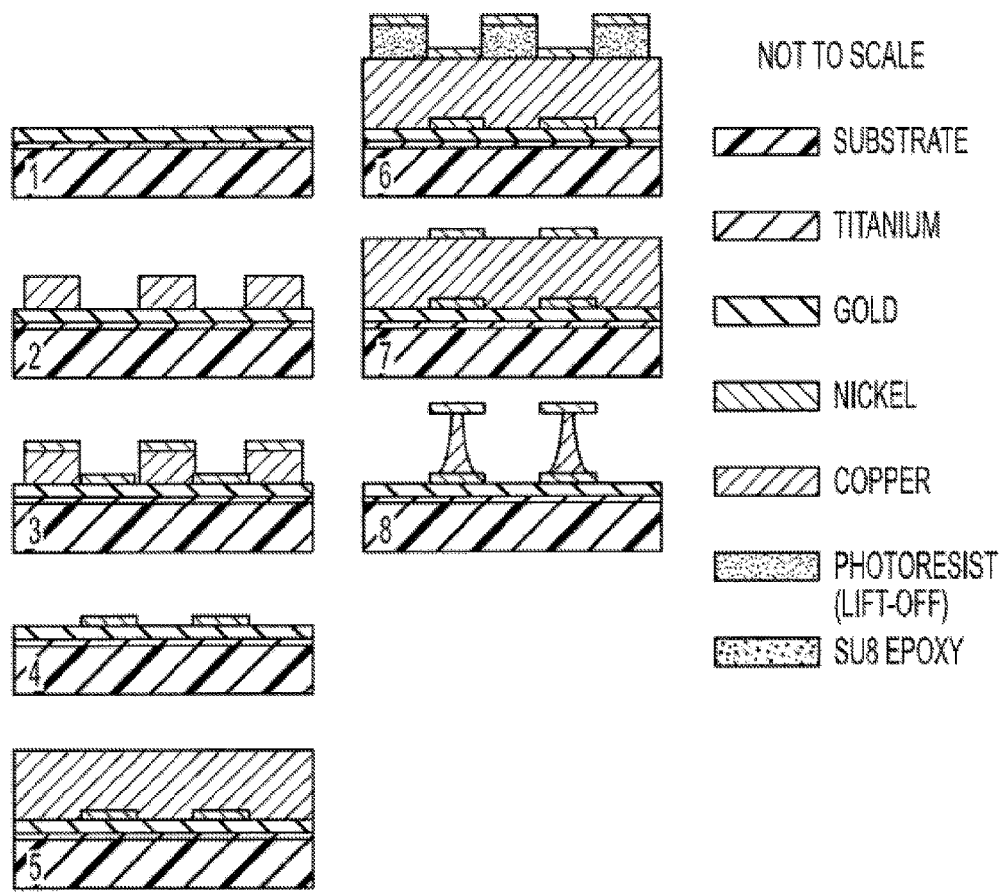
FIG. 4C is an illustration of a method of manufacturing magnetic series of intermediate structures produced during still another embodiment of a method of manufacturing magnetic resonance microstructures.

FIG. 4C is a schematic illustration of still another embodiment of a top-down fabrication method used to produce an array of dual-disk MRS. In this embodiment, titanium and gold are evaporated onto a wafer substrate and successive layers of nickel, copper, and nickel are electroplated or evaporated onto the substrate at step 1. A liftoff resist layer is formed by spincoating, patterning, exposing, and developing photoresist at step 2. A nickel layer is evaporated at step 3, and the lift-off photoresist layer is removed at step 4. Copper is evaporated or electroplated at step 5, and steps 2 and 3 are repeated at step 6. The lift-off photoresist layer is again removed at step 7. The copper is wet-etched at step 8. Alternatively, another layer of patterned photoresist may be formed, and then the nickel layer may be ion-milled prior to the wet etching of the copper in step 8. If desired, external support posts may be formed using similar methods to those described above.

Figure 38:
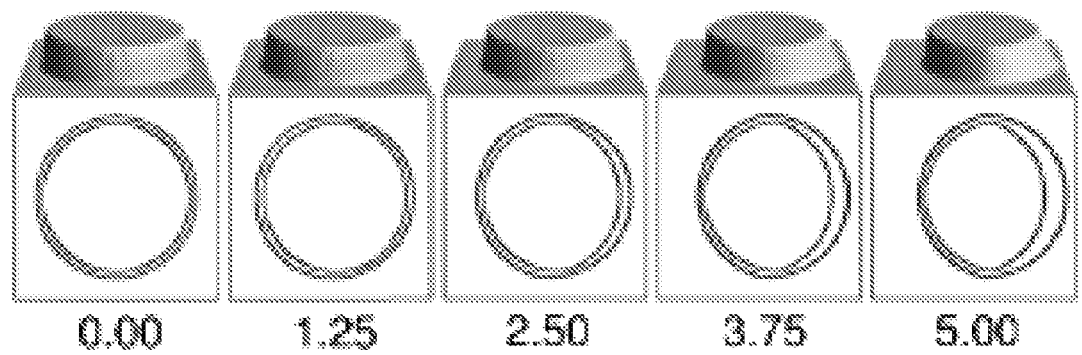
FIG. 38 are drawings illustrating the effect of the radial distance from the wafer center on the profiles of evaporated lift-off patterned deposits during an embodiment of a fabrication process for a dual-disk magnetic resonance structure.
Figure 39:
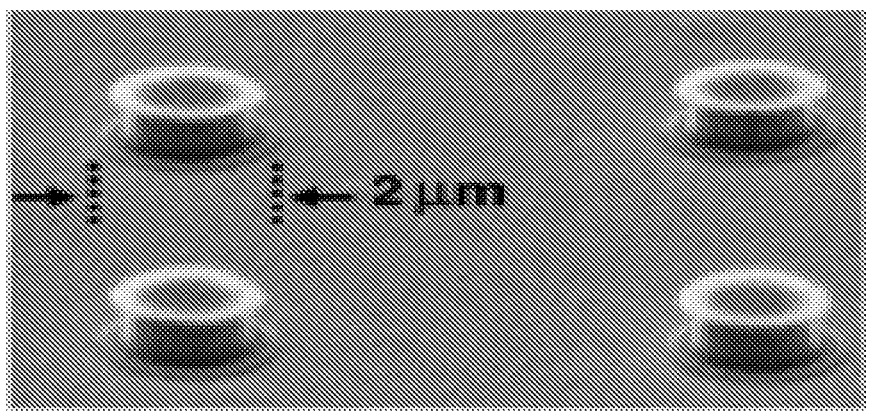
FIG. 39 is a scanning electron micrograph of a trilayer evaporated nickel-copper-nickel cylindrical stacks resulting from an embodiment of a fabrication process for a dual-disk magnetic resonance structure.

FIG. 37A-37E is a schematic illustration of an additional embodiment of a top-down fabrication method used to produce an array of dual-disk MRS. In this embodiment, titanium and gold are evaporated onto a wafer substrate and circular openings with re-entrant undercut sidewall profiles are patterned into a double-layer resist stack consisting of an isotropically developing lift-off resist (LOR) beneath a normal photosensitive resist layer at step 1. To reduce undesired lateral displacement and distortion of evaporated structures that result from nonperpendicular evaporation incidence angles, a thin photoresist layer of no more than 1 µm thickness is used and the LOR layer height reduced to just 1.25 times the desired total height of the evaporated metal stack. At step 2, the base nickel, sacrificial copper, and top nickel layers are evaporated sequentially with all evaporation sources positioned directly beneath the wafer center to ensure correctly overlaying metal layer alignment. The copper source may be of a larger size than the nickel source to ensure that the deposited copper layers are of slightly greater diameter than the deposited nickel layers to avoid overlap of the nickel layers down the side of the copper layer. As the metal deposition proceeds in step 2, metal build-up around the photoresist sidewalls shrinks the mask hole diameters. The resist mask is removed in step 3, yielding final circular stacks that are not right cylinders but tapered conical frustums, as shown in FIG. 38. However, the effect of this tapering is corrected for by depositing a thinner top nickel layer than the base layer in step 2 of FIG. 37. A timed copper wet-etch may be used in step 4 to form single copper central posts between the upper and lower nickel disks. Alternatively, a short selective copper wet-etch may be used to expose the edges of the base nickel layer, providing contact area for external spacer posts that are patterned before the remaining copper is removed, as in step 5. A scanning electron micrograph of dual-disk MRS resulting from this fabrication process are shown in FIG. 39.

Various alternative permutations and combinations of the steps of the exemplary top-down fabrication embodiments shown above could equally well be used to construct dual-disk magnetic resonance structures, solid single-disk magnetic resonance contrast agents, and any other magnetic resonance structure described above. The particular steps selected may depend on factors including the absolute structure sizes and aspect ratios. Such other manufacturing techniques and structures made thereby are included within the various top-down embodiments.

The materials selected for fabrication of the MRS are not limited to the materials disclosed in the exemplary top-down fabrication methods, but may be any magnetic and/or non-magnetic material described previously. Further, the MRS produced using a top-down fabrication method may further incorporate steps to fabricate one or more coatings, including an oxidation or corrosion barrier, a mechanical strengthening layer, a non-toxic coating, a biologically inert coating such as titanium, or a coating to facilitate common bioconjugation protocols such as gold.

The various embodiments of the MRS are not limited to those produced by only the top-down methods described above or to these specific top-down methods of manufacture.

(2) Top-Down Fabrication of Hollow Cylinder MRS

The hollow-cylinder MRS may be fabricated using any one of at least several top-down fabrication techniques. The nanoscale lateral definition of the high-aspect-ratio walls of the hollow cylinder MRS may be challenging to achieve using the traditional top-down fabrication methods such as the various planar microfabrication methods described above. The hollow cylinder MRS may be fabricated using a top-down technique that incorporates an unconventional local resputtering of a prepatterned substrate. This local resputtering fabrication method includes the novel step of ion-milling away a thin magnetic layer previously evaporated onto a substrate patterned with an array of solid cylindrical posts. During the ion-milling, a fraction of the magnetic material emitted from the substrate redeposits on the post sidewalls. By dissolving the post material, cylindrical magnetic nanoshells having a highly uniform cylinder wall thickness are formed. This uniformity of cylinder wall thickness over the full length of the cylinder results in well-defined and sharp NMR spectral peaks, as illustrated in FIG. 19B.

Figure 20A:
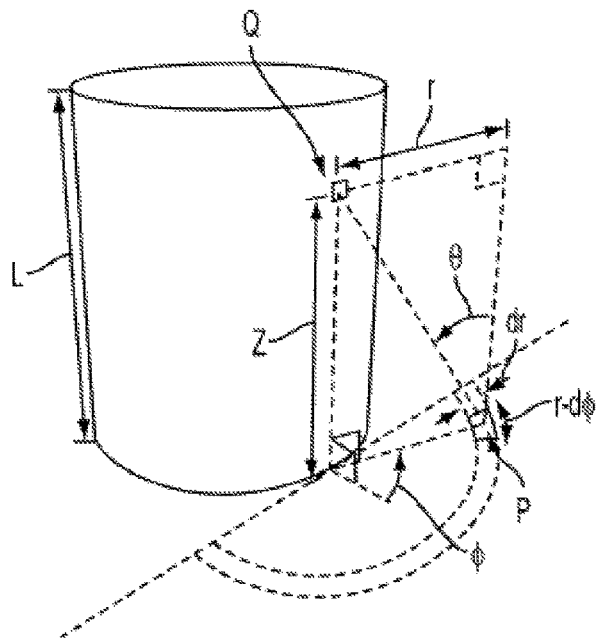
FIG. 20A is a drawing that illustrates the geometrical quantities used in equation X (sputtering equation).

FIG. 20A summarizes the geometry used for the following description of the sputter-coated wall thickness as a function of cylinder height z, up the side of a cylindrical post. The sputtered coating may naively be expected to be much thicker at the base of the post than at the top of the base since points near the base are closer to the source of sputtered substrate atoms than those regions higher up the post. However, because the sputtered atom distribution is not isotropic with respect to height above the substrate, the resputtered wall thickness is unexpectedly uniform. According to linear collision cascade theory, sputter distributions are to first order proportional to $\cos \theta$, where $\theta$ is the angle between the direction of sputtering and the normal of the substrate surface. Sputter distributions have been shown to possess under-cosine distributions, cosine-like distributions, and over-cosine distributions depending on the incident ion energies. The angular dependencies of the sputter distributions may therefore be generally approximated as proportional to $\cos^m \theta$, with values of m below or above unity representing under- or over-cosine distributions, respectively.

Referring back to FIG. 20A, a normally incident ion beam may remove $N_s$ substrate atoms per unit area or an equivalent amount of $N_s r dr d\varphi$ atoms from a differential substrate element P. At a distance d away from the substrate element P, the substrate element P yields an atom fluence per unit area of $n_s(d) \cdot \cos^m \theta$. The proportionality coefficient $n_s(d) = (m+1) N_\Sigma \rho \delta \rho \delta \varphi / (2\pi \delta^2)$ may be determined by normalizing the integrated fluence through a hemispherical surface of radius d that is centered on substrate element P, using the number of atoms emitted. Including the projection factor $\cos \varnothing \sin \theta$ to account for the angle between the atom fluence and the cylinder surface normal, the number of atoms striking the cylinder per unit area at some representative point Q may then be expressed as $z^m \cdot (m+1) \cdot N_s \cdot \cos \varnothing \cdot r^2 dr d\varnothing / (2\pi (r^2 + z^2)^{(3+m)/2})$, where $\cos \theta \sin \theta$ and the distance PQ, are expressed in terms of r and z. Integrating over the half of the substrate visible from point Q then gives the total number of atoms $N_c$ hitting the cylinder per unit area at height $0 < z < L$ as expressed in Eqn. (9):

$$N_c(z) = N_s \frac{z^m (m+1)}{\pi} \int_0^R \frac{r^2}{(r^2 + z^2)^{(m+3)/2}} dr \qquad (9)$$

where R is a measure of the effective substrate target size. As R approaches infinity, physically approximated by $R \gg L$, for all $m > 0$, $N_c$ reduces to $N_s \Gamma(m/2) / (2\pi^{1/2} \Gamma((m+1)/2))$ where $\Gamma$ denotes the gamma function. Under these assumptions, $N_c$ becomes independent of height, implying a uniformly thick wall coating.

Moreover, due to the sputtering anisotropy, approximately uniform coatings result from using effective target substrate sizes R that are only a few times larger than L. For example, a cosine sputter distribution gives $N_c(z) = (N_s/\pi)[\arctan(R/z) - (R/z + z/R)^{-1}]$, implying a cylinder wall that deviates from its average thickness by no more than ±10 percent over the entire cylinder length for R/L values that are greater than about 7. Similarly, for a $\cos^2\theta$ sputter distribution, $N_c(z)=(N_s/\pi)(1+(z/R)^2)^{-3/2}$, implying similar wall-thickness uniformity for R/L values that are greater than 3. The sputtering anisotropy therefore may facilitate efficient and parallel processing of relatively closely packed arrays of structures on a substrate. However, as R/L decreases below the threshold values discussed above, increasingly peaked sputter distributions and higher ion beam energies may be necessary to maintain sufficient uniformity of the cylinder wall thickness.

Because excessively high beam voltages are not required to produce hollow cylindrical MRS, externally coated arrays of cylindrical posts may be used instead of internally coated arrays of cylindrical holes. Although the internal coating of cylindrical holes may be used to produce ring-like structures, the limited sputter target area of this technique implies a low effective R/L value and a resulting substantial wall thickness variation for all but very short cylinders.

Figure 20B:
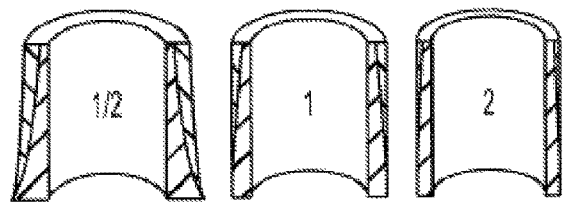
FIG. 20B is a drawing showing the calculated sidewall coating thicknesses for embodiments of the hollow cylinder magnetic resonance structure fabricated using $\cos^{1/2}\Theta$, $\cos\Theta$, and $\cos^2\Theta$ sputter distributions.

FIG. 20B illustrates three examples of wall thickness variations based on solutions of Eqn. (9) for three different sputter distributions. Eqn. (9) also quantifies the absolute wall thickness. For example, simplifying Eqn. (9) for R>>L, a cosine sputter distribution (m=1) gives $N_c/N_s=1/2$. Assuming unit-sticking probability, the shell wall thickness is therefore one-half of the thickness of the original layer ion-milled off the substrate. In this manner, the nanometer-level height control common to planar thin-film layers translates into similar nanometer-level width control of thin, vertically oriented surfaces.

Since the previously described analysis was not necessarily limited to a cylinder, other high-aspect-ratio structures may be similarly fabricated. However, because some alternative magnetic resonance structure geometries may limit substrate visibility, locally differing limits to the R-integral and ø-integral, and possible couplings between the integrals may exist. In addition, Eqn. (9) is strictly valid only for thin coatings in which t<<L. For thicker coatings, the possibility of appreciable time-dependent modification to the surface normal as substantial sidewall material accumulates, ion erosion of the accumulated material, and reflection from accumulated material may be taken into consideration. While these secondary effects may be essentially negligible for the high aspect-ratio thin-walled structures described above, general theory describing these secondary effects are known in the art.

Figure 21A:
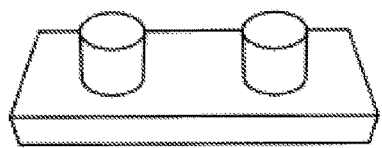
FIGS. 21A-21F are drawings illustrating the intermediate precuts of an embodiment of a fabrication process for hollow cylinder magnetic resonance particles.
Figure 21B:
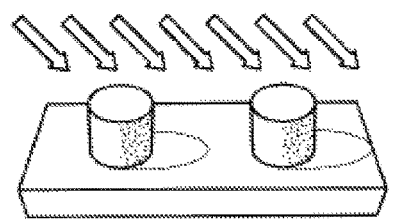
Figure 21C:
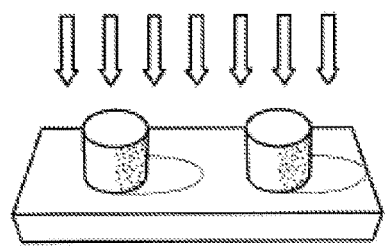
Figure 21D:
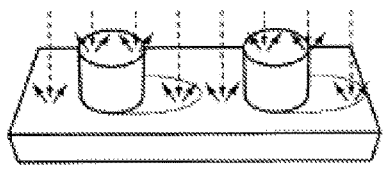
Figure 21E:
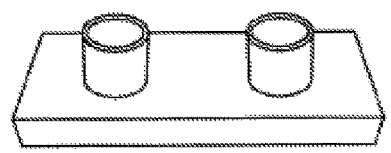
Figure 21F:
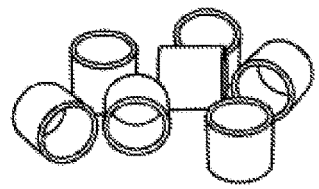

FIGS. 21A-21F provide a schematic illustration of one embodiment of a top-down fabrication process for the production of the hollow cylindrical MRS. Cylindrical posts of radius p are patterned out of a photoresist layer of thickness L atop a sacrificial gold layer, as shown in FIG. 21A. To avoid resist exposure to the ion beam, and to facilitate subsequent structure release, a thin sacrificial copper layer is evaporated obliquely on the substrate and posts, as shown in FIG. 21B, coating the substrate everywhere except within the shadows cast by the cylindrical posts. The desired magnetic material is evaporated as shown in FIG. 21C, and removed from the substrate and the tops of the posts via argon ion beam milling as shown in FIG. 21D leaving behind the redeposited sidewall coatings as described above. A selective wet-etch of the underlying protective copper followed by an acetone resist removal then leaves the desired hollow cylinders as shown in FIG. 21E. Each hollow cylinder at this stage is attached to the substrate around just one half of the base, corresponding to the shadowed sides that did not receive any copper coating previously, holding the hollow cylinders in place on the substrate for further processing, if desired. The cylindrical shells may be removed from the substrate by either a gentle ultrasound treatment or a selective wet-etching of the underlying sacrificial layer (FIG. 21F). Note that the copper layer is not essential in this method, but including the copper layer facilitates the resist removal and provides the option of a subsequent water-based ultrasound release free of any metal etchants or solvents.

For the case of cylindrical posts the magnetic material evaporation may also be performed at an oblique angle in a manner similar to the copper evaporation step shown in FIG. 21B, provided that the substrate is continually rotated throughout the evaporation of the magnetic material. However, if oblique evaporation is used to coat the post sidewalls with magnetic material, this material may also coat the substrate, and therefore still require subsequent ion-milling, subjecting the cylinders to similar sidewall sputter redeposition. The oblique rotating evaporation of magnetic material may be conducted at shallow grazing angles relative to the substrate, but then the shadowing resulting from the shallow grazing angle may limit the general applicability of this technique and the spatial density of structures that may be patterned using this technique. Although coating the substrate with evaporated magnetic material may also be avoided by obliquely shadow-evaporating onto an inversely patterned array of cylindrical holes rather than posts, such geometries may preclude uniformly thick wall coatings. Because of the circular cylinder cross-sections, the line-of-sight penetration depths of evaporant material may vary across each hole, resulting in cylindrical shells whose wall thicknesses taper down from top to bottom.

Figure 22A:
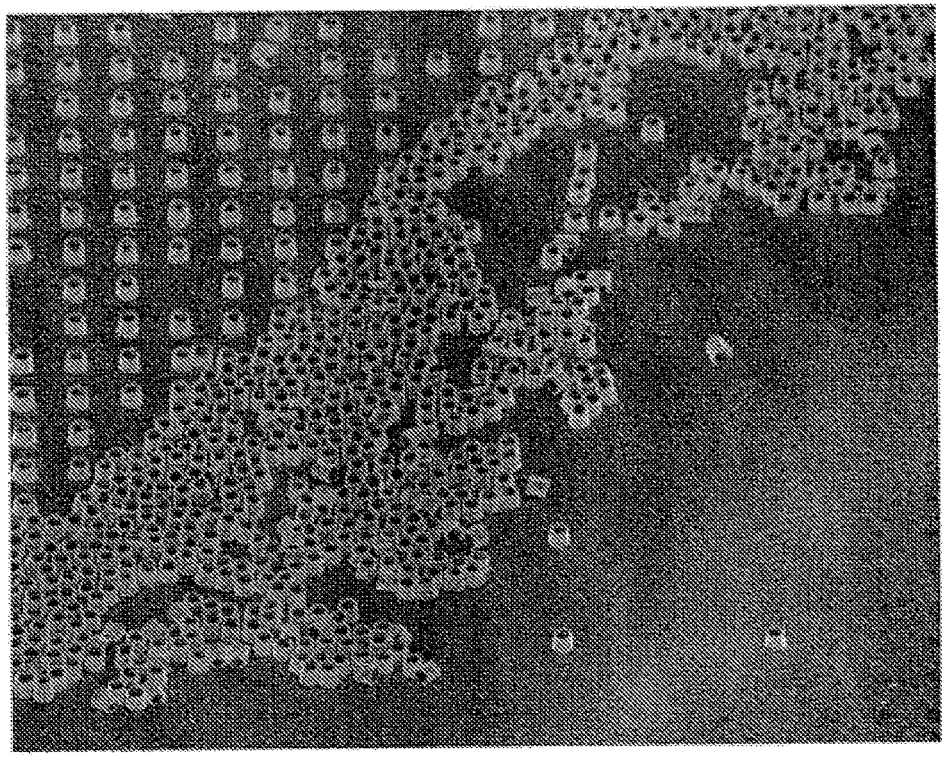
FIG. 22A is an image from a scanning electron micrograph (SEM) of fabricated hollow cylinder magnetic resonance structures produced by an embodiment of a fabrication process.
Figure 22B:
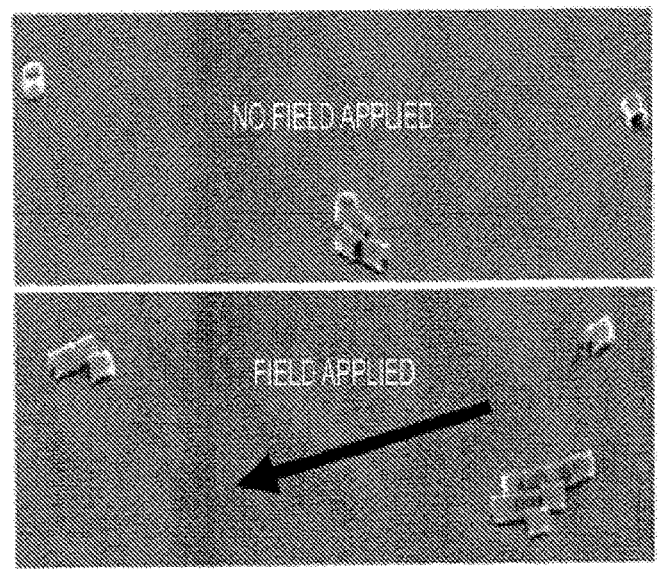
FIG. 22B is an image from a scanning electron micrograph ($\rho \approx 425$ nm) showing an embodiment of a hollow cylinder magnetic resonance structure in the absence of an applied magnetic field (top image) and in the presence of an applied field (bottom image).

FIG. 22A is a scanning electron micrograph (SEM) of a sample array of fabricated nickel hollow cylindrical MRS that have undergone a partial wet-etch release. The cylinders have wall thicknesses of about 75 nm, cylinder inner radii of about 1 µm, and an aspect ratio (L/2ρ) of about 1.2, implying wall height-to-thickness aspect ratios L/t of about 30. Despite having thin walls, the hollow cylindrical structures are physically robust, self-supporting structures that are resistant to damage during either wet-etch (see FIG. 22A) or ultrasound release (see FIG. 22B). In FIG. 22B, the hollow cylindrical structures were removed from the substrate using ultrasound, transferred into a vial of water, and then pipetted out onto fresh substrates. When the fresh substrates were placed into an applied background magnetic field, the hollow cylindrical MRS aligned with the applied field direction due to the anisotropy of the hollow cylinder's structure imparted by the high L/t aspect ratios of the structures, as shown in FIG. 22B.

These fabrications of hollow cylinder MRS are not limited by size, scale, dimensions, materials and/or various layers that may be used as coatings and adhesion layers.

(3) Top-Down Fabrication of Solid Particulate MRS-Single Disc

The solid particulate MRS agent may be microfabricated through the top-down method. The top-down fabrication can include the micromachining methods of using metal evaporation, ion-milling and lift-off micropatterning techniques. Photolithographic patterning may be used to generate arrays of many of millions of solid particulate MRS to be simultaneously fabricated. A substrate may be used to generate the solid particulate MRS.

An exemplary process of generating solid particulate MRS is shown in FIG. 41. A 10-nm thick titanium adhesion layer may be evaporated onto a supporting substrate followed by a 100-nm thick sacrificial copper layer and a 100-nm thick gold layer at step 1. Also at step 1, a double layer of resist may be spin-coated over the titanium-coppergold trilayer with a photosensitive top layer of resist and a bottom layer of isotropically developing lift-off resist. This structure may be exposed through a mask containing an array of 2 µm-diameter circular holes at step 1 as well. The patterned development and dissolution of the top resist layer results in the isotropic development and dissolution of those physically exposed portions of the lift-off resist, creating the profile shown in step 1. An approximately 300-nm thick layer of iron and/or nickel may then be evaporated followed by an evaporation of a 200-nm thick layer of gold at step 2. The metal deposited on the top of the photoresist is physically disconnected from metal deposited on the substrate in this step, and subsequent removal of the resist bi-layer at step 3 may remove the top metal layers while leaving the metal bilayer on the substrate untouched. A 100-nm deep argon ion-milling may then remove the exposed gold on the substrate and about half of the top 200-nm gold layer at step 3. During this ion-milling process some of the back-sputtered gold ion-milled from the substrate may redeposit on the iron/nickel sidewalls, leaving magnetic disks of nickel and/or iron completely encased in gold at step 4. The gold encasing the nickel and/or iron may be in the form of a 100-nm thick top and bottom gold coatings, and approximately 50-nm thick gold coatings around the circumferential sidewalls of the disks. Finally a selective wet-etch of the underlying copper or treatment with ultrasound may be used to release the particles from the substrate (not shown). The particles may also be washed to remove any remaining etchant solution.

These fabrications of solid particular MRS are not limited by size, scale, dimensions, materials and various layers may be used as coatings and adhesion layers.

b. Bottom-Up Fabrication

The bottom-up method may be a chemical synthesis technique, which may not include at least one spatial patterning step. The bottom-up method may use tightly-controlled process specifications, or an additional sorting step to select a sub-group of MRS having acceptably similar geometric and compositional properties.

Where only a few distinct spectral shifts induced by the MRS are to be used in magnetic resonance visualization at any one time, it may be possible to sacrifice some fabrication precision in order to make use of bottom-up fabrication techniques. Certain well-controlled chemical syntheses may possess a high enough degree of control and monodispersity to provide practical fabrication methods for the MRS.

A large batch of the MRS may be synthesized and then separated and/or filtered step to select out only those structures from the large batch that have geometrical shapes that fall within a suitably narrow band of sizes and shapes. The typically higher throughput of chemical synthesis methods may render this approach suitable for some applications.

A filtering/separation step may be accomplished by taking advantage of the magnetic moment and magnetic materials of the MRS. For example, with a batch of structures fabricated using a bottom-up method suspended in some fluid, an external magnet field gradient may be applied to create a force on the structures that drags them through the fluid. In this example, the speed of the particles moving through the fluid may be governed by a balance between the drag force of the fluid on the particles and the translational magnetic force acting on the particles. However, the magnetic and drag forces may depend on the shapes and magnetic moments of the particles to differing degrees. Therefore, after moving through the fluid under the influence of the applied magnetic field gradient, the differently sized/shaped/composed particles may be spatially separated within the fluid, and a sub-group of the particles may be specifically selected from the fluid based upon their location within the fluid. The particles within this particular sub-group may exhibit a suitably high degree of monodispersity and may have the desired shapes.

The MRS may be formed using a template structure such as a porous membrane substrate formed from a porous material known in the art such as anodic alumina. The cylindrical pores within the template structure may be filled with one material, the template structure may be chemically treated to enlarge the pore sizes, forming annular rings between the cylinders and the eroded template structure within each filled pore. The annular ring may then be filled with a magnetic material and the inner material may be chemically eroded to form hollow cylindrical structures that may be removed by again eroding the template structure by selective chemical removal.

To fabricate the MRS, an ensemble of solid cylindrical rods suspended in a solution may be chemically coated with a magnetic material using a chemical method such as electroless plating, or galvanic deposition. For example, commercially available gold nanorods may be suspended in an electrolyte solution. However, prior to chemically coating the cylinders, the ends of the cylinders may be selectively chemically passivated to ensure that the plating of the magnetic material occurred only around the sides of the cylinders. The central cylinders may then be selectively etched out, leaving only the plated cylindrical shell. Because typical existing cylindrical rods exhibit considerable variation in diameter and length, an optional filtering/separation step may be performed as previously described to select a sub-group of hollow cylinders having the desired shape and composition.

4. Methods of Use

The MRS may be used in a variety of applications, in addition to providing magnetic resonance frequency-shifting contrast. On a small scale, the MRS may be used to mark various objects as a microtag or as a cell marker. The alignment of anisotropic MRS to an applied magnetic field may be used to determine the direction or other characteristics of a flow. On a large scale, the MRS may be installed around the perimeter of a variety of fluid-carrying vessels ranging such as microfluidics channels or blood vessels and used to frequency-shift the fluid passing through the reserved space of the MRS, providing spin-tagged flow for magnetic resonance flow visualization.

Shifts in the Larmor frequency of water protons or other NMR-susceptible nuclei within a near-field region of the MRS during exposure to a resonant electromagnetic pulse may be used to conduct multiplexed color magnetic resonance visualization. Engineered to exploit diffusion and/or fluid flow in some embodiments, the MRS increases existing magnetic resonance sensitivity by orders of magnitude, and reduces the required concentrations of the MRS to well below those of existing contrast agents. The MRS may additionally function as an individually detectable, spectrally distinct micro-tag. With NMR spectral shifts determined by structural shape and composition instead of by chemical or nuclear shifts, the spectral signatures associated with the MRS may be arbitrarily tailored over uniquely broad shift ranges spanning many tens of thousands of parts per million. The MRS having a size scale of micrometers may function as a localized physiological probe, enhancing both magnetic resonance capabilities and basic biological research. The MRS may also be used over a wide range of applications that are analogous to the uses of quantum dots or RFID tags.

a. Dephasing Contrast Enhancement Agents (1) Solid Particulate MRS Contrast Agents The solid particulate MRS may be used as conventional $T_2^*$ contrast agent due to its magnetic materials. The solid particular MRS may be spatially imaged using the same dephasing contrast analysis common to MPIOs. Because the top-down manufacturing technique is amenable to the use of high $J_s$ materials such as iron, the solid particulate MRS contrast agents possess higher magnetic moments for a given particle volume compared to existing contrast agents such as MPIOs. As a result, solid particulate MRS contrast agents may be used to achieve comparable contrast levels at lower concentrations than existing contrast agents such as MPIOs.

(2) MRS with Reserved Space as Dephasing Contrast Agent

In addition to acting as a conventional $T_2^*$ contrast agent, an MRS with a reserved space may be differentiated spectrally using the additional information provided by the NMR-shifting capabilities of the reserved space. For example, the NMR-shift information may be used to distinguish contrast signals from spurious signal voids that confound magnetic resonance imaging using SPIO or MPIO contrast agents. Depending on the size of the MRS, multiple different particle spectra may be acquired simultaneously from a single free induction decay signal following a hard π/2 excitation pulse. Alternatively, magnetic resonance imaging may spectrally resolve the tags separately, as shown for example in FIG. 11.

b. MRS Identity System

The MRS may be used as a microtag to mark a variety of items with a unique color frequency-shift. This frequency-shift may be measured using a MRS identity system. An MRS microtag may be used to mark virtually any item to which one or more MRS may be attached, or a container containing one or more MRS microtags that may be attached. For example, MRS microtags may be used to mark biological cells for cell tracking studies, packages for tracking during shipping, and inventory for industrial inventory control.

Figure 5:
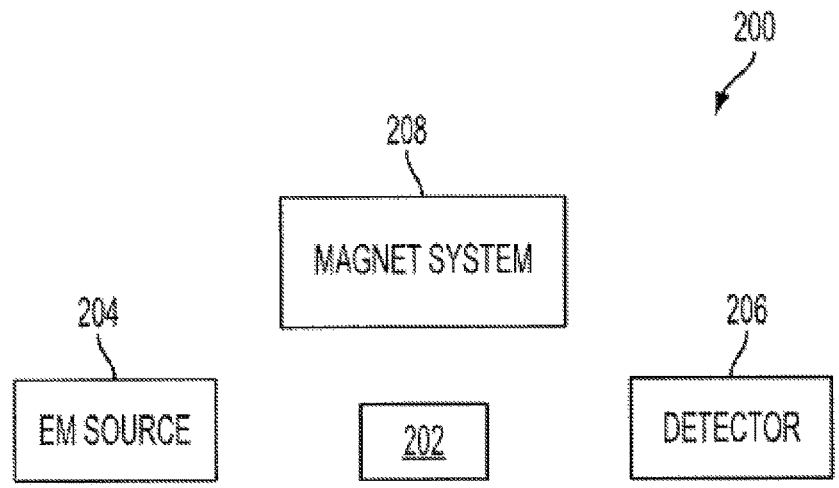
FIG. 5 is an illustration of an embodiment of a magnetic resonance identity system.

FIG. 5 is a system diagram of an embodiment of a magnetic resonance identity system 200. The magnetic resonance identity system 200 includes at least one MRS 202, a source of electromagnetic radiation 204 to illuminate the magnetic resonance microstructure 202 with an excitatory electromagnetic pulse, and a detection system 206 to detect electromagnetic radiation emitted from within the magnetic resonance microstructure 202 after the MRS 202 has been illuminated with the an excitatory electromagnetic pulse. The MRS 202 may be a solid particulate MRS that functions solely as a $T_2^*$ contrast agent, or an MRS with a reserved space that may act as either a $T_2^*$ contrast agent, a NMR-shifting contrast agent, or both. The magnetic resonance identity system 200 may also include a magnetic field generation system 208 to provide a magnetic field in a region suitable for the placement of a sample of interest that may include the MRS microtag.

c. MRS Stent

A stent that includes an MRS with a reserved space may be used to monitor blood flow through the stent as well as remotely monitoring the condition of the stent. Discrete volumes of NMR-shifted water protons created at different times within the reserved space may be visualized using NMR imaging and used to estimate the blood flow speed downstream of the stent. In addition, the magnitude of the NMR-shift may measured and used to determine changes in the condition if the stent collapse or their is distortion of the stent.

The MRS may be installed around the inner or outer perimeter of a stent in order to measure the characteristics of blood flow through the stent. Alternatively, the stent may be entirely composed of the MRS structure. The stent is situated such that the blood flow passes through the reserved space of the MRS.

Figure 25:
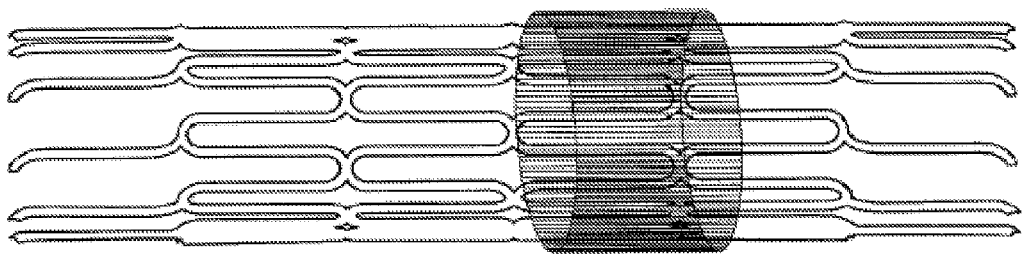
FIG. 25 is a drawing illustrating another of a stent magnetic resonance structure.
Figure 26:
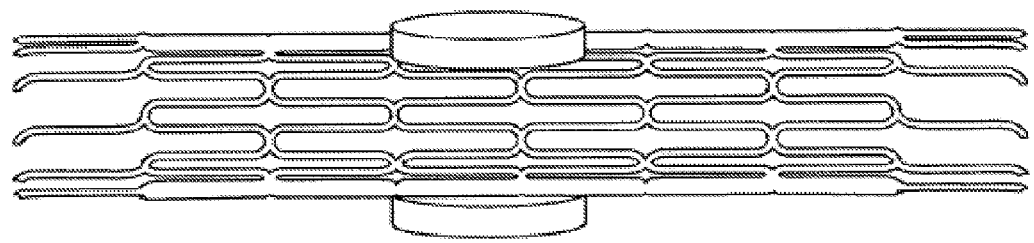
FIG. 26 is a drawing illustrating another embodiment of a stent magnetic resonance structure.

FIG. 25 is a schematic illustration of an embodiment of a hollow cylindrical MRS that functions in conjunction with a stent. In this embodiment, a thin ring-like magnetizable solid structure surrounds or is attached to the inside walls of a stent device. The MRS of this embodiment may also be one or more dual-disk MRS, as shown in FIG. 26. If more than one dual-disk MRS are used, each pair of disks may be situated at the same longitudinal position along the stent, but rotated around the stent's axis of symmetry by different rotations angles. There may also be a plurality of dual-disk MRS arrayed around at different angles to approximate a ring structure.

The particular magnetic resonance structure may be selected based on the type of stent in which the structure is to be used. For example, a dual-disk geometry may be more favorable geometry if the stent device is intended to be inserted in a collapsed position and then expanded via a catheter balloon after the stent is situated in its intended location.

The spectral shifting within the reserved space of the MRS allows the water protons or other NMR-susceptible nuclei in the blood flowing through the MRS to be spin-labeled so that blood flow (both speed and, through frequency-shift-dependent stent diameter indications, mass-flow) can be measured. Such spin-labeling, alternatively also known as spin-tagging, can be performed by, for example, irradiating the MRS with resonant RF electromagnetic pulse to specifically spin-tag NMR-susceptible nuclei within the reserved space. Fluid not resident within the reserved space during a resonant RF electromagnetic pulse would be essentially unaffected by the pulse.

Should the artery or other blood vessel containing a stent narrow, the stent diameter may shrink as a result, causing the NMR frequency shift to be altered, as discussed above and shown in Eqn. (2) and/or Eqn. (7), due to the change in spacing between magnetizable elements. A similar effect may occur if the stent itself was in some way damaged or started to collapse. Thus, the inclusion of MRS within a stent device enables the non-invasive NMR measurement of artery collapse or warning of possible imminent stent collapse.

There may also be multiple NMR spaced at pre-determined intervals longitudinally along the stent in some embodiments of the current invention to provide redundancy, to be used for alternative blood flow speed measuring (for example via time-of-flight techniques), or to increase the contrast signal magnitude. A similar measurement of blood flow within a blood vessel may be non-invasively measured without a stent device by placing the magnetic elements of the MRS arrayed around the outside of a vein/artery or other blood vessel to monitor blood flow within that blood vessel.

d. Spin-Tagging Fluid Flow/Perfusion Imaging

MRS may be situated such that a fluid flows through the reserved space, and a volume of fluid within the reserved space may be frequency-shifted by the uniform magnetic field of the MRS. For a limited period of time after leaving the reserved space, the volume of fluid may retain the shifted NMR frequency, effectively spin-tagging the fluid as it flows. Using magnetic resonance visualization methods described above, the spin-tagged fluid may be visualized and analyzed to determine a variety of flow characteristics such as flow speed.

To perform the spin-tagging of fluid flow, one or more MRS may be situated around the perimeter of a fluid vessel and/or along the length of a fluid vessel and the fluid flowing through the reserved space of the MRS may be frequency-shifted and visualized using magnetic resonance techniques to provide non-invasive visualization of fluid flow. This concept of spin-tagging fluid as it passes through the uniform magnetic field within the reserved space of the MRS structures may be used at a variety of size scales ranging from vessels that are about 1-μm, 2-μm, 5-μm, 10-μm, 20-μm, 30-μm, 40-μm, 50-μm, 60-μm, 70-μm, 80-μm, 90-μm, 100-μm, 200-μm, 300-μm, 400-μm, 500-μm, 600-μm, 700-μm, 800-μm, 900-μm, 1 mm, 2 mm, 3 mm, 4 mm, 5 mm diameter to vessels that are about 5 cm or more in diameter. Fluid flows that may be visualized using MRS spin-tagging methods may include perfusion and other blood flow, industrial fluid flow, and flow in microfluidic systems. For example, applications may include measuring, imaging, or detecting flow within a microfluidic channel or network as may exist in various microchip-based chemical and biological assays (i.e., lab-on-a-chip systems). As another example, the flow in industrial pipes or pipelines may be visualized using spin-tagging of the fluid within the pipes using one or more MRS that may be arrayed externally about the exterior circumference of the pipes, or contained within the pipes or attached to the inner walls of the pipes. Spin-tagging using MRS may further provide flow monitoring capabilities even if the pipes are non-transparent. Flow monitoring capabilities may include observing where fluid subsequently flows, measuring the flow speed, and how the flow speed varies across one or more cross-sections of the pipe or along the length of the pipe.

Figure 28:
FIGS. 28-31 show experimental results for an embodiment corresponding to FIG. 27.
Figure 29:

The MRS may be used to spin-tag discrete volumes of fluid containing NMR-susceptible nuclei such as water protons by exposing the MRS to discretely spaced electromagnetic pulses at the resonance frequency of the MRS. Fluid contained within the reserved volume during each resonant electromagnetic pulse is phase-shifted, and any remaining fluid outside of the reserved volume is unaffected by the resonant electromagnetic pulse. Fluid flowing downstream of the MRS that has been phase-shifted in this may be visualized using magnetic resonance visualization. FIGS. 28 and 29 are MRI images showing the bands of spin-tagged fluid downstream of an MRS. In FIG. 28, both pipes in the figure were exposed to a discrete series of electromagnetic pulses at the resonant frequency of the left MRS prior to MRI scanning. In FIG. 29, both pipes were exposed to a discrete series of electromagnetic pulses at the resonant frequency of the right MRS prior to MRI scanning. Each dark band in the pipes mark the parabolic profile of a spin-tagged volume that has traveled in a laminar flow within the pipe for a short distance downstream from the reserved volume. In addition, because the right hand pipe in FIG. 28 was not exposed to an electromagnetic pulse at its resonant frequency, which is different from the resonant frequency of the left MRS, none of the flow in the right pipe was spin-tagged, resulting in a uniformly light image in the MRI image. The flow in the left pipe in FIG. 29 was not spin-tagged for similar reasons.

Figure 30:
Figure 31:
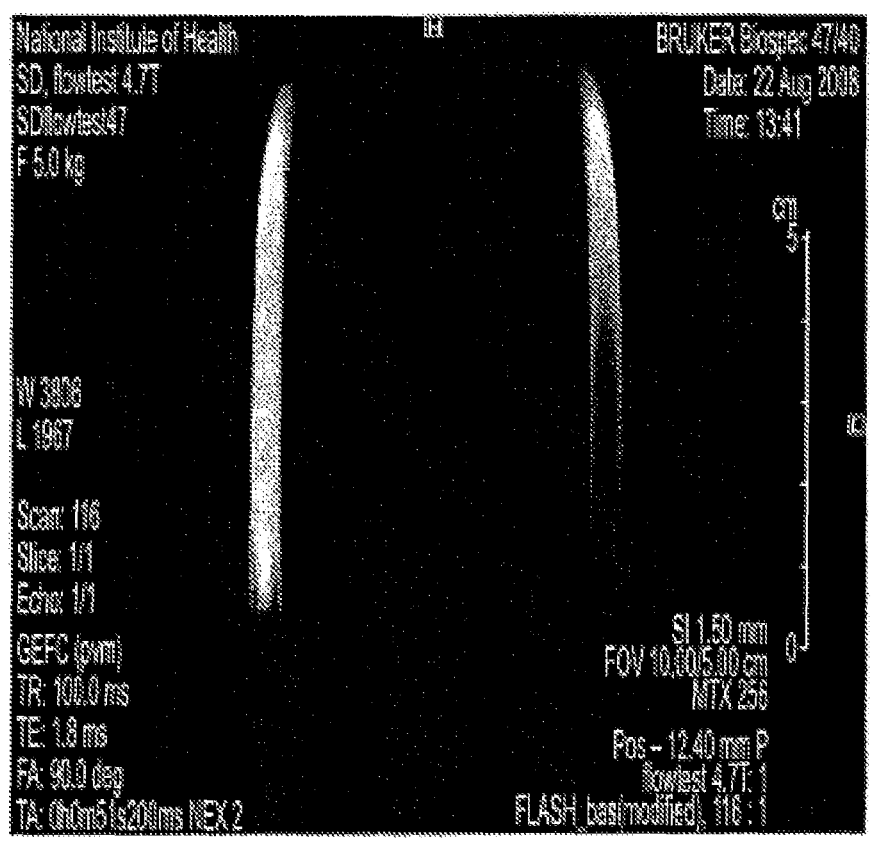

Additionally, the MRS may be used to conduct perfusion studies with multiple spin-labeled streams that are immune to magnetic mixing. Such a process may also be applied to perfusion imaging where the resonant electromagnetic labeling pulses are spaced close enough in time so as to appear continuous in an image, as shown in FIGS. 30 and 31 for the left and right tubes, respectively, where in this case the spin-labeled flow occupying half of each tube is darkened. For example, this technique may be used to show where fresh blood enters the brain and perfuses.

The spin-tagging technique of flow visualization may be used to measure the features of both laminar Poiseuille flow, as well as turbulent flow. Finer flow features such as turbulence, vortex structure, or boundary layer structure may be measured using spin-tagging, so long as the magnetic resonance visualization device used to visualize the spin-tagged flow possessed sufficient resolution.

e. Magnetic Resonance Spatial Calibration Markers/Locators (When Affixed to Substrate)

An array of MRS with known separation distances and angles may be used as a calibration aid for a magnetic resonance device. A set of the MRS might be arrayed in some regular geometrically prescribed arrangement with known spacings and/or angles between the individual MRS in the set, firmly attached to a rigid substrate to provide a spatial calibration of measured distances and angles in a magnetic resonance device. If MRS with reserved spaces are used, MRS with two or more frequency-shifting characteristics may be placed in close proximity within the set, even within the same voxel of the magnetic resonance device, so long as the MRS are separated by at least about twice the maximum dimension of the MRS. Using multi-spectral scanning methods, in which the calibration aid is imaged after each exposure to electromagnetic pulses at each of the resonant frequencies of each subset of the MRS in the calibration aid. A much higher calibration resolution may be achieved than is possible using MRS with uniform contrast properties or existing magnetic particle contrast agents.

In addition, the MRS may be attached to a moving substrate within the field of view of an MRS device. For example, an MRS may be attached to the tip of a surgical instrument such as a catheter, and magnetic resonance visualization may be used to track the location of the surgical instrument non-invasively and/or guide the surgical instrument during a surgical procedure.

If an MRS with a reserved space is attached to a surgical instrument or other moving substrate, the NMR-shifting signal of the MRS may be used to identify the particular moving substrate as it moves within the field of view of the magnetic resonance device. Each of two or more surgical instruments may be marked with MRS with different NMR-shifting signal frequencies and the movements of each surgical instrument may be individually tracked and guided using the multispectral magnetic resonance visualization methods described above. Further, cells or tissues to be targeted by the surgical instruments may be marked with yet another group of MRS having another NMR-shift signal frequency to provide a target for the surgical instruments using multispectral magnetic resonance visualization.

An activatable MRS, described above, may be attached to a moving substrate such as a surgical instrument and used as a smart sensor in which the NMR frequency shift changes as a function of some physiological condition such as temperature, oxygen content, or pH. For example, as the moving substrate is moved within the field of view of the NMR visualization device, such as during a surgical procedure, the NMR frequency shift of the MRS may be monitored to assess one or more physiological conditions in order to monitor the conditions of a surgical procedure or to guide the placement of the surgical instrument.

f. MRS Microtags and Specific Detection/Labeling/Tracking of Biological Cells One or more MRS microtags may be affixed to an object, allowing that object to be magnetically probed and/or recognized using the magnetic resonance visualization techniques described above. Unique combinations of MRS about 1-µm to about 1-mm in overall size may be used to label an object such as a cell, organism, or non-biological object for identification using magnetic resonance scanning. The identification information may be encoded by the combinations of MRS in a manner analogous to RFID-tagging. In addition, by marking each object with one or more different MRS particles having different frequency shifts, different objects may be distinguished from each other in much the same way as regular RFID chips do by marking the object with one or more MRS having a specific known NMR frequency shift, except that the identifying signal is based on a nuclear magnetic resonance measurement. For example, objects of type A may be marked with a MRS having a NMR frequency shift A, and another object B may be marked with a different MRS having a NMR frequency shift B.

The MRS particles and the objects that they label may reside within a fluid, gas, or gel suitable for magnetic resonance probing, or the MRS particles may be packaged in a separate container along with some amount of fluid, gas, or gel, and the entire container and MRS particles contained within may be affixed to the object as a marker. The MRS-tagged object need not itself be within the fluid or gel in order to be marked.

One or more MRS may be bound to or incorporated within certain biological cells to mark the cells for subsequent magnetic resonance visualization studies. In this example, the MRS might include a specific biochemical coating ensuring that the MRS specifically binds to a specific cell type. This would enable tracking of cells and in particular, the ability to differentiate between different cell types by exploiting the different frequency shifts of the attached MRS.

Figure 52:
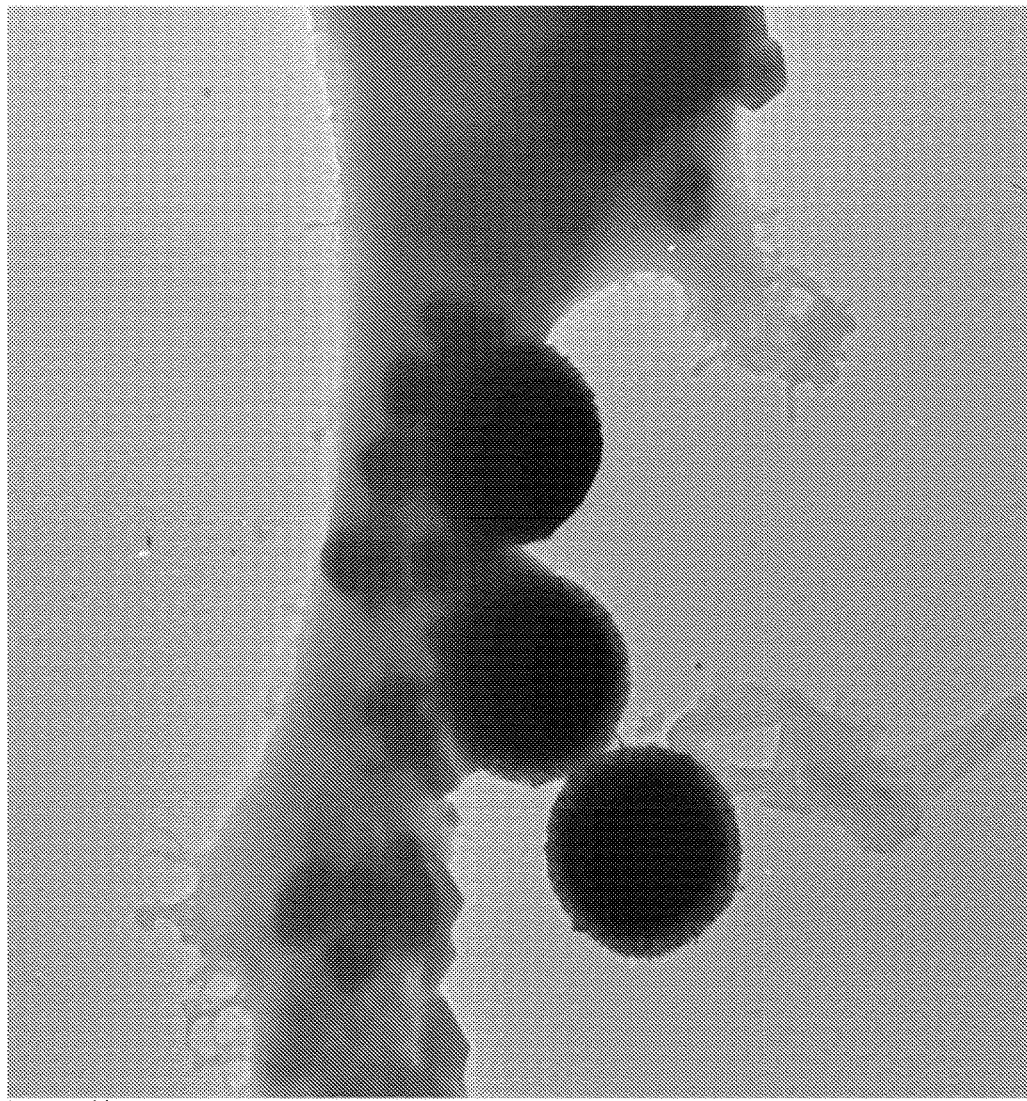
FIG. 52 is a TEM image of microfabricated single disk contrast agents attached to the cell membrane of a biological cell.
Figure 53:
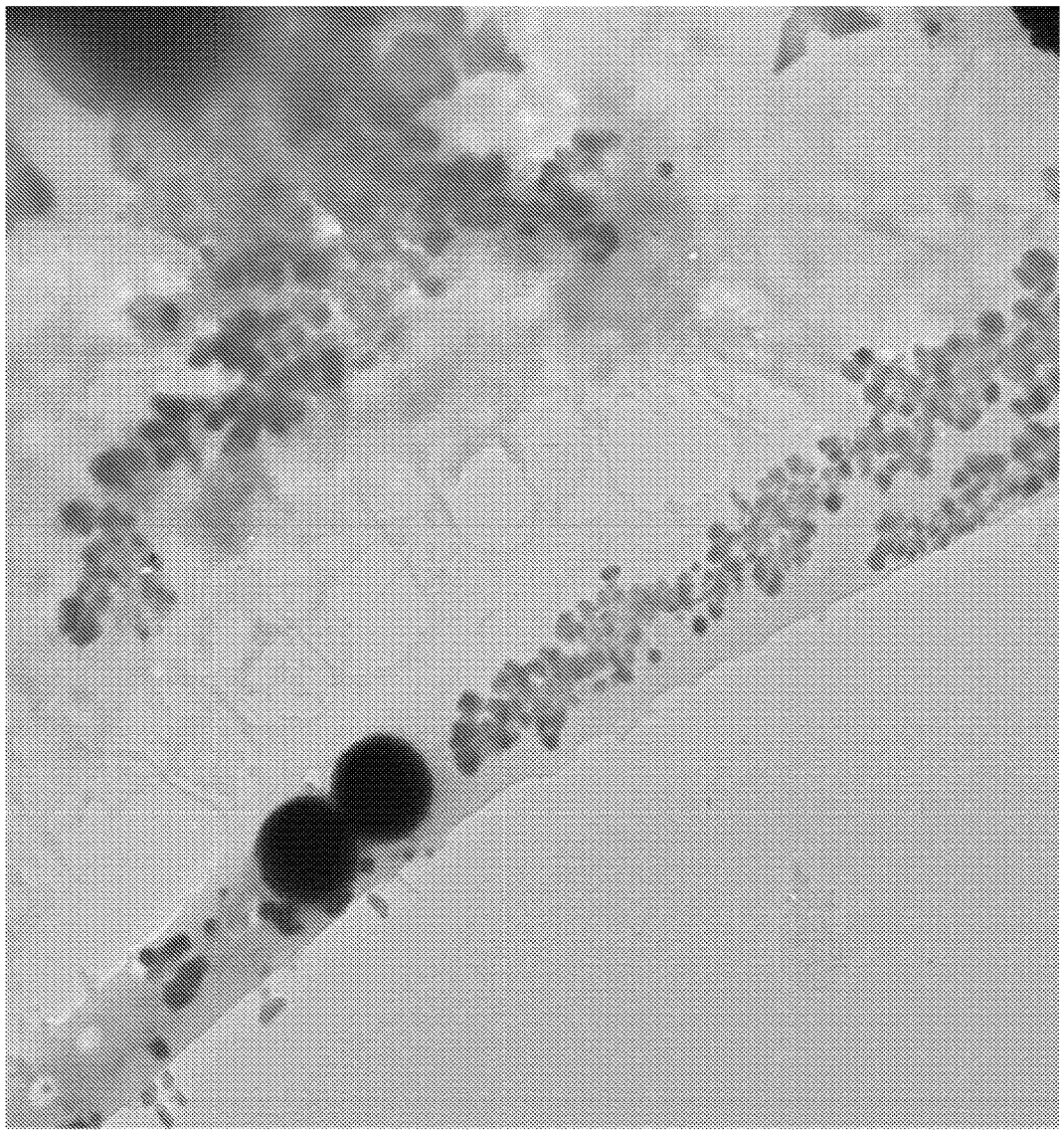
FIG. 53 is a TEM image of microfabricated single disk contrast agents incorporated within the cell membrane of a biological cell.

A biological cell labeled with several solid-disk MRS attached to the outer cell membrane is shown in FIG. 52. A biological cell labeled with several solid-disk MRS that have been incorporated into the cytoplasm of the cell is shown in FIG. 53.

The objects marked using MRS microtags may be in placed in stationary containers, or the objects may be situated within a vessel containing a moving flow of a fluid. For example, MRS microtags may be used to label objects flowing in a microfluidic steam, so that remote sensing and identification of the labeled objects may be made as they are transported within the microfluidic steam. Because this method makes use of magnetic resonance visualization techniques, an optical line of sight is not required to identify the objects, unlike existing microfluidics identification methods. As a result, this method may also be useful for monitoring microfluid flows in otherwise inaccessible locations within a microfluidics device.

In another example, living biological cells may be labeled using one or more MRS microtags functionalized with specific antigens or other binding agents in order to label particular flow types. In this example, flow cytometry may be conducted by inducing the cells to flow past a magnetic resonance sensor. Alternatively, living cells such as blood cells may be labeled as they circulate using one or more MRS microtags, and in vivo flow cytometry may be performed by sensing the labeled cells using a magnetic resonance scanner focused in a specific region of a blood vessel of a living subject. In yet another example, individual labeled cells may be tracked as they move within the circulatory vessels or other tissues or organs of a living subject.

The overall size of the MRS used to label living cells ranges from about 1 µm to about 10 µm, or may be about 1 µm, 2 µm, 3 µm, 4 µm, 5 µm, 6 µm, 7 µm, 8 µm, 9 µm, or 10 µm. The minimum overall size is limited to the smallest particle that is still visible using nuclear magnetic visualization, and the maximum overall size is limited to the largest particle that may be placed in the cytoplasm of a living cell without adversely affecting the viability of the labeled cell. In addition, in order to be detectable by a magnetic resonance device, the MRS microtag must have a magnetic moment of at least about $10^{-13}$ $Am^2$. The MRS microtags may be affixed to the outer cell membrane or cell wall, or the MRS microtags may be inserted into the cytoplasm of the labeled cell. The MRS microtags may be introduced into the cell by endocytosis means such as phagocytosis, macropinocytosis, caveolae, clathrin-mediated endocytosis or receptor-mediated endocytosis endocytosis. MRS microtags may also be introduced by genetic engineering methods such as electroporation or protoplasts.

Apart from identifying or tracking labeled objects moving in stream, this method may also be used to infer additional information about the fluid stream, such as flow speed by noting how the MRS microtags move within the stream.

g. Magnetic Field Sensors

An array of MRS particles in which each MRS particle has a slightly different frequency-shifting behavior may be placed within a magnetic field in order to measure its strength. Because the resonance frequency of the MRS determines an offset in the Larmor precession frequency of the nuclear magnetic moments that pass through the reserved space of the MRS, the exact absolute resonant Larmor precession frequency induced by the MRS may be used to provide a visual measure of the total magnetic field created by the superposition of the magnetic field within the reserved space and the external magnetic field. Because the magnitude of the magnetic field within the reserved space may be determined from the geometry and materials included in the MRS, the magnitude of the external applied magnetic field may be determined by subtracting the known magnetic field from the reserved space from the total magnetic field deduced from the frequency shift induced by the total magnetic field.

Alternatively, a uniform geometrical array of MRS particles may be arranged with the geometry of each MRS particle varied such that each frequency shift differs by a predetermined amount from the frequency shift of the neighboring MRS particles. Within the array, neighboring MRS may be spaced at least about 2-3 times the maximum outer dimension of the MRS away from all neighboring MRS to minimize the interaction of neighboring MRS external magnetic fields.

A magnetic resonance image of this array would show higher or lower signal amplitudes at a specific location in the array due to the frequency-shifting effects of the external magnetic field. Using this MRS particle array, the measurement of the magnetic field is effectively transformed from a field measurement method into a method of visually locating the spatial position of the higher or lower signal, and determining the field strength from the known frequency-shifting characteristics of the MRS particle at that location.

h. Distance/Pressure/Vibration/Torque Sensors (all Will Affect the Particles Measurable Frequency Shifts Through Change in Particle Geometry)

The MRS may be designed so that the frequency-shifting behavior may depend on a physical factor such as pressure, vibration, orientation changes, or torque experienced by the MRS. Magnetic resonance visualization of an MRS with this design may be used to non-invasively assess physical forces within a living subject or within another structure or fluid flow. Because the frequency-shifting of the MRS depends on, among other factors, the spacing between the magnetic portions and the orientation of the MRS relative to the background magnetic field, an MRS may be used to measure a variety of physical phenomena by transducing these phenomena into a distance change between the magnetic portions.

For example, an MRS may be designed to have a diminished ability to self-align to an applied magnetic field direction. Because the frequency-shifting behavior of the MRS also depends on its alignment with an applied magnetic field, changes in the frequency-shifting signal from an MRS with this design may be used to assess the degree of alignment with the external magnetic field. By altering the self-aligning behavior relative to the tendency to align with other applied forces such as fluid dynamic torques, the strength of the frequency-shifting signal may be used to measure the magnitude of the other applied forces.

Such orientation sensing may also be used to map fluid flow direction or for measuring fluid flow strength. For example, if the fluid dynamic forces were stronger than the magnetic self-alignment forces, then the orientation of the MRS, as measured by the strength or existence of the characteristic spectral signature of the MRS, may depend on the fluid flow direction relative to the direction of the applied magnetic field. Vasculature network geometries that may be too small to be visualized using existing magnetic resonance techniques may be mapped using the magnetic resonance visualization of an MRS with this design. In addition, fluid flow strength may be measured by observing whether or not the applied magnetic field is suitably strong to realign an MRS situated within a fluid flow.

Different portions of the magnetic material within an MRS may be designed to change orientation with respect to each other in reaction to an applied force or torque. The change in the relative orientation of the different portions of the magnetic materials alters the frequency-shifting of the MRS with this design. The changes in frequency-shifting behavior of the MRS, as measured using magnetic resonance visualization methods, may be used to provide an indirect measure of one or more torque forces acting on the MRS, or simply a different angular orientation of the MRS.

For example, if a double-disk MRS with one disk fixed to a rigid surface is placed into flow of sufficient velocity, the shear forces of the moving fluid acting on the unattached disk may exert a force that displaces the free disk relative to the immobilized disk, causing the NMR frequency-shift signal to cease. The system may be calibrated such the MRS stops producing a NMR frequency-shift signal at a known flow speed or shear force, or any array of MRS in which each MRS having a different NMR frequency-shift stops producing NMR frequency-shift signals at a different predetermined flow speed or shear force.

In another example, an MRS may be designed to measure fluid pressures in the blood stream. In this example, the alignment of the MRS with respect to the magnetic resonance magnetic field may be governed by an equilibrium between the magnetic self-alignment torques of the MRS from the magnetic resonance magnetic field and the rotational and/or shear forces exerted by the flowing fluid.

In yet another example, two or more MRS having different frequency-shifting characteristics may be attached to different locations along an object such as a protein molecule. The distance between the two different MRS may be estimated using the NMR multi-spectral imaging data. If the two MRS move to within 2-3 times the MRS size of each other, the NMR-shifting signals cancel each other out due to the mutual interference of the external magnetic fields of the two MRS. Thus, very small distances may be detected using the disabling of the MRS signal, in a manner analogous to fluorescence resonance energy transfer (FRET) measurement techniques.

In another example, a fluctuation in the frequency-shift magnitude may be used to sense vibrations using any of the MRS configurations described above.

i. Magnetic Separation

Being magnetic, these microstructures could be used in the same manner as regular magnetic beads in traditional magnetic separation protocols.

j. As Rotators of Objects Attached to Them/Magnetically Driven Rotary Pump-Like Motion/Fluid Pump/Mixer The MRS particles may be rotated indirectly using a rotating externally applied magnetic field and used to act as micropumps or micromixers in a variety of systems. A MRS particle may be designed with a high degree of magnetic shape anisotropy, resulting in a relatively high self-aligning magnetic torque between the MRS particle and an external applied magnetic field. By applying a rotating magnetic field to a MRS particle with a high magnetic anisotropy, a strongly rotating MRS particle results. This rotating behavior could be exploited to make fluid micropumps and micromixers.

Such rotation may also be useful for destroying selected biological cells such as cancerous cells by placing these microstructures within such cells and then rotating the external field to effectively churn up the cell's contents. The MRS may be introduced into the cell by endocytosis means such as phagocytosis, macropinocytosis, caveolae, clathrin-mediated endocytosis or receptor-mediated endocytosis endocytosis. The MRS may also be introduced by genetic engineering methods such as electroporation or protoplasts. If the MRS in this example were coated with binding agents that specifically bind only to cancerous cells, normal cells would effectively be unharmed using this method. The MRS in this example may be attached to the outer surface of the cell membrane or cell wall, the inner surface of the cell membrane, or may be inserted into the cytoplasm of the cell to be destroyed.

The strength of the rotating magnetic field used to rotate the MRS may range from about 1 Gauss to 1 Tesla, depending on the size and magnetic moment of the MRS used. The overall size of the MRS used to destroy selected cells using this method may ranges from about 1 µm to about 10 µm, or may be about 1 µm, 2 µm, 3 µm, 4 µm, 5 µm, 6 µm, 7 µm, 8 µm, 9 µm, or 10 µm Localized RF magnetic heating elements/targeted thermal ablation Depending on the exact material composition of the magnetic portions comprising these microstructures, application of an alternating magnetic field that repeatedly magnetizes and demagnetizes the objects could be used to generate local heating for targeted thermal ablation/destruction of biological cells such as cancerous cells.

Any non-spherical shape of MRS may be used to destroy selected cells using this method, including disks, rods, and cylinders. Any shape of MRS that includes a sharp edge may be particularly effective in destroying selected cells.

k. Localized Magnetic Field Gradients

The MRS particles may be used in alternative magnetic imaging techniques that take advantage of the relatively high localized magnetic field gradients external to each MRS. The external magnetic fields of the MRS particles produced using high Js materials such as iron may induce exceptionally high magnetic field gradients that may be useful for alternate magnetic imaging techniques, or for generating highly localized high magnetic forces.

EXAMPLES

Example 1

Assessment of Saturation of Dual-Disk Magnetic Resonance Structures

To assess the effect of the magnitude of applied magnetic field on the magnitude of the induced magnetic field in the reserved volume of a magnetic resonance structure, the following experiment was conducted. A 13 mm×13 mm grid of immobilized dual-disk magnetic resonance structures was tested using an alternating gradient magnetometer to assess the magnitude of the magnetic field induced within the reserved volumes as a function of the magnitude of the applied magnetic field, as well as the hysteresis of the induced magnetic field during a full alternating gradient cycle. Each dual-disk magnetic resonance structure in the 13 mm×13 mm grid was formed on a 15 mm×15 mm diced Pyrex substrate using microfabrication techniques. Each disk in a dual-disk magnetic resonance structure was a pure nickel disks having a disk radius of about 2.5 µm, a thickness of about 50 nm, and a disk separation distance of about 2 µm. The nickel material from which the disks were constructed had a saturation magnetic polarization ($J_s$) between about 0.5 and about 0.6 Tesla. Inter-particle spacings (center-to-center) were typically 3 to 4 times the particle diameter to minimize the influence from the induced far-field magnetic fields of neighboring particles on the induced magnetic field of each individual magnetic resonance structure in the grid.

A magnetic field was applied to the grid of magnetic resonance structures that alternated between a value of ±2000×10³/4π A/m, and the magnetic polarization of the dual-disk magnetic resonance structures was assessed.

Figure 7:
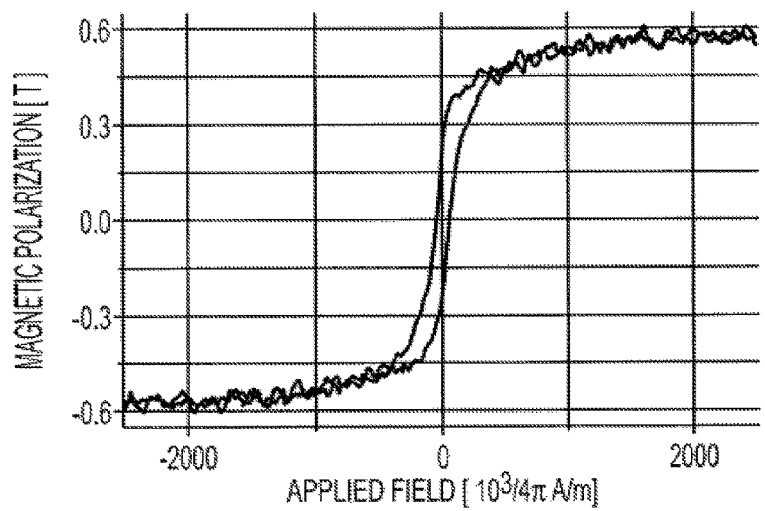
FIG. 7 is a graph of an alternating-gradient magnetometer hysteresis curve for an embodiment of a dual-disk magnetic resonance structure.

The results of the alternating gradient magnetometer measurements are summarized in FIG. 7. The dual-disk magnetic resonance structures achieved a saturated magnetic polarization at an applied magnetic field of about ±1000×10³/4π A/m, well below the magnitude of applied magnetic field generated by typical magnetic resonance scanning devices.

The results of this experiment confirmed that the dual-disk magnetic resonance structures achieved a saturated magnetic polarization at applied magnetic field magnitudes that are well within the capabilities of existing magnetic resonance scanning devices. As such, the field shift are independent of the MRI fields.

Example 2

Multi-Spectral Imaging Using Dual-Disk Magnetic Resonance Structures

To assess the effectiveness of multispectral imaging using magnetic resonance structures in a magnetic resonance scanning device, the following experiment was conducted. A grid of immobilized nickel dual-disk magnetic resonance structures were fabricated in a manner similar to those described in Example 1. The disks in each dual-disk magnetic resonance structure in this experiment had a diameter of about 1.25 mm and a separation of about 500 mm between the disks. Inter-particle spacings (center-to-center) were typically 3 to 4 times the particle diameter to minimize the influence from the induced far-field magnetic fields of neighboring particles on the chemical shifting of each individual magnetic resonance structure in the grid. Subgroups of the dual-disk magnetic resonance structures had disk thicknesses of 4, 6, and 8 µm respectively in order to vary the frequency shift induced by each respective subgroup. Each subgroup was arranged on the grid to form the letters R, G, or B, as illustrated in FIG. 11A. Accidental impurities in the nickel discs of these structures led to a reduction in the saturation magnetic polarization ($J_s$) of the disks to about 0.4 T. The disks in each dual-disk magnetic resonance structure in this experiment were submerged in water.

Free induction decay (fid) signals following a spin-echo were acquired sweeping through a range of frequencies covering the expected offsets produced by the particles. Shaped pulses with a Gaussian profile were used to limit bandwidth spread into the bulk water peak (as compared to a hard pulse). The bandwidths were sufficient to cover the frequency profiles produced by the particles. Acquisitions for the spectra were 8192 points in length, covering a bandwidth of −100 kHz. For the associated RGB image, three 2D chemical shift images were acquired, covering the frequency ranges of the particle spectra. Images are integrations of the spectra over the different frequency ranges. In-plane resolution was 500×750 µm.

AN image of the grid obtained using gradient-echo (GRE) MRI is shown in FIG. 11B. Magnetic dephasing due to the effects of the far-field magnetic fields induced by the particles enables the spatial imaging shown in FIG. 11B.

FIG. 11C-11E show the chemical shift imaging (CSI) of the grid magnetized by an applied magnetic field $B_0$. The additional spectral information provided by CSI imaging differentiates between individual particle types and improves particle localization. The particle spectra of each particle subgroup, as shown in FIGS. 11G-11J were shifted well away from the unshifted water proton line. Further, as shown in FIG. 11J, the particle spectra are each sufficiently separated, allowing for the unambiguous color-coding of the individual particle types with minimal background interference.

The results of this experiment demonstrated the feasibility of using the dual-disk magnetic resonance structures to achieve multispectral magnetic resonance imaging using a chemical shift imaging (CSI) process.

Example 3

Frequency-Shifting of Deuterium Proton Signals by Dual-Disk Magnetic Resonance Structures To determine the effectiveness of the frequency-shifting of protons other than water protons, the following experiment was conducted. A grid of dual-disk magnetic resonance structures similar to those described in Example 1 were submerged in deuterium oxide ($D_2O$) and imaged in a manner similar that described in Example 2. In this experiment, the disks in the dual-disk magnetic resonant structures had a diameter of about 25 µm, a disk thickness of about 0.5 µm, and a separation distance of about 10 µm between the disks. A grid of dual-disk magnetic resonance structures was constructed similar to those described in Example 1.

An individual pyrex chip was placed in a custom-made holder and filled with a layer of deuterium oxide ($D_2O$) to a thickness of about 150 µm, in order to submerge the particles and provide an additional layer of deuterium oxide ($D_2O$) well above the extent of any appreciable external magnetic fields induced by the magnetic resonance structures. The deuterium oxide ($D_2O$)-submerged pyrex chip sample was then placed next to or inside of the surface or solenoidal coils of the magnetic resonance scanning device for transmission/reception of the NMR signal.

Free induction decay (fid) signals following a spin-echo pattern were acquired in a manner similar to that described in Experiment 2. The bandwidth of the measurements was limited to about −75 kHz due to the limitations of the measurement coil.

The spectrum obtained from the measurements described above is shown in FIG. 12. The magnetic resonance structures induced a well-defined frequency shift of the deuterium protons of about −50 KHz. This frequency shift spectrum is in good agreement with estimated theoretical values.

The results of this experiment demonstrated the ability of the magnetic resonance structures to frequency-shift deuterium oxide protons as well as water protons.

Example 4

Effect of Pulse Delay on Frequency Shifting by Dual-Disk Magnetic Resonance Structures To assess the effect of the timing of preparatory off-resonance pulses on the frequency shifting of water protons and other NMR-susceptible nuclei by magnetic resonance structures during magnetic resonance scanning measurements, the following experiment was conducted.

A grid of dual-disk magnetic resonance structures similar to those described in Example 3 were submerged in water instead of deuterium oxide ($D_2O$) in a manner similar to that described in Example 3. In this experiment, the disks in the dual-disk magnetic resonant structures had a diameter of about 5 µm, a disk thickness of about 65 nm, and a separation distance of about 2 µm between the disks.

The submerged grid of particles was subjected to magnetic resonance measurements using an indirect detection technique. The magnetic resonance device delivered a series of off-resonance pulses (Gaussian shape, 100 µs in length) for a period of a few $T_1$'s, followed by an on-resonance 90-degree pulse, then the collection of fid data. Each point in a z-spectra was calculated by integrating the fid data for each different off-resonance frequency of the preparatory pulse train. The gap between each pulse in a preparatory pulse train was varied between 1 ms and 5 ms.

Figure 13:
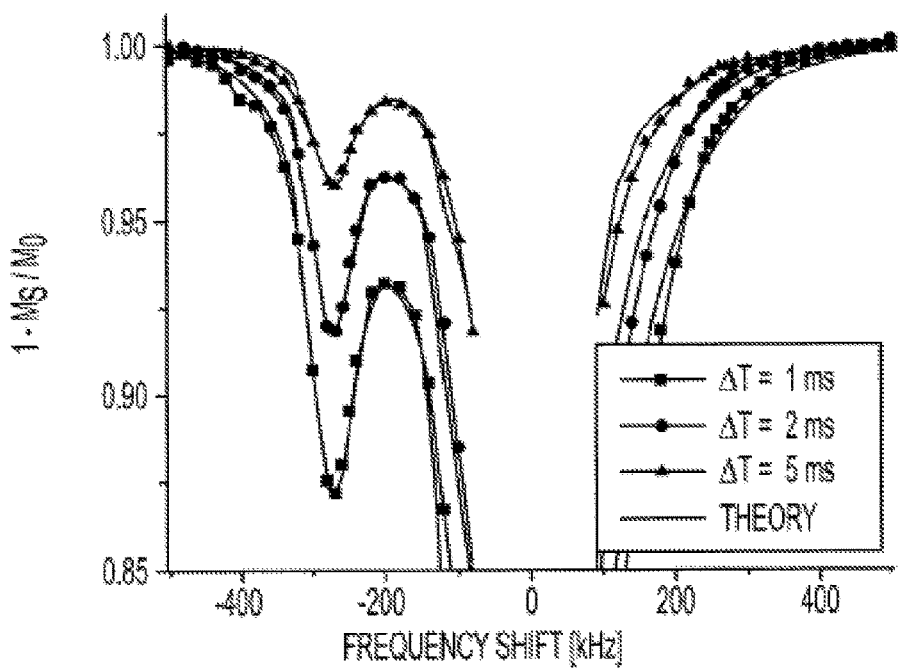
FIG. 13 is a graph showing the z-spectra produced by an embodiment of the dual disk magnetic resonance structure using difference delays ($\Delta T$), between off-resonant $\pi/2$ pulses.

The z-spectra obtained for pulse train gaps of 1 ms, 2 ms, and 5 ms are shown in FIG. 13. Closer spacing of the preparatory pulses resulted in a higher magnitude of signal at the shifted frequency, with negligible effect on the amount of frequency shift.

The results of this experiment determined that that the frequency shift induced by the magnetic resonance structures is insensitive to the spacing of the off-resonance preparatory pulses. However, the amount of frequency-shifted water protons and other NMR-susceptible nuclei, as indicated by the magnitude of the fid signal at the shifted frequency, increases when the preparatory pulses are spaced closer together.

Example 5

Example 5: Effect of Applied Magnetic Field Strength on Frequency Shifting by Dual-Disk Magnetic Resonance Structures To determine the effect of the applied magnetic field strength on the frequency shifting of water protons and other NMR-susceptible nuclei by magnetic resonance structures during magnetic resonance scanning measurements, the following experiment was conducted. The grid of dual-disk magnetic resonance structures submerged in water described in Example 4 was measured using a similar indirect detection technique. In this experiment, an identical preparatory pulse sequence was used for each set of measurement. However, the sets of measurements obtained in this experiment were conducted using magnetic field strengths $B_0$ of 4.7 T, 7.0 T, and 11.7 T. Differing magnetic field profiles from the different coils used may have introduced limited variability in the results.

Figure 14:
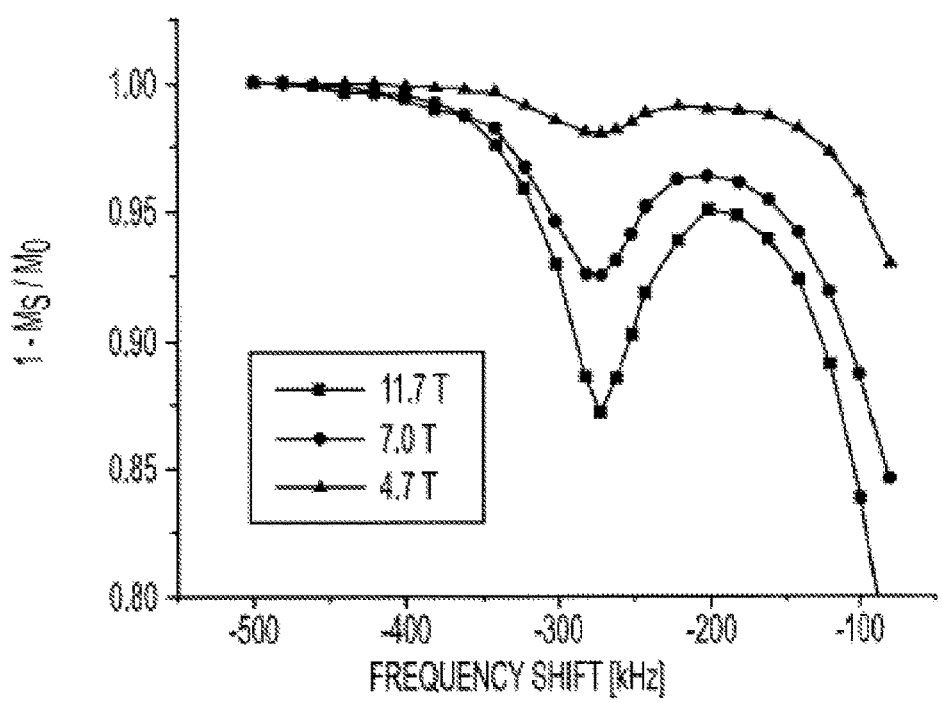
FIG. 14 is a graph showing the z-spectra produced by an embodiment of the dual-disk magnetic resonance structure measured at three different field-strengths.

The z-spectra for the fid signals induced by the magnetic resonance structures are shown in FIG. 14. Variation in the applied magnetic field strength did not significantly alter the frequency shift induced by the magnetic resonance structures. At the shift frequency, the fid signal was higher in magnitude at the higher applied magnetic field strengths.

Example 6

Effect of Disk Radius on Frequency Shifting by Dual-Disk Magnetic Resonance Structures To assess the sensitivity of the frequency shift induced by a dual-disk magnetic resonance structure to variation in the radii of the disks, the following experiment was conducted. Two grids of dual-disk magnetic resonance structures submerged in water similar to the grid described in Example 4 were measured using a similar indirect detection technique. In one grid, the disk diameter was about 5 µm, the thickness of each disk was about 50 nm, and the disk separation distance was about 2 µm. In the other grid, the disk diameter was about 3 µm, the thickness of each disk was about 50 nm, and the disk separation distance was about 1 µm.

Figure 15:
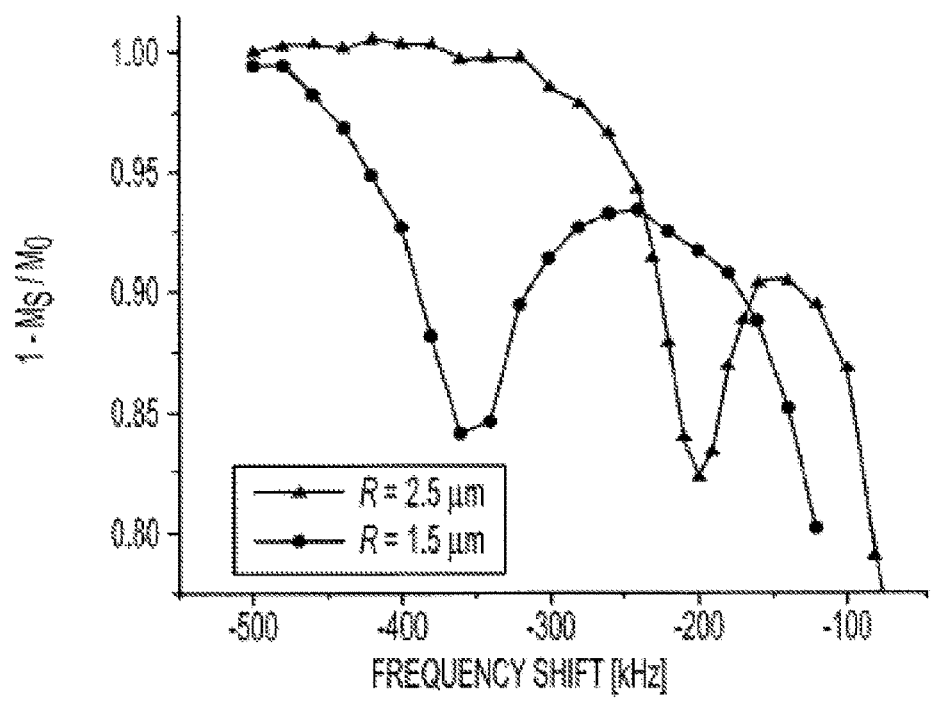
FIG. 15 is a graph showing the z-spectra produced by two embodiments of the dual-disk magnetic resonance structure having difference disk radii.

The z-spectra obtained from the two grids of magnetic resonance structures is shown in FIG. 15. The grid containing the smaller-radius dual disk magnetic resonance structures had a higher frequency shift compared to the larger-radius grid. The frequency shifts of the two magnetic resonance particles measured in this experiment were sufficiently separated in frequency shift (about −370 kHz vs. about −200 kHz), and possessed sufficiently narrow line width to ensure the detection of individual signals in a multiplexed magnetic resonance measurement technique.

The results of this experiment demonstrated that variation in the radii of the disks in a dual-disk magnetic resonance structure resulted in detectably distinct frequency-shifting by the magnetic resonance structures in a multiplexed magnetic resonance measurement environment.

Example 7

Effect of Disk Thickness on Frequency Shifting by Dual-Disk Magnetic Resonance Structures To assess the sensitivity of the frequency shift induced by a dual-disk magnetic resonance structure to variation in the thickness of the disks, the following experiment was conducted. Grids of dual-disk magnetic resonance structures submerged in water similar to the grid described in Example 4 were measured using a similar indirect detection technique. Each grid contained an array of dual disk magnetic resonance structures with the same specified disk thickness; the specified disk thickness of the different grids varied between about 50 nm to about 75 nm.

Figure 16:
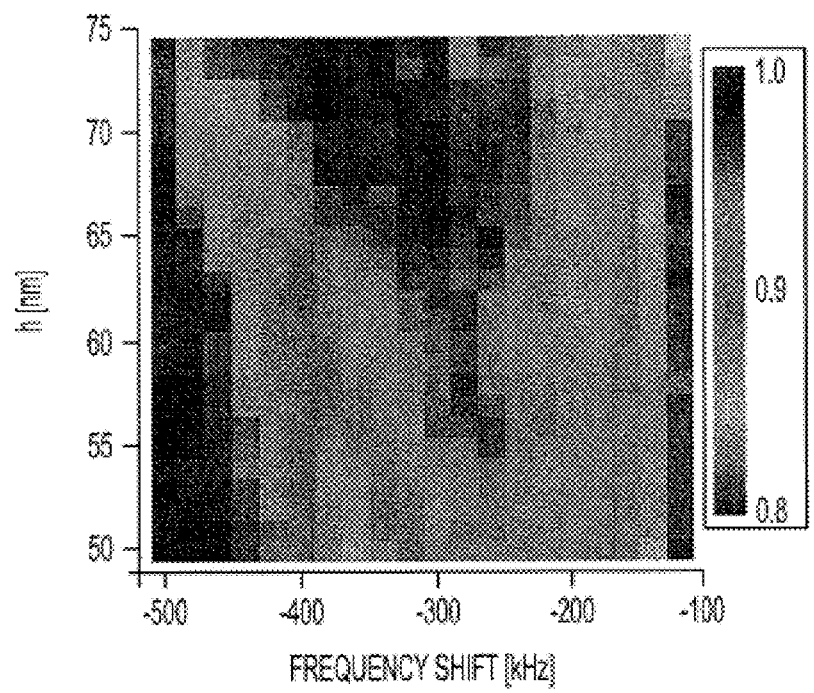
FIG. 16 is a graph showing a map of the z-spectra of numerous embodiments of the dual-disk magnetic resonance structures having different disk thicknesses (h).

FIG. 16 is a summary of the z-spectrum values measured for each of the grids having disks with varying thicknesses. Each row in FIG. 16 shows the experimental $H_2O$ z-spectrum for a different particle disc thickness. In this figure, the raw z-spectra of the shifted peaks atop the unshifted broadened water background is shown. This background may be eliminated by calculating the differences between corresponding positive- and negative-frequency saturation signals to eliminate the effects of the water background signal.

As shown in FIG. 16, the dual-disk magnetic resonance structures induced a frequency shift of about −360 kHz at a disk thickness of 50 nm, which increased gradually to a frequency shift of about −500 kHz at a disk thickness of 75 nm. In addition, as the thickness of the disks decreased, the line width of the frequency shift became increasingly broad.

The results of this experiment demonstrated that the magnitude of the frequency shift induced by a dual-disk magnetic resonance structure may be predictably and controllably manipulated by varying the thickness of the disks.

Example 8

Effect of Asymmetries of Dual-Disk Magnetic Resonance Structures on Induced Frequency Shifting To assess the effects of asymmetries within a dual-disk magnetic resonance structure on the frequency shift induced by the structure, the following simulations were conducted. Numerical calculations were performed to estimate the effect of various asymmetrical variations in the geometry of a dual-disk magnetic resonance structure on the structure's frequency shift characteristics. All calculations were performed for a dual disk structure having a saturated magnetic density of 0.6 T (corresponding to nickel), a disk diameter of 2 μm, a disk thickness of 40 nm, and a disk separation distance of 0.85 μm.

Figure 32:
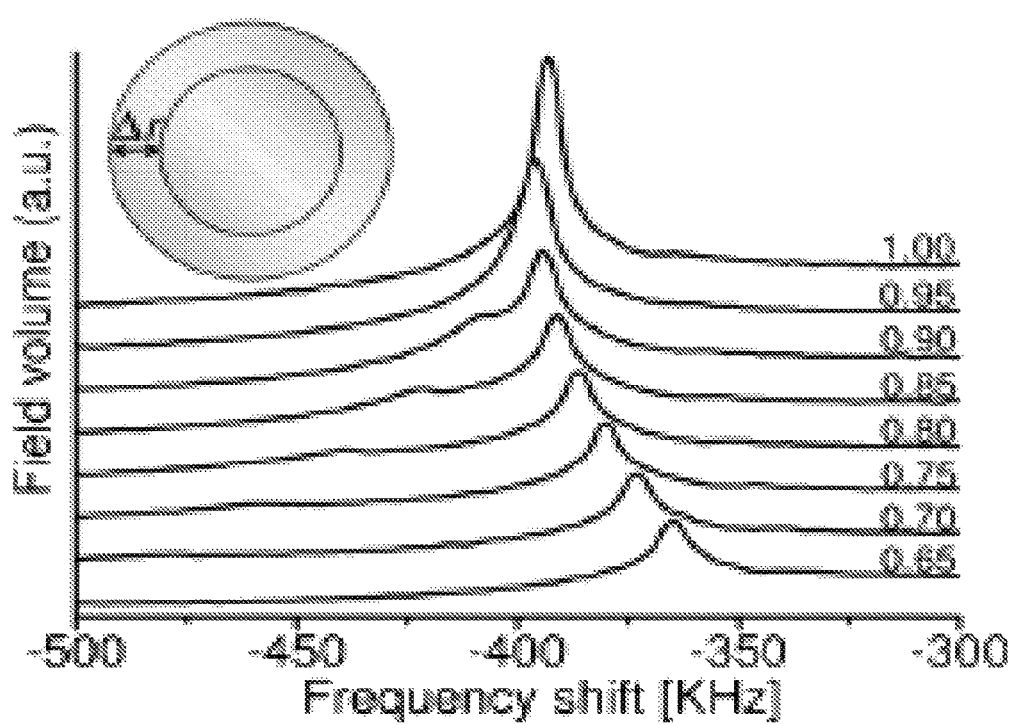
FIG. 32 is a graph showing the z-spectra of an embodiment of a dual-disk magnetic resonance structure in which one disk is smaller in radius.

One set of calculations varied the radius of one disk of the pair from 100% to 65% of the value of the other disk. The results of these calculations are summarized in FIG. 32. As the disks become increasingly different in size, there is a significant signal loss, peak broadening, and alteration of the induced frequency shift.

Figure 33:
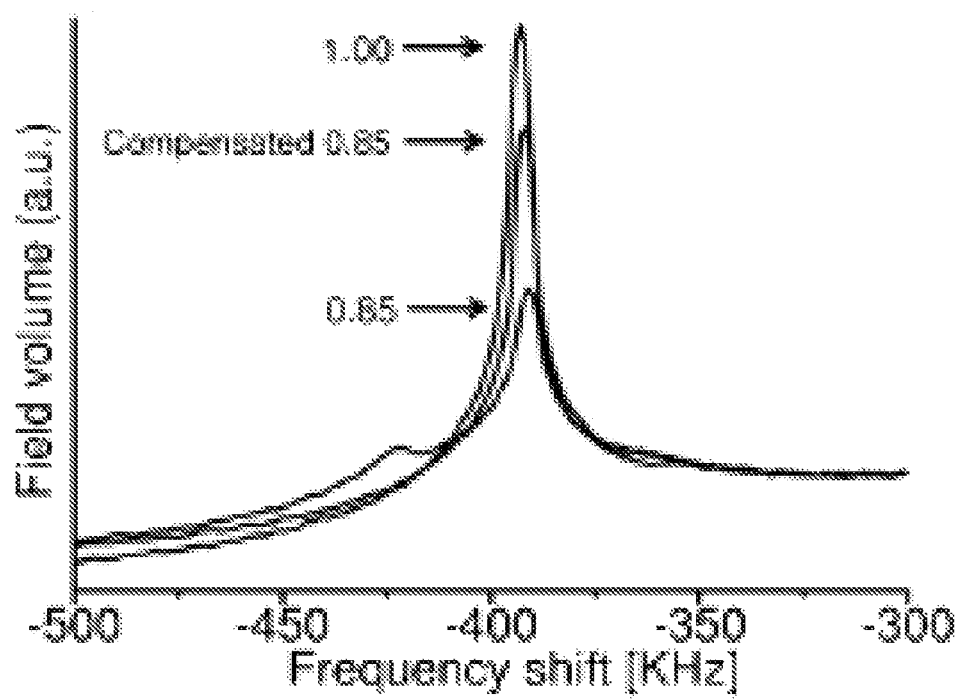
FIG. 33 is a graph showing the z-spectra of an embodiment of a dual-disk magnetic resonance structure in which one disk is smaller in radius and thicker than the other disk.

In another set of calculations, the thickness of the mismatched disks in a dual-disk structure was varied to determine whether the mismatch in size could be compensated for by variation in disk thickness. FIG. 33 summarizes the results of these calculations, showing the z-spectrum from FIG. 32 for the dual-disk magnetic structure with identical disks (1.00), with one disk having a radius that was 85% of another (0.85), and with one disk that was 85% of the other, but the smaller disk is also thinner than the larger disk to compensate for the radius asymmetry. As shown in FIG. 33, variation in disk thickness may be used to partially compensate for difference in disk radius.

Figure 34:
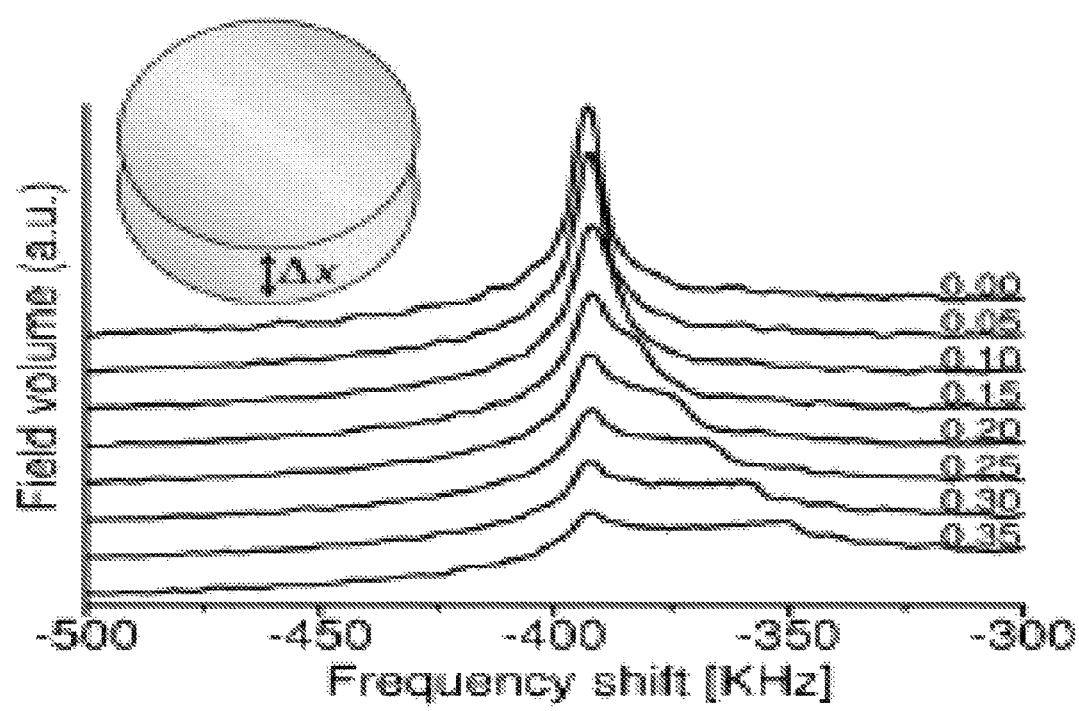
FIG. 34 is a graph showing the z-spectra of an embodiment of a dual-disk magnetic resonance structure in which one disk is offset relative to the other disk in a direction perpendicular to the applied magnetic field.
Figure 35:
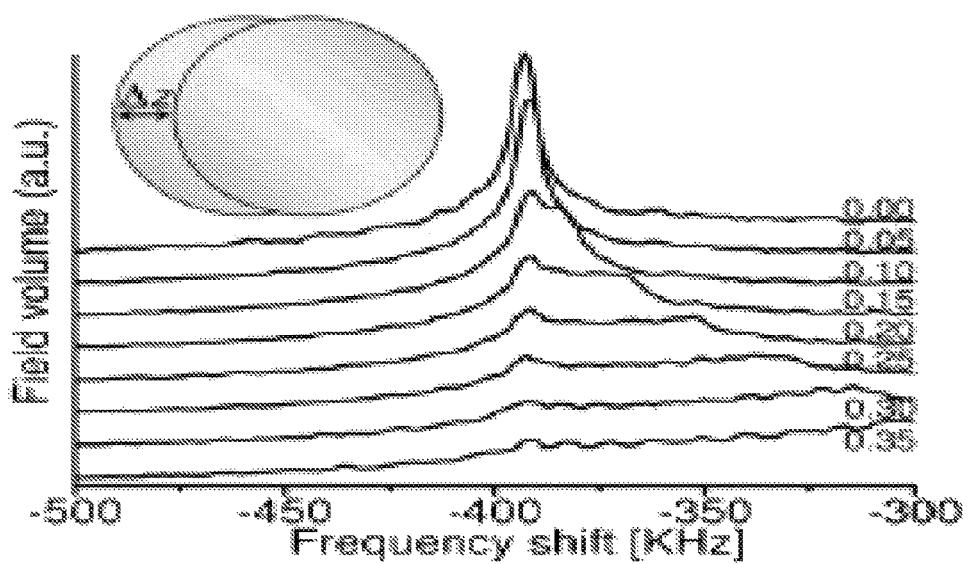
FIG. 35 is a graph showing the z-spectra of an embodiment of a dual-disk magnetic resonance structure in which one disk is offset relative to the other disk in a direction parallel to the applied magnetic field.

Another set of calculations varied the offset of the centerlines of two identically-sized disks in a dual disk magnetic resonance structure by as much as 35% of the disk radius. FIG. 34 is a set of z-spectra for various centerline offsets in a direction perpendicular to the orientation of the applied magnetic field. FIG. 35 is a set of z-spectra for various centerline offsets in a direction parallel to the orientation of the applied magnetic field. In both FIG. 34 and FIG. 35, as the centerlines of the disks are increasingly offset, there is a significant signal loss and peak broadening.

Figure 36:
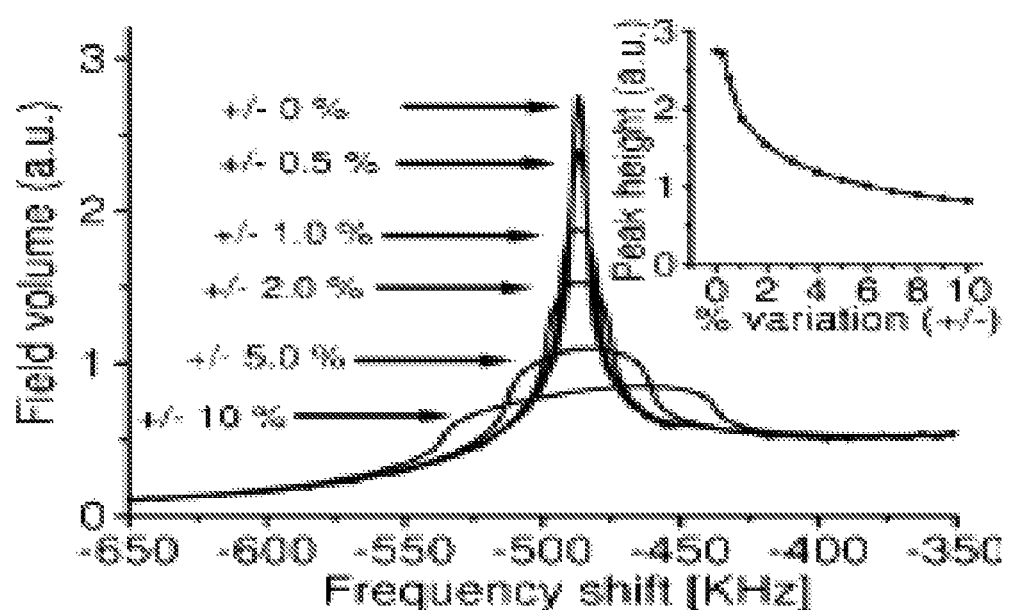
FIG. 36 is a graph showing the effect of manufacturing variation on the z-spectra of an embodiment of a dual-disk magnetic resonance structure.
Figure 37A:
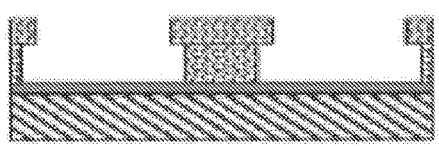
FIGS. 37A-37E are drawings illustrating the intermediate steps of an embodiment of a fabrication process for a dual-disk magnetic resonance structure.
Figure 37B:
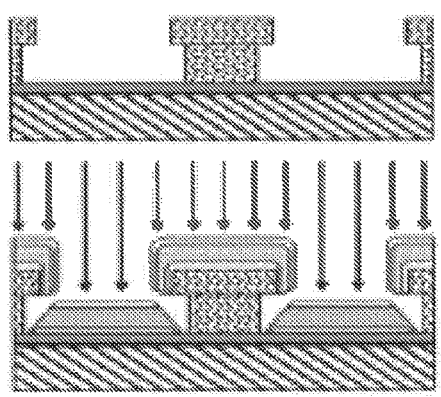
Figure 37C:
Figure 37D:
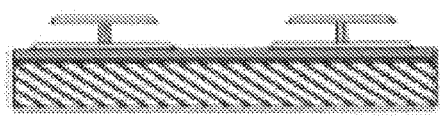
Figure 37E:
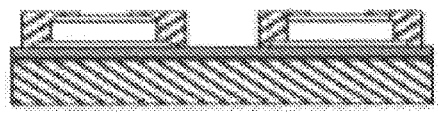

Yet another set of calculations, the effects of cross-wafer processing variations on the frequency-shift characteristics of the dual-disk magnetic resonance structures were assessed. In this set of calculations, the effects of up to 10% interparticle variation due to random variation in the manufacturing process was estimated. FIG. 36 is a set of z-spectra calculated assuming arrays of structures with varying degrees of random variation in the manufacturing process. As the variation of the manufacturing process increases past about 1%, there was significant signal loss.

The results of this experiment demonstrated that both systematic asymmetries, and random manufacturing errors of sufficient magnitude may significantly impact the efficacy of the dual-disk magnetic resonance structure through signal loss, which impacts the detectability of the structures, and peak broadening, which impacts the ability to discriminate between structures with different geometries used in multiplexed magnetic resonance visualization techniques. This demonstrate the requirement of accurate microfabrication of these structures and precludes less accurate chemical synthesis approaches.

Example 9

Deactivation of Dual-Disk Magnetic Resonance Structures by Obstruction of Reserved Volume To demonstrate the effect of filling in the reserved space between the disks of a dual-disk magnetic resonance structure, the following experiment was conducted. A grid of dual-disk magnetic resonance structures submerged in water similar to the grid described in Example 4 were measured using a similar indirect detection technique. In this experiment, the spaces between the disks of a portion of the structures were filled in, as shown in SEM image in the left-hand inset of FIG. 17. The right-hand inset figure of FIG. 17 is a picture of an image obtained by an magnetic resonance device using an indirect detection technique. The group of structures with filled-in reserved volumes ("OFF" group) did not generate a signal, and the group of structures which had open reserved volumes ("ON" group) to allow the diffusion of fluid in and out of the reserved volume generated distinct magnetic resonance signals.

The results of the experiment demonstrated that the dual-disk magnetic resonance structures may be deactivated by filling in the reserved volume, and that the signal generated by the structures was dependent on the diffusion of fluid into the reserved volume between the disks of a dual-disk magnetic resonance structure.

Example 10

Effect of Non-Uniform Cylinder Wall Thickness on Frequency Shifts of Hollow Cylinder MRS To assess the effect of variations in the thickness of the walls of a single hollow cylinder magnetic resonance structure, the following simulatin was conducted. Rather than dual-disk structures, the magnetic resonance structures were hollow cylinders having increasingly non-uniformity in the cylinder wall thickness. FIG. 19B is a series of simulated z-spectra summarizing the results, showing diminished signal strength and peak broadening for the hollow cylinders with non-uniform wall thicjkness.

The results of this experiment demonstrated that the signal strength and line width of a hollow cylinder magnetic resonance structure is relatively sensitive to variations from a uniform wall thickness over the full length of hollow cylinder.

Example 11

Effect of Cylinder Geometry Variation on Frequency Shifts of Hollow Cylinder MRS To assess the effects of variations in the geometry of a hollow cylinder magnetic resonance structure on the frequency shift characteristics of the structure, the following simulations were conducted. Grids similar to those described in Example 10, but for the use of hollow cylinder magnetic resonance structures rather than dual-disk structures, were measured using an indirect detection technique. Z-spectra were obtained using an 11.7 T MRI scanner for four different arrays of hollow cylinder geometries. All hollow cylinders were constructed of nickel, an had an aspect ratio (length/diameter) of about 1.2.

FIGS. 23A-23D show experimental z-spectra acquired from the four different arrays of hollow cylinder magnetic resonance structures. The hollow cylinders measured in FIG. 23A had an outer diameter of about 2 µm and a wall thickness of about 75 nm. The hollow cylinders measured in FIG. 23B had an outer diameter of about 2 µm and a wall thickness of about 150 nm. The hollow cylinders measured in FIG. 23C had an outer diameter of about 850 nm and a wall thickness of about 40 nm. The hollow cylinders measured in FIG. 23D had an outer diameter of about 900 nm and a wall thickness of about 50 nm.

Comparing the z-spectra of FIGS. 23A-23D, increasing the wall thickness increased the magnitude of the frequency shift when comparing hollow cylinders of approximately the same outer diameter. However, the magnitude of the frequency shift was dependent on a combination of all of the factors included in Equation 8 above. For example, the magnitude of the frequency shifts for the smaller diameter cylinders, as shown in FIGS. 23C and 23D fall in between the frequency shift magnitudes of the larger hollow cylinders, shown in FIGS. 23A and 23B. In all cases, the frequency shifts of the hollow cylinders fell within about 10% of the frequency shifts predicted by Equation 8 above.

The results of this experiment demonstrated the magnitudes of frequency shifts induced by hollow cylinder magnetic resonance structures for a variety of geometries were in agreement with theoretical values predicted by Equation 8 above. By varying the geometries of the hollow cylinders, a multitude of distinct signals may be generated for use in a multiplexed magnetic resonance visualization technique.

Example 12

Flow Tagging Using Hollow Cylindrical MRS

To demonstrate the feasibility of flow tagging using a hollow cylindrical magnetic resonance structure, the following experiment was conducted. Flow tagging is defined in this context as the process of frequency-shifting a plurality of water protons and other NMR-susceptible nuclei in a moving stream, rendering the frequency-shifted water protons and other NMR-susceptible nuclei in the flow detectable using a magnetic resonance scanner as the flow travels through a flow path. In this example, a large hollow cylinder magnetic resonance structure was formed by wrapping a layer of nickel around the entire circumference of a region of a tube. Two tubes were tested in which one tube was wrapped to a thickness of 50 µm and the and the other tube to a thickness of about 100 µm.

Figure 27:
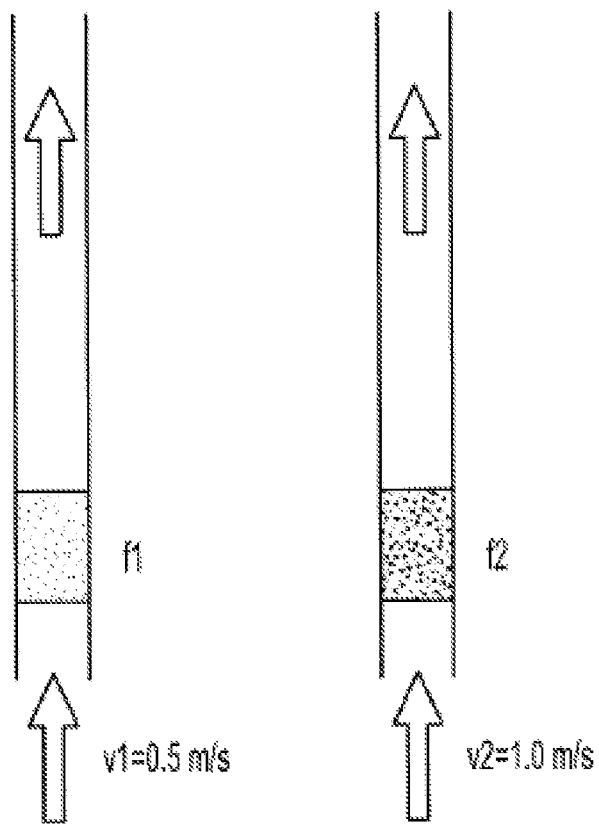
FIG. 27 is a drawing showing a flow tagging application of an embodiment of a hollow cylindrical magnetic resonance structure at two different flow speeds.

Water was passed through each of the two tubes at a flow velocity of about 0.5 m/s and about 1 m/s respectively, as shown in FIG. 27. As the water passed through the nickel hollow cylinders wrapped around each tube, the water protons in each pipe were periodically spin-labeled by a uniform magnetic field inside each hollow cylinder, together with exposure to a RF magnetic pulse at the offset Larmor frequency, defined by the above-mentioned uniform magnetic field. The spin-labeled water protons produced a lower fid signal within the flow of water through the magnetic resonance imaging region downstream of each hollow cylinder magnetic resonance structure. In this experiment, the RF magnetic pulses were applied to both tubes simultaneously.

FIG. 28 is an MRI image formed after water passing through the hollow cylinder was spin-labeled using three temporally separated RF pulses to the hollow cylinder of the left tube, which contained water flowing at about 0.5 m/s. The image of the left tube in FIG. 28 exhibited a characteristic parabolic laminar flow profile from the three groups of spin-labeled flow. A similar result was obtained for the tube with a flow velocity of about 1.0 m/s as shown in FIG. 29. In FIG. 29, the three layers of spin-tagged flow are more spatially dispersed along the direction of the flow due to the higher flow velocity. The distinct frequency shifts induced by the two hollow cylinder thicknesses used in this experiment was demonstrated by the observation that the spin-labeling of the flow in one tube did not affect the spin-labeling in the other tube. As a result, each tube may be spin-tagged separately.

To demonstrate the capability of the spin-labeling technique described above to perform perfusion imaging, the flow tubes described above were spin-labeled using RF labeling pulses spaced closely enough in time so as to appear continuous in subsequent MRI images. FIGS. 30 and 31 are MRI images taken from the left and right tubes, respectively. In FIG. 30, the flow labeled by a rapid series of RF pulses appears as a solid continuous band having the same laminar parabolic flow profile as in FIG. 28. In the more rapid flow shown in FIG. 31, a similar parabolic continuous band was detected in the MRI image.

The results of this experiment demonstrated that the flow through tubes may be tagged in a local region by spin-labeling the flow using a hollow cylinder magnetic resonance structure situated around the circumference of the tube and excitatory RF pulses. The RF pulses may be discretely spaced in order to obtain information about finer features of the flow structure such as parabolic flow profile, or the RF pulses may be closely spaced to produce an essentially continuous region of tagged flow for other flow visualizations such as perfusion imaging.

Example 13

Theoretical Single-Voxel Signal Due to Transverse Dephasing for Design of Solid Particulate MRS To assess the effects of various factors such as the materials used to construct a solid particulate MRS, and the position of a solid particulate MRS within a voxel volume on the contrast signal produced during magnetic resonance visualization, the following experiment was conducted. A theoretical simulation of the magnetic resonance contrast was performed using solutions to the equations described below.

The signal intensities of the solid particulate MRS were modeled theoretically assuming that the contrast signals originated from individual, micrometer-sized contrast particles with high magnetic moments and that the signals were measured using high-resolution imaging. The calculations were simplified by assuming that the MRS fell within a static dephasing regime in which $\Delta\omega \cdot \tau_c \gg 1$, where $\Delta\omega$ was the local precession frequency due to the magnetic field of the MRS, and $\tau_c$ was the time to diffuse a distance equal to the size of the MRS. Ignoring k-space shifting effects, the time-dependent modification to the magnetic resonance signal S caused by the solid particulate MRS was proportional to an integral taken over all precessing spins within the volume of interest as expressed in Eqn. (10):

$$S(t) \propto \int \rho(\vec{r}) \cdot e^{-i\phi(\vec{r},t)} d\vec{r} \qquad (10)$$

where t was the time following excitation by an initial $\pi/2$ electromagnetic pulse, $\vec{r}$ was the spin location relative to the MRS, $\rho$ was the spin density, and $\varphi$ was the additional accrued transverse phase due to the particle field in the rotating frame.

Since the MRS size was always far less than the voxel size in this experiment, the signal produced by the MRS was dominated by spins from the far-field region of the MRS. As a result, the magnetic field induced by the MRS was modeled as a magnetic dipole independently of the shape of the MRS. The MRS was assumed to be a sphere of radius determined by its net dipole moment $p_m$ and the magnetic saturation of its constituent material. For a $B_0$-field aligned in the z-direction, the z-component of the field produced by the MRS when magnetized by $B_0$ was $B_z = p_m \cdot (\mu_0/4\pi)(3\cos^2\theta - 1)/|\vec{r}|^3$ for a magnetic permeability $\mu_0 = 4\pi \cdot 10^{-7}$ H/m and a polar angle $\theta$. For a ferromagnetic or superparamagnetic particle having a radius a and saturation magnetic polarization $J_s$, the dipole moment is $p_m = (J_s/\mu_0) \cdot 4\pi a^3/3$, resulting in an equatorial precession frequency of $\Delta\omega = \gamma J_s/3$ for the gyromagnetic ratio $\gamma$.

Neither $B_0$ nor the magnetic susceptibility difference $\Delta\chi$ affects the equatorial precession frequency, since ferromagnetic and superparamagnetic substances are magnetized to saturation by typical $B_0$ fields. The normalized signal decay from such a particle centered in a spherical voxel of radius R and of homogeneous spin density may then be expressed:

$$\frac{S(t)}{S(0)} = \frac{3}{2(R^3 - a^3)} \int_0^\pi \int_a^R \exp\left[-i\Delta\omega \cdot t \cdot \frac{a^3}{r^3}(3\cos^2\theta - 1)\right] \cdot r^2 \sin\theta \, dr \, d\theta \qquad (11)$$

Although the high magnetic moments typical of the MRS to be modeled precluded immediate expansion of the integrand in Eqn. (11), simplification was still possible if the ratio of voxel to particle radius $((\Delta\omega)(t)(a/R)^3)$ was on the order of unity or less. For millisecond timescales and micrometer-sized ferromagnetic particles, this condition was fulfilled at magnetic resonance resolutions of about one hundred micrometers or larger. By integrating first, and then simplifying the resultant functions of $\Delta\omega(t)$ and $\Delta\omega(t)(a/R)^3$ through asymptotic and power series expansions, respectively, the signal magnitude was approximated to second order in $\Delta\omega(t)(a/R)^3$:

$$\frac{S(t)}{S(0)} \approx 1 - c_1\left(\Delta\omega \cdot t \cdot \frac{a^3}{r^3}\right) + c_1\left(\Delta\omega \cdot t \cdot \frac{a^3}{r^3}\right)^2 + \text{higher order terms} \qquad (12)$$

in which: $c_1 \frac{2\pi}{3\sqrt{3}}$ and $c_2 = \frac{2}{5} + \frac{2}{9}\left[1 - \frac{\ln(2+\sqrt{3})}{\sqrt{3}}\right]^2$ The quadratic term in Eqn. (12) represented the onset of signal saturation due to finite voxel size. Despite the limited expansion of terms, Eqn. (12) accurately approximated the solution for the integral in Eqn. (11) for initial signal decay and saturation. Comparing the linear and quadratic terms in Eqn. (12) estimated the dephasing period ($t_{sat}$) required to appreciably saturate out the voxel signal. Although the asymptotic nature of signal saturation made the definition of the dephasing period somewhat arbitrary, as a first measure the point at which S(t) became stationary, as approximated by Eqn (12) was used to estimate the dephasing period:

$$t_{sat} = \frac{1}{\Delta\omega} \cdot \frac{c_1}{2c_2}\left(\frac{R}{a}\right)^3 \approx \frac{4}{J_s}\left(\frac{R}{a}\right)^3 \qquad (13)$$

Although the equations developed above assumed spherical voxels, the equations were adapted to cubic voxels shapesby replacing the spherical voxel radius R with an effective cubic "radius" $R_c$ according to the relation $(4/3)\pi R_c^3 = 8R^3$, where R is the half-width of a cubic voxel.

Theoretical voxel intensities induced by a 1-μm diameter spherical MRS particle with a $J_s = 1$ T was estimated using the equations and methods described above.

Figure 43:
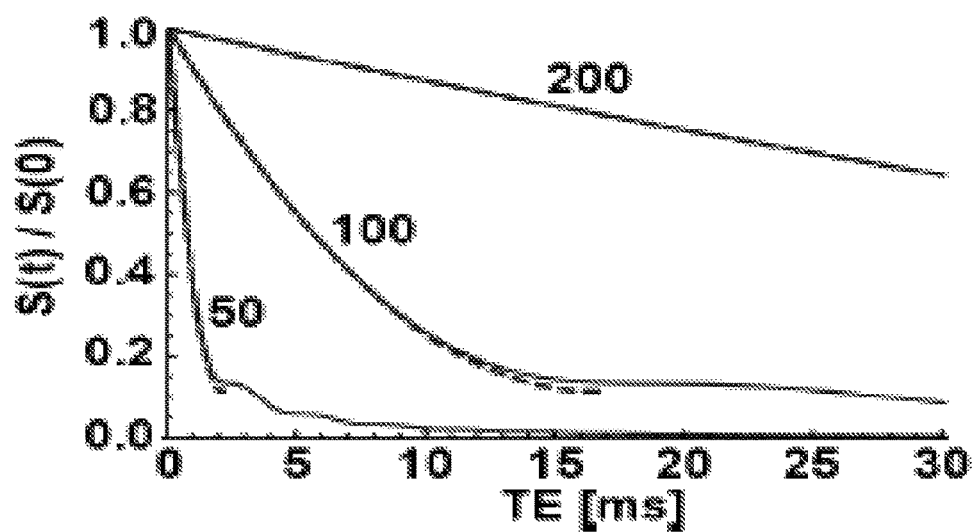
FIG. 43 is a graph showing the effect of transverse dephasing on theoretical single voxel signal intensities during magnetic resonance imaging of a solid high magnetic moment $T_2^*$ contrast agent using spherical voxel geometry.
Figure 44:
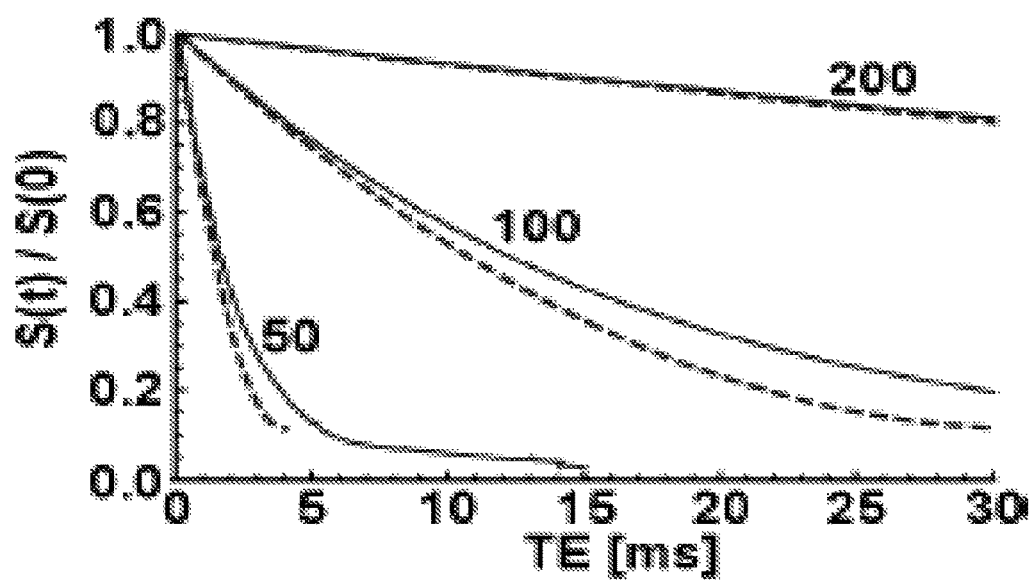
FIG. 44 is a graph showing the effect of transverse dephasing on theoretical single voxel signal intensities during magnetic resonance imaging of a solid high magnetic moment $T_2^*$ contrast agent using cubic voxel geometry.

FIG. 43 is a graph summarizing theoretical single-voxel signal intensities relative to background signal intensity due to transverse dephasing effects of a solid particulate MRS centered within a spherical voxel having a diameter of 50-μm, 100-μm, or 200-μm. FIG. 44 is a similar graph summarizing theoretical single-voxel signal intensities within cubic voxels. For both FIGS. 43 and 44, as the echo time TE increased, the contrast increased until a saturated contrast level was reached. This saturation contrast was highest for the smallest voxel size in both spherical and cubic voxels.

The results of this experiment demonstrated that the solid particulate MRS produced suitable signal contrast for gradient-echo MRI visualization, particularly at the smaller voxel size of 50-100 μm.

Example 14

Theoretical Single-Voxel Signals with and without Image Distortion Correction

To assess the effects of image distortion on the contrast signal produced during magnetic resonance visualization, the following simulation was conducted. Although the image darkening produced by a contrast particle is typically dominated by $T_2^*$ transverse dephasing, for magnetic resonance conditions such as high-resolution imaging and short echo times, geometric image distortion may also appreciably modify the contrast signal intensity. The image distortions result from the superposition of the contrast particle's field onto the read magnetic field gradient, resulting in local hypointense and hyperintense contrast signal regions near the contrast particle. If the hypointense and hyperintense contrast signal regions fall within the same voxel, conservation of spin number ensures that the spatial variations in apparent spin density cancel out within the voxel, resulting in negligible image distortion effects. However, if hypointense and hyperintense contrast signal regions fall across two or more voxels, as may be the case for high-resolution magnetic resonance visualization, then image distortion may appreciatively change the voxel signal intensities.

To approximate the length scale of the image distortion effects, higher-order slice selection effects were ignored and 3D imaging with a read gradient of strength G in the x-direction was assumed. The field of the solid particulate MRS during read-out was therefore $G_x+B_z$ if the $B_0$ offset is ignored. Spins located at a position x map to an apparent position $(x+B_z/G)$, and hyperintense and hypointense signal maxima result when $|\partial B_z/\partial x|$ takes on a minimum or maximum value, respectively. Simplifying the analysis by setting y=z=0, setting $\partial B_z/\partial x=0$ gave $x=-(J_s a^3/G)^{1/4}$ and an associated hypointense signal maximum mapped a distance d away from the solid particulate MRS given by:

$$d = \frac{4}{3}\sqrt[4]{\frac{J_s a^3}{G}} \quad (14)$$

With a compensating hyperintense signal maxima similarly displaced away from the solid particulate MRS, the ratio of d to the voxel size predicted whether image distortion significantly modified the initial signal magnitude. Although distortion was also affected by whether $B_0$ was parallel or perpendicular to the image plane, the distance d was unchanged, thus the overall distortion sizes did not depend strongly on the direction of $B_0$. Even with high magnetic moment MRS, image distortion was significant only for high-resolution imaging because d scaled as the fourth root of the magnetic dipole moment in Eqn. (14). However, for modeling the detection of single particles, high-resolution imaging was taken into consideration. For example, substituting a 1-μm diameter, $J_s=1$ T particle and a typical high-resolution imaging gradient G of a few Gauss/cm Eqn. (14) indicated that image distortion may contribute to signal strength at voxel sizes of about one hundred micrometers or less.

For solid particulate MRS with high magnetic moments and high-resolution imaging, therefore, distortion may dominate the signal in the first few milliseconds following the initial excitation, after which the signal magnitude may be dominated by dephasing effects described by Eqn. (11) above, which was assumed valid until the voxel signal started to appreciably saturate around the voxel signal saturation time $t_{sat}$ defined by Eqn. (13). In order to capture dephasing, distortion, and saturation effects simultaneously, the gradient-echo imaging of individual magnetic particles of various moments and at various image resolutions and echo times were simulated. The simulation model tracked the phases of a volume of spins precessing in the magnetic field surrounding a magnetic dipole, with intravoxel dephasing captured through a grid spacing many times smaller than the simulated voxel size. The apparent image location of each spin was determined by the net magnetic field at that spin's real location, given by the sum of the perturbing dipole field and a simulated readout gradient.

Figure 45:
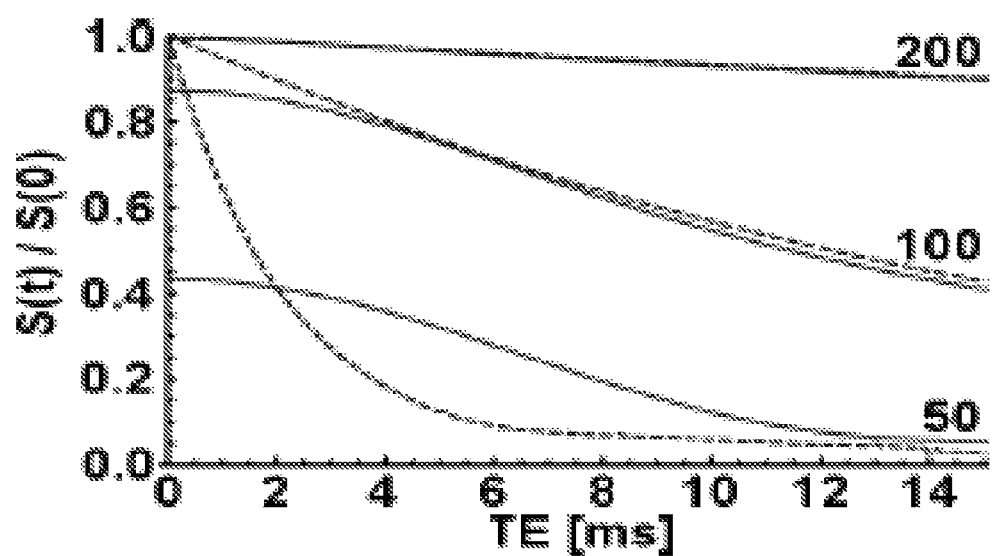
FIG. 45 is a graph comparing theoretical single voxel signal intensities from the magnetic resonance image of a solid high magnetic moment $T_2^*$ contrast agent with and without image distortion corrections.
Figure 46A:
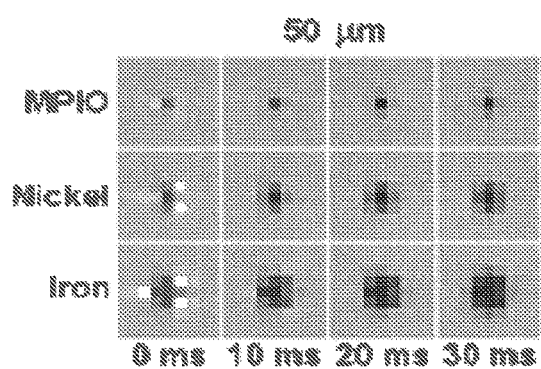
FIGS. 46A-46D are simulated gradient echo MRI images of an embodiment of a solid high magnetic moment $T_2^*$ contrast agent made of various magnetic materials.
Figure 46B:
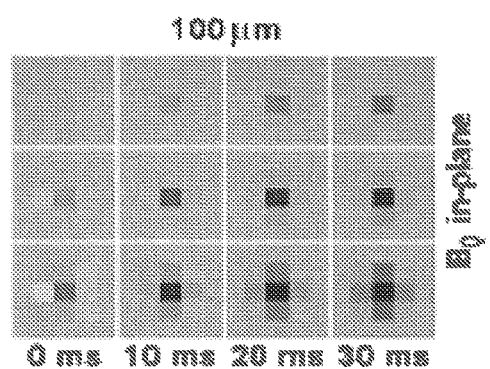
Figure 46C:
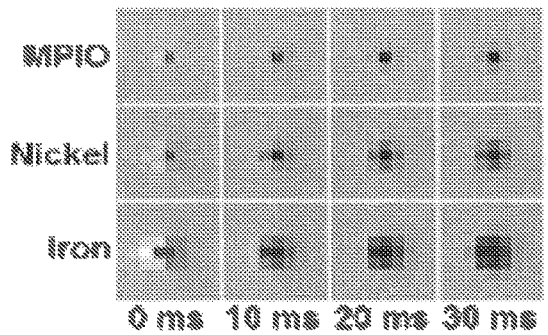
Figure 46D:
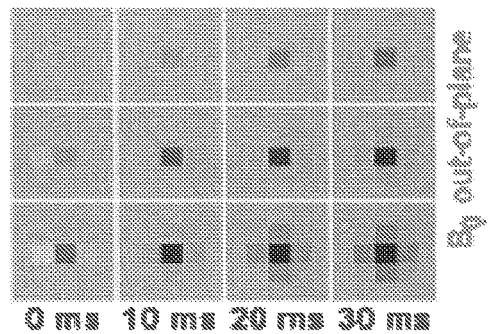

FIG. 45 is a graph summarizing theoretical single voxel signal strength from a solid particulate MRS as a function of echo time TE calculated for cubic voxel sizes of 50-μm, 100-μm, and 200-μm. The solid lines summarize the solutions obtained for theoretical voxel signal strengths for numerical simulations that included both transverse dephasing and image distortion, and the dashed lines summarize the results obtained for transverse dephasing effects only. At the larger voxel size of 200-μm, image distortion had a negligible effect on signal strength. However, as the voxel size and/or the echo time TE decreased, image distortion effects became increasingly pronounced. For example image distortion effects reduced the voxel signal strength by about 50% as the echo time approached zero for the 50-μm voxel size. The results demonstrate that image distortion must be taken in account.

Example 15

Image Simulation with Solid Particulate MRS

To compare the effects of magnetic materials used to construct solid particulate MRS, the echo times and the voxel resolution on the contrast signal generated by solid particulate MRS, the following experiment was conducted. Simulated magnetic resonance images were modeled using the methods described in Examples 14 and 15 using three different contrast particle geometries and compositions. As a reference, a commercially-available micrometer-sized iron oxide particle (MPIO, Bangs Laboratories) was modeled as a 1.63-μm diameter beads composed of 42.5% magnetite by weight and having a total magnetite content of 1.5 pg. Representative microfabricated disks were modeled as disks of pure nickel and iron having a diameter of 2-μm and a thickness of 300-nm. Both microfabricated disks were surrounded by 50 to 100-nm thick shells. All particles had roughly comparable total volumes. The magnetite, nickel, and iron materials had $J_s$ values of approximately 0.5 T, 0.6 T, and 2.2 T, respectively. As a result, the respective magnetic dipole moments of these particles were approximately $0.1\times10^{-12}$ A·m², $0.45\times10^{-12}$ A·m², and $1.65\times10^{-12}$ A·m². All particles were assumed to be centered within the image voxel. The characteristics of the three contrast agent particles are summarized in Table 1 below:

TABLE 1

| Contrast Agent Material Properties | | | | | | |
|---|---|---|---|---|---|---|
| Type of Contrast Agent | Diameter (μm) | Thickness (nm) | Magnetic material purity (% wt) | Coating thickness and material | Js of magnetic material (T) | Magnetic dipole moment (A·m²) |
| MPIO sphere | 1.63 | — | 42.5 | — | 0.5 | $0.10 \cdot 10^{-12}$ |
| nickel disk | 2 | 300 | 100 | Gold, 50-100 nm | 0.6 | $0.45 \cdot 10^{-12}$ |
| iron disk | 2 | 300 | 100 | Gold, 50-100 nm | 2.2 | $1.65 \cdot 10^{-12}$ |

FIG. 46A-46D summarizes the results of the magnetic resonance image simulations. The imaging simulations for the MPIO, nickel, and iron particles captured image darkening over several voxels rather than in only the central voxel as previously predicted in Examples 13 and 14. For each particle, the images show theoretical (noise-free) pixelized gradient-echo signals for various echo times from individual particles at 50 and at 100 micrometer (cubic) isotropic resolution and for $B_0$ oriented in-plane and perpendicular to the imaging plane. As expected, image distortion modifies the images of the nickel and iron particle signals initially, before dephasing effects begin to dominate at higher echo times.

The results of this experiment demonstrated that the micromachined solid particulate MRS generated higher contrast signals than a similarly-sized existing MPIO contrast particle.

Example 16

Effect of Off-Center Placement of Microfabricated Solid Particulate MRS in Voxels During Gradient-Echo MRI on Signal Strength To assess the effects of the location of a contrast particle within a voxel during echo-gradient MRI on the image darkening produced by the contrast particle, the following simulation was conducted. Although fractional voxel offsets have little impact at those resolutions where image darkening extends over many voxels such as in higher resolution magnetic resonance visualization performed using relatively very small voxel sizes, signal hypointensities drop substantially due to increased signal dilution arising from partial volume effects in lower resolution magnetic resonance visualization. For particles aligned in the middle of an imaging slice, therefore, identical particles may appear differently depending on their lateral registration with regard to their respective imaging voxels.

Simulated magnetic resonance images were calculated for the three different particles described in Example 15 in a similar manner. However, in addition to generating an magnetic resonance image assuming that the particle was centered within its imaging voxel, three additional locations of the particle within the voxel were calculated. The four locations are illustrated in FIG. 47 and marked as A (centered), B (centered on right edge of voxel), C (centered on top edge of voxel), and D (corner of voxel). All simulated magnetic resonance images were calculated assuming 100-µm voxel resolution and a 10 ms echo time.

FIG. 47 summarizes the magnetic resonance images calculated for the three different contrast agents described in Example 15. For each of the contrast agents, position-dependent signal dilution was observed. Signal hypointensity decreased as dephasing effects were averaged over an increasing number of voxels, and decreased most severely when the particle was located at the corner of a voxel, where the dephasing effects may be averaged over as many as eight voxels in three-dimensional imaging. The position-dependent signal dilution rendered the MPIO contrast particle invisible when the particle was located at a voxel corner (position D in FIG. 47).

Overall signal hypointensity ranges were approximated using the simulated magnetic resonance images because the echo time used was selected such that image distortion and the saturation of surrounding voxels was negligible. For example, in moving from a central point (A) to a corner point (D), signal hypointensity drops nearly four-fold in two-dimensional imaging. Similarly, in three dimensional imaging an offset from voxel center to corner reduces signal hypointensity as much as eight-fold.

The results of this experiment demonstrated that the strength of the signal of a contrast particle during magnetic resonance visualization is sensitive to the position of the contrast particle within the imaging voxel. Further, in order to enhance the visibility of the contrast particle at arbitrary placement within the voxels during magnetic resonance visualization, high magnetic moment contrast particles such as the nickel or iron disks may be preferred.

Example 17

Comparison of Experimental MRI Images of Solid Particulate MRS vs. MPIO

To compare the visibility of solid particulate MRS contrast agents to existing iron oxide micro-particles (MPIO), the following experiment was conducted. Contrast particles similar to those described in Example 15 were suspended in three separate agarose samples and subjected to $T_2^*$-weighted, 12 ms TE, gradient-echo MRI at 50-µm and 100-µm isotropic resolution.

FIGS. 48A-48F are representative MRI images obtained for the three different contrast particles. The top row of images (FIGS. 48A-48C) is images taken at a 50-µm isotropic resolution, and the bottom row (FIGS. 48D-48F) are images taken at a 100-µm isotropic resolution. The left column (FIGS. 48A and 48D) are images of the MPIO contrast particles, the center column (FIGS. 48B and 48E) are images of the nickel disks, and the right column (FIGS. 48C and 48F) are images of the iron disks, all described previously in Example 15.

As expected, higher magnetic moment particles caused more pronounced image darkenings. Localized hypointense regions in all images were assumed to be primarily due to single particles due to the low particle concentrations used and by the good agreement, at least for the microfabricated particles, between the calculated and experimentally measured signal intensities.

To quantitatively compare the calculated and experimentally measured signal intensities, all 100-micrometer resolution image slices including those shown in FIG. 48 were analyzed using image analysis software that automatically selected and recorded the pixel intensity of all localized dark regions in each image. The data were collected into histograms of normalized signal intensities (S(TE)/S(0)) approximated from the images by taking the ratio of signal intensity of the darkest voxels in each darkened region to the signal intensity averaged from a particle-free region of the sample image. For comparison, the experimental intensity distributions integrated the signal intensity over variations in particle magnetic moment, particle registration with respect to lateral voxel position and image slice height, and background noise.

Figure 49A:
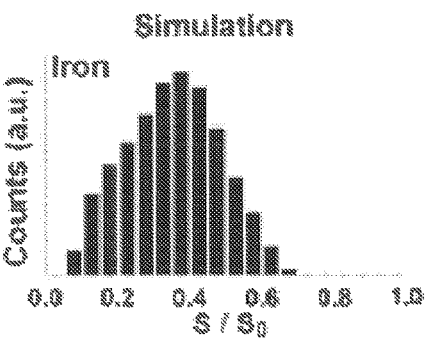
FIGS. 49A-49F are histograms of single-voxel signal intensities from theoretical and experimental magnetic resonance images of microfabricated contrast agents normalized to the background signal intensity.
Figure 49B:
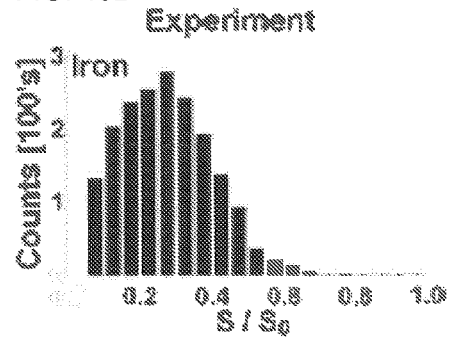
Figure 49C:
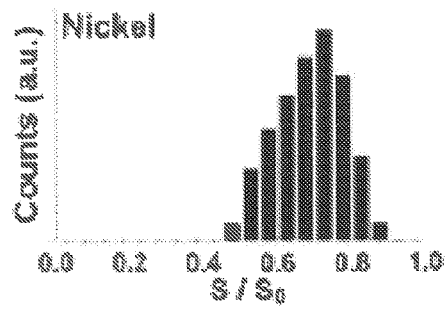
Figure 49D:
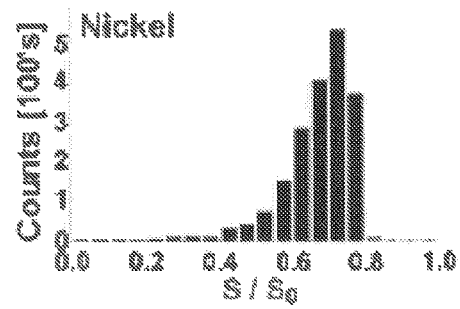
Figure 49E:
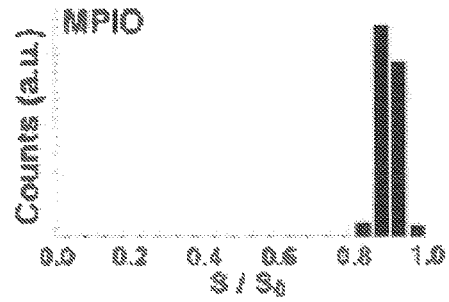
Figure 49F:
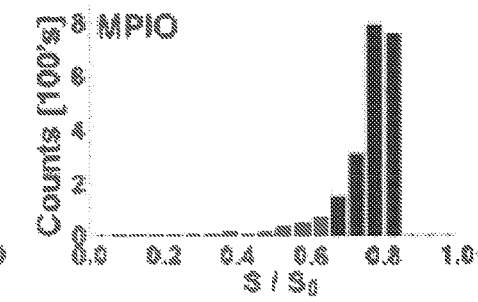
Figures 50A, 50B, 50C, 50D, 50E, 50F:
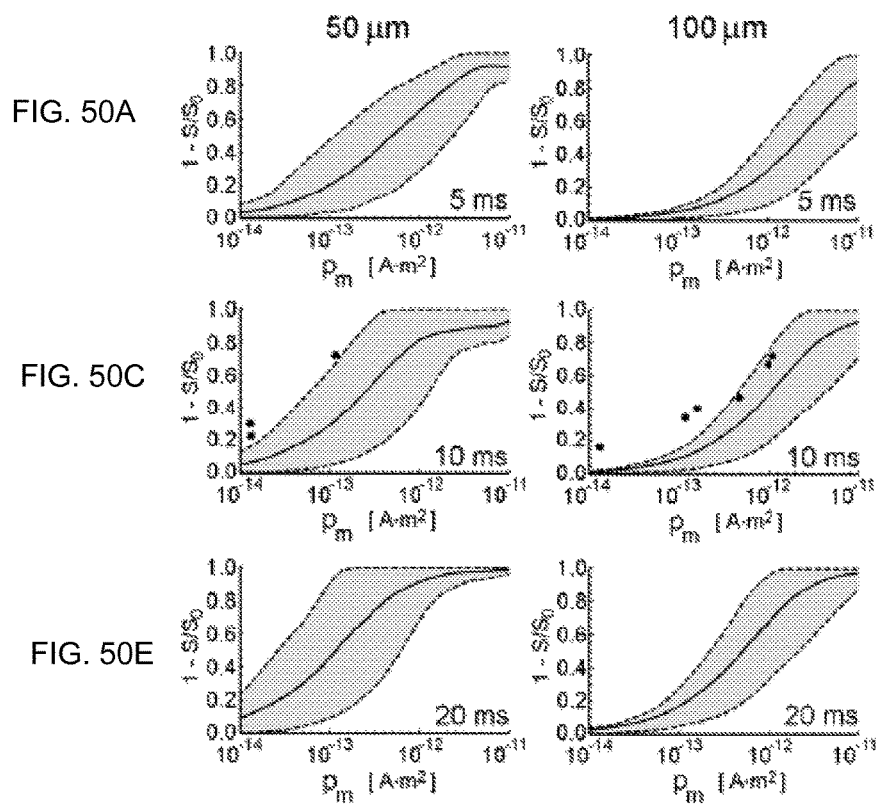
FIGS. 50A-50F are graphs showing the fractional hypointensity $(1-S/S_0)$ as a function of dipole moment for various isotropic (cubic) resolutions and echo times.

FIGS. 49A-49C are histograms summarizing the simulated and experimentally measured signal intensities of the iron disks, nickel disks, and MPIO contrast particles, respectively. For all contrast particles, the simulated and the experimental histograms showed hypointensity distributions that were non-Gaussian and too broad to be explained by background noise alone. Instead, the histograms indicated that the contrast signals were dominated by subvoxel-level variation in the particle location.

The results of this experiment indicated that the experimentally measured magnetic resonance visualization signal intensities of the contrast particles were in good agreement with theoretically predicted signal intensity calculations for the solid particulate MRS. For comparison, the experimental intensity distributions, which integrated the signal intensity over variations in particle magnetic moment, particle registration with respect to lateral voxel position and image slice height, and background noise, were compared to theoretical (background noise-free) calculations.

Example 18

Determination of Minimum Particle Moments to Ensure Visibility of Solid Particulate MRS To determine the minimum particle magnetic moments necessary to assure the visibility of the solid particulate MRS during echo-gradient MRI, the following simulation was conducted. Contrast signal intensities were calculated for a spherical particle with a magnetic moment ranging from about $10^{-14}$ A·m$^2$ to about $10^{-11}$ A·m$^2$ using the methods described in Example 15. At each magnetic moment, signal intensities were calculated for an ensemble of particles that were positioned randomly with respect to the imaging voxel locations. Simulated magnetic resonance visualization signal intensities were calculated assuming an isotropic resolution of 50-µm and 100-µm, and echo times of 5 ms, 10 ms, and 20 ms.

FIGS. 50A-50F are graphs summarizing the calculated image intensities for all conditions described above. Empirical MPIO contrast signal data are superimposed on FIGS. 50C and 50D for comparison. The lower boundaries of the relative signal intensities are all greater than zero, but must be greater than background noise signals to be visual. Contrast particles having magnetic moments above the $10^{-13}$ A·m$^2$ threshold are predicted to be visible above relatively low background noise for all conditions examined. This magnetic moment threshold is slightly lower for higher echo times and/or higher image resolutions.

The results of this experiment predicted that contrast particles having a magnetic moment of at least $10^{-13}$ A·m$^2$ are visible above low background noise over a variety of magnetic resonance visualization conditions.

Example 19

Super-Resolution Tracking Using Solid Particulate MRS

To demonstrate the potential use of solid particulate MRS in super-resolution tracking, in which the sub-voxel location of a particle may be determined, the following experiment was conducted. Solid particulate MRS that included iron disks coated in gold, similar to those described in Example 15 were suspended in agarose and subjected to echo-gradient MRI as described in Example 17.

Figure 51:
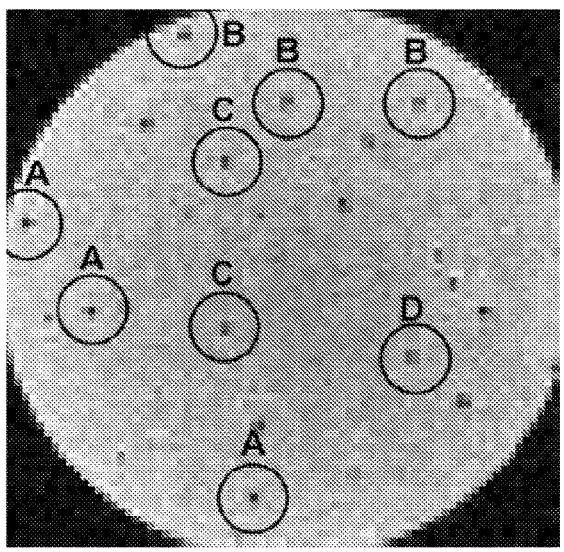
FIG. 51 is a gradient-echo MRI image of microfabricated iron disks suspended in agarose.

A representative MRI image is shown in FIG. 51. In FIG. 51, individual solid particulate MRS were detected within the image. In addition, due to the consistent size and composition of the solid particulate MRS, the signal intensity of an individual solid particulate MRS could be compared to the signal intensities of the other solid particulate MRS to determine the location of the particle within the imaging voxels. For example, the darkest voxels were assumed to indicate particles centered within the voxel, and the lighter or more dispersed particle signals were assumed to be off-center. The degree of lightening and/or signal dispersion were used to narrow down the location of the particle within the imaging voxels using the information from the calculated image intensities shown in FIG. 47. On FIG. 51, individual particles are circled and labeled using a similar convention to that of FIG. 47: the letter A denotes particles centered in the imaging voxel, B and C denote particles on the top or side edges of a voxel, respectively, and D denotes a particle on a voxel corner.

The results of this experiment demonstrated that the uniform composition and size of the solid particulate MRS enabled these contrast particles to be used for super-resolution tracking.

The invention has been described in detail with respect to various embodiments, and it will now be apparent from the foregoing to those skilled in the art that changes and modifications may be made without departing from the invention in its broader aspects, and the invention, therefore, as defined in the claims is intended to cover all such changes and modifications as fall within the true concept of the invention.

The invention claimed is:

1. A magnetic resonance contrast agent comprising a plurality of contrast structures, each contrast structure consisting of:
   (a) a magnetic material arranged as a pair of disks defining a space between a circular surface of each disk, wherein the centers of the circular surfaces of the disks are arranged along a same axis normal to the circular surfaces, wherein the circular surfaces are parallel to each other, and wherein each disk consists of one or more layers of a material selected from the group consisting of a ferromagnetic material, a paramagnetic material, a superparamagnetic material, an alloy, a magnetic compound, and a combination thereof; and
   (b) a non-magnetic spacer arranged between the disks, wherein the non-magnetic spacer consists of a material selected from the group consisting of a metal, a photo-epoxy, a hydrogel, a polymer, a ceramic, a plastic, a photoresist, and a combination thereof;
   wherein each contrast structure has a maximum dimension between about 10 nm and about 100 µm, and
   wherein the space creates a spatially extended region contained within a near-field region of the contrast structure over which an applied magnetic field results in a homogeneous field, such that nuclear magnetic moments of a second material when arranged within said spatially extended region precess at a characteristic Larmor frequency, whereby the magnetic resonance contrast agent is adapted to emit a characteristic magnetic resonance signal of the magnetic material.

2. The magnetic resonance contrast agent of claim 1, wherein the non-magnetic spacer is configured to change in geometry in response to the environment of the magnetic resonance contrast agent, and wherein the change in geometry changes the spacing between the disks, thereby changing the magnitude of the homogeneous field.

3. The magnetic resonance contrast agent of claim 2, wherein the geometry of non-magnetic material changes in response to pH, temperature, or solution salinity.

4. The magnetic resonance contrast agent of claim 3, wherein the non-magnetic material expands or contracts in response to a change in temperature, thereby increasing or decreasing the spacing between the disk-shaped magnetic portions.

5. The magnetic resonance contrast agent of claim 3, wherein the non-magnetic material expands or contracts in response to a change in pH, thereby increasing or decreasing the spacing between the disks.

6. The magnetic resonance contrast agent of claim 3, wherein the non-magnetic material consists of a hydrogel.

7. The magnetic resonance contrast agent of claim 2, wherein geometry of the non-magnetic spacer changes in response to pressure, vibration, orientation changes, or torque.

8. The magnetic resonance contrast agent of claim 2, wherein the non-magnetic spacer decomposes or disconnects from at least one of the disks in response to the environment.

9. The magnetic resonance contrast agent of claim 8, wherein the decomposition or disconnection of the non-magnetic spacer disrupts the arrangement of the disks, thereby eliminating the homogeneous field.

10. The magnetic resonance contrast of claim 2, wherein the non-magnetic spacer disintegrates in response to the environment.

11. A method of performing magnetic resonance imaging, comprising:
    (a) providing the magnetic resonance contrast agent of claim 1 dispersed in a medium;
    (b) illuminating the magnetic resonance contrast agent with an excitatory electromagnetic pulse; and
    (c) detecting electromagnetic radiation emitted from the magnetic resonance contrast agent with a detection system.

12. The method of claim 11, wherein the medium is a liquid.

* * * * *